US010150753B2

(12) United States Patent
Jones et al.

(10) Patent No.: US 10,150,753 B2
(45) Date of Patent: Dec. 11, 2018

(54) SALT FORMS AND POLYMORPHS OF (R)-1-(4-(6-(2-(4-(3,3-DIFLUOROCYCLOBUTOXY)-6-METHYLPYRDIN-2-YL)ACETAMIDO)PYRIDAZIN-3-YL)-2-FLUOROBUTYL)-N-METHYL-1H-1,2,3-TRIAZOLE-4-CARBOXAMIDE

(71) Applicant: Board of Regents, The University of Texas System, Austin, TX (US)

(72) Inventors: Philip Jones, Houston, TX (US); Michael J. Soth, Sugar Land, TX (US); Jason P. Burke, Houston, TX (US); Kang Le, Sugar Land, TX (US); Gang Liu, Sugar Land, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/387,560

(22) Filed: Dec. 21, 2016

(65) Prior Publication Data
US 2017/0174661 A1 Jun. 22, 2017

Related U.S. Application Data

(60) Provisional application No. 62/271,018, filed on Dec. 22, 2015.

(51) Int. Cl.
*C07D 401/14* (2006.01)
*A61K 31/501* (2006.01)
*A61K 45/06* (2006.01)

(52) U.S. Cl.
CPC .......... *C07D 401/14* (2013.01); *A61K 31/501* (2013.01); *A61K 45/06* (2013.01); *C07B 2200/13* (2013.01)

(58) Field of Classification Search
CPC .................................................. C07D 401/04
See application file for complete search history.

(56) References Cited

U.S. PATENT DOCUMENTS

| | | | |
|---|---|---|---|
| 4,399,140 | A | 8/1983 | Gacek |
| 4,720,447 | A | 1/1988 | De |
| 6,153,628 | A | 11/2000 | Jin |
| 7,956,070 | B2 | 6/2011 | Alcaraz |
| 9,809,588 | B2 | 11/2017 | Di Francesco |
| 2002/0115698 | A1 | 8/2002 | Newcomb |
| 2009/0215750 | A1 | 8/2009 | Bamberg |
| 2010/0255117 | A1 | 10/2010 | Biswal |
| 2012/0202776 | A1 | 8/2012 | Wang |
| 2013/0157998 | A1 | 6/2013 | Li |
| 2014/0050699 | A1 | 2/2014 | Li |
| 2014/0142081 | A1 | 5/2014 | Lemieux |
| 2016/0002204 | A1 | 1/2016 | Di Francesco |
| 2016/0002248 | A1 | 1/2016 | Di Francesco |
| 2016/0009704 | A1 | 1/2016 | Di Francesco |
| 2016/0058759 | A1 | 3/2016 | Heffernan |
| 2017/0001996 | A1 | 1/2017 | Lewis |
| 2017/0291895 | A1 | 10/2017 | Di Francesco |

FOREIGN PATENT DOCUMENTS

| | | |
|---|---|---|
| WO | 1991009848 A1 | 7/1991 |
| WO | 1998043962 | 10/1998 |
| WO | 1999026945 | 6/1999 |
| WO | 2008083238 A2 | 7/2008 |
| WO | 2010023946 A1 | 3/2010 |
| WO | 2010099527 A1 | 9/2010 |
| WO | 2010111504 | 9/2010 |
| WO | 2011089995 | 7/2011 |
| WO | 2011143160 A2 | 11/2011 |
| WO | 2013078123 A1 | 5/2013 |
| WO | 2014078645 A1 | 5/2014 |
| WO | 2014089048 A1 | 6/2014 |
| WO | 2014119696 | 8/2014 |
| WO | 2015101957 A2 | 7/2015 |
| WO | 2016004404 A2 | 1/2016 |
| WO | 2016004413 A2 | 1/2016 |
| WO | 2016004417 A1 | 1/2016 |
| WO | 2016004417 A3 | 1/2016 |
| WO | 2016004418 A1 | 1/2016 |
| WO | 2016004418 A3 | 1/2016 |
| WO | 2016004404 A3 | 3/2016 |
| WO | 2016004413 A3 | 3/2016 |
| WO | 2017004359 A1 | 1/2017 |

OTHER PUBLICATIONS

Pinedo et al. (2000).*
McMahon et al. (2000).*
Aurora Fine Chemicals, 1-[3-(3-aminopyrazol-1-yl)propyl]pyrazole-4-carboxamide, Cat. No. A04.256.259 http://online.aurorafinechemicals.com/StrSearch.asp, Jul. 1, 2015.
Brunton et al., Chemotherapy of NEoplastic Disease in, Goodman and Gilman's, The Pharmacological Basis for Therapeutics, eds., 11 th ed., 2008, pp. 853-903.
CAS Indexed Compounds, 2(1H)-Pyridinone, 1-[3-1-phenyl-1H-tetrazol-5-yl)propyl]-5(trifluoromethyl), Registry No. 1311902-55-2, Jul. 7, 2011.
CAS Indexed Compounds, 2(1H)-Pyridinone, 1-[3- (3-amino-1H-pyrazol-1-yl)propyl]-4-methyl, Registry No. 1284137-43-4, Apr. 22, 2011.
CAS Indexed Compounds, 2(1H)-Pyridinone, 1-[3-(3-amino-1H-pyrazol-1-yl)propyl]-5-bromo, Registry No. 1272932-30-5, Mar. 31, 2011.
CAS Indexed Compounds, 2(1H)-Pyridinone, 1-[3-(3-amino-1H-pyrazol-1-yl)propyl]-5(trifluoromethyl), Registry No. 1406035-29-7, Nov. 25, 2012.
CAS Indexed Compounds, 2(1H)-Pyridinone, 1-[3-(3-amino-1H-pyrazol-1-yl)propyl], Registry No. 1341730-05-9, Nov. 6, 2011.
CAS Indexed Compounds, 2(1H)-Pyridinone, 1-[3-[3-(3-fluoro-4-methylphenyl)-1,2,4-oxadiazol-5yl]propyl]-5-(trifluoromethyl), Registry No. 1387392-92-8, Aug. 7, 2012.

(Continued)

*Primary Examiner* — Paul V Ward
(74) *Attorney, Agent, or Firm* — Dennis A. Bennett; Cynthia Hathaway; John Desper

(57) ABSTRACT

Disclosed herein is the compound (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide, and salt forms and polymorphs thereof demonstrating improved exposure after oral dosing. Methods of inhibition GLS1 activity in a human or animal subject are also provided.

15 Claims, 32 Drawing Sheets

(56) References Cited

OTHER PUBLICATIONS

CAS Indexed Compounds, 2(1H)-Pyridinone, 1-[3-[4-(chloromethyl)-2-thiazolyl]propyl]-4-methyl, Registry No. 1408458-49-0, Nov. 30, 2012.
CAS Indexed Compounds, 2(1H)-Pyridinone, 1-[3-[4-(chloromethyl)-2-thiazolyl]propyl]-5(trifluoromethyl), Registry No. 1484369-40-5, Dec. 1, 2013.
CAS Indexed Compounds, 2(1H)-Pyridinone, 1-[3-[4-(chloromethyl)-2-thiazolyl]propyl], Registry No. 1094436-44-8, Jan. 20, 2009.
CAS Indexed Compounds, 2(1H)-Pyridinone, 1-[4-[4-(chloromethyl)-2-thiazolyl]butyl]-4-methyl, Registry No. 1284050-00-5, Apr. 22, 2011.
CAS Indexed Compounds, 2(1H)-Pyridinone, 1-[4-[4-(chloromethyl)-2-thiazolyl]butyl], Registry No. 1272826-97-7, Mar. 31, 2011.
CAS Indexed Compounds, 2(1H)-Pyridinone, 1-[4-oxo-4-(2-thienyl)butyl]-5-(trifluoromethyl), Registry No. 1456227-69-2, Oct. 6, 2013.
CAS Indexed Compounds, 2(1H)-Pyridinone, 1-[4-oxo-4-(2-thienyl)butyl], Registry No. 1456935-71-9, Oct. 11, 2013.
CAS Indexed Compounds, 2(1H)-Pyridinone, 5-(trifluoromethyl)-1-[3-[3-[3-(trifluoromethyl)phenyl], Registry No. 1100005-80-8, Feb. 3, 2009.
CAS Indexed Compounds, 2(1H)-Pyridinone, 5-bromo-1-[3-(1H-imidazol-1-yl)propyl], Registry No. 1482686-39-4, Nov. 28, 2013.
CAS Indexed Compounds, 2(1H)-Pyridinone, 5-bromo-1-[4-oxo-4-(2-thienyl)butyl], Registry No. 1458260-86-0, Oct. 15, 2013.
CAS Indexed Compounds, 4-Pyridinecarboxylic acid, 1,2-dihydro-1-[3-(1H-imidazol-1-yl)propyl)]-2-Oxo, Registry No. 1548114-27-7, Feb. 18, 2014.
Di Francesco, Maria Emilia et al., New heterocyclic compound used in pharmaceutical composition and for manufacturing medicament for treating glutaminase-mediated disorder selected from immunological disorders, neurological disorders or cancer, University Texas System, US20160002204A1, Non-Final Rejection, Apr. 11, 2016.
Di Francesco, Maria Emilia et al., New substituted amide compounds are glutaminase-1 (GLS1) inhibitors useful for treating a GLS1-mediated disorder, which is cancer e.g. acute lymphoblastic leukemia, immunological disorder and neurological disorder in a subject who is human, University Texas System, US20160009704 A1, Non-Final Rejection, May 31, 2016.
Golub TR et al., Molecular classification of cancer: class discovery and class prediction by gene expression monitoring, Science, Oct. 15, 1999;286(5439): pp. 531-537.
Gross et al., Antitumor activity of the glutaminase inhibitor CB-839 in triple-negative breast cancer, Mol. Cancer Ther. 13(4):890-901, 2014.
Inami et al., 'Persistent activation of Nrf2 through p62 in hepatocellular carcinoma cells', The Journal of Cell Biology, (Apr. 1, 2011), vol. 193, No. 2, pp. 275-284, XP055158643.
International Preliminary Report on Patentability dated Jan. 12, 2017 for International Application No. PCT/US2015/039134.
International Preliminary Report on Patentability dated Jan. 12, 2017 for International Application No. PCT/US2015/039150.
Katt, et al., "Glutaminase regulation in acancer cells: a druggable chain of events," Drug Discov Today, 2014, vol. 19(4), pp. 450-457, entire document, especially p. 13, Figure 1, Assymetric BPTES Analog.
Lala PK etal., Role of nitric oxide in tumor progression: lessons from experimental tumors, Cancer Metastasis Rev. Mar. 1998;17(1): pp. 91-106.
Li et al., 'Sulforaphane Potentiates the Efficacy of 17-Allylamino 17-Demethoxygeldanamycin Against Pancreatic Cancer Through Enhanced Abrogation of Hsp90 Chaperone Function', Nutrition and Cancer, (Aug. 29, 2011), vol. 63, No. 7, pp. 1151-1159, XP055167208.
Robinson et al., 'Novel mechanism of inhibition of rat kidney-type glutaminase by bis-2-(5-phenylacetamido-1,2,4-thiadiazol-2-yl)ethyl sulfide (BPTES).', The Biochemical Journal, (Sep. 15, 2007), vol. 406, pp. 407-414, XP055069615.
Rotblat et al., 'NRF2 and p53: Januses in cancer?' Oncotarget, (Nov. 19, 2012), vol. 3, No. 11, pp. 1272-1283, XP055251330.
Shukla, et al., Design, synthesis, and pharmacological evaluation of bis-2-(5-phenylacetamido-1,2,4-thiadiazol-2-yl)ethyl sulfide 3 (BPTES) analogs as glutaminase inhibitors, J. Med. Chem. 55(23):10551-63, 2012.
Stanovnik B et al., The tautomerism of heterocycles: substituent tautomerism of six-membered ring heterocycles, Advances in Heterocyclic Chemistry 91, 2006, pp. 1-134.
Thangavelu et al., 'Structural basis for the allosteric inhibitory mechanism of human kidney-type glutaminase (KGA) and its regulation by Raf-Mek-Erk signaling in cancer cell metabolism', Proc. Natl. Acad. Sci. USA, (May 15, 2012), vol. 109, No. 20, pp. 7705-7710, XP055251346.
Wise DR etal., Glutamine addiction: a new therapeutic target in cancer, Trends Biochem Sci. Aug. 2010;35(8): pp. 427-433.
Zhang et al., 'Distinct Cysteine Residues in Keap1 Are Required for Keap1-Dependent Ubiquitination of Nrf2 and for Stabilization of Nrf2 by Chemopreventive Agents and Oxidative Stress', Molecular and Cellular Biology, (Nov. 1, 2003), vol. 23, No. 22, pp. 8137-8151, XP055251345.
Zhang et al., 'Loss of Kelch-Like ECH-Associated Protein 1 Function in Prostate Cancer Cells Causes Chemoresistance and Radioresistance and Promotes Tumor Growth', Molecular Cancer Therapeutics, (Feb. 1, 2010), vol. 9, No. 2, pp. 336-347, XP055227547.
International Search Report and Written Opinion for PCT Application No. PCT/US2016/40364, dated Sep. 23, 2016, filed on Jun. 30, 2016, 10 pages.
International Search Report and Written Opinion for PCT Application No. PCT/US2016/68149, dated Mar. 27, 2017, filed on Dec. 21, 2016, 6 pages.
Wang JB et al., Targeting mitochondrial glutaminase activity inhibits oncogenic transformation, Cancer Cell. Sep. 14, 2010;18(3):207-219.
Blair SL et al., Glutathione metabolism in patients with non-small cell lung cancers, Cancer Res. Jan. 1, 1997;57 (1):152-5.
Gorrini C et al., Modulation of oxidative stress as an anticancer strategy, Nat Rev Drug Discov. Dec. 2013;12 (12):931-947.
International Application No. PCT/US2015/039134; International Preliminary Report on Patentability, date of issuance Jan. 3, 2017; 06 pages.
International Application No. PCT/US2015/039134; International Search Report and Written Opinion of the International Search Authority, dated Feb. 9, 2016; 10 pages.
International Application No. PCT/US2015/039143; International Preliminary Report on Patentability, dated Jan. 3, 2017; 06 pages.
International Application No. PCT/US2015/039143; International Search Report and Written Opinion of the International Search Authority, dated Jan. 11, 2016; 10 pages.
International Application No. PCT/US2015/039150; International Search Report and Written Opinion of the International Search Authority, dated Dec. 4, 2015.
International Application No. PCT/US2015/039153; International Preliminary Report on Patentability, dated Jan. 3, 2017; 10 pages.
International Application No. PCT/US2015/039153; International Search Report and Written Opinion of the International Search Authority, dated Jan. 7, 2016; 12 pages.
International Application No. PCT/US2016/040364; International Preliminary Report on Patentability, dated Jan. 2, 2018; 7 pages.
Singh A et al., Dysfunctional KEAP1-NRF2 interaction in non-small-cell lung cancer, PLoS Med. Oct. 2006;3(10):e420, pp. 1-10.
U.S. Appl. No. 14/791,186; Examiner Initiated Interview Summary dated Dec. 6, 2016; 1 page.
U.S. Appl. No. 14/791,186; Final Office Action dated Dec. 6, 2016; 31 pages.
U.S. Appl. No. 14/791,186; Notice of Allowance dated Mar. 15, 2017; 08 pages.
U.S. Appl. No. 14/791,186; Notice of Allowance dated May 11, 2017; 05 pages.
U.S. Appl. No. 14/791,284; Notice of Allowance dated Nov. 18, 2016; 04 pages.
U.S. Appl. No. 14/791,284; Notice of Allowance dated Oct. 14, 2016; 09 pages.

(56) References Cited

OTHER PUBLICATIONS

U.S. Appl. No. 14/791,307; Non-Final Office Action dated Jun. 21, 2017; 12 pages.
U.S. Appl. No. 15/199,100; Non-Final Office Action for dated Sep. 13, 2017; 11 pages.
U.S. Appl. No. 15/851,407; Application as filed dated Dec. 21, 2017; 107 pages.
International Application No. PCT/US2016/068149; International Preliminary Report on Patentability, dated Jul. 6, 2018; 4 pages.
U.S. Appl. No. 15/199,100; Examiner Initiated Interview Summary dated Jul. 6, 2018; 1 page.
U.S. Appl. No. 15/199,100; Notice of Allowance dated Jul. 6, 2018; 11 pages.
U.S. Appl. No. 15/199,100; Notice of Allowance dated Jul. 30, 2018; 8 pages.
U.S. Appl. No. 15/624,168; Non-Final Office Action dated Jul. 13, 2018; 9 pages.
WO 2014119696-A1 ProQuest English Machine Translation Jul. 6, 2018 p. 1-425.

* cited by examiner

SALT FORMS AND POLYMORPHS OF (R)-1-(4-(6-(2-(4-(3,3-DIFLUOROCYCLOBUTOXY)-6-METHYLPYRDIN-2-YL)ACETAMIDO)PYRIDAZIN-3-YL)-2-FLUOROBUTYL)-N-METHYL-1H-1,2,3-TRIAZOLE-4-CARBOXAMIDE

This application claims the benefit of priority of U.S. Provisional application No. 62/271,018, filed Dec. 22, 2015, the disclosure of which is hereby incorporated by reference as if written herein in its entirety. This application also incorporates by reference the disclosure of U.S. application Ser. No. 14/791,186, filed Jul. 2, 2015, in its entirety.

The present disclosure relates to new heterocyclic compounds, salts and polymorphs thereof, compositions, and their application as pharmaceuticals for the treatment of disease. Methods of inhibition of GLS1 activity in a human or animal subject are also provided for the treatment of diseases such as cancer.

Figure 1:
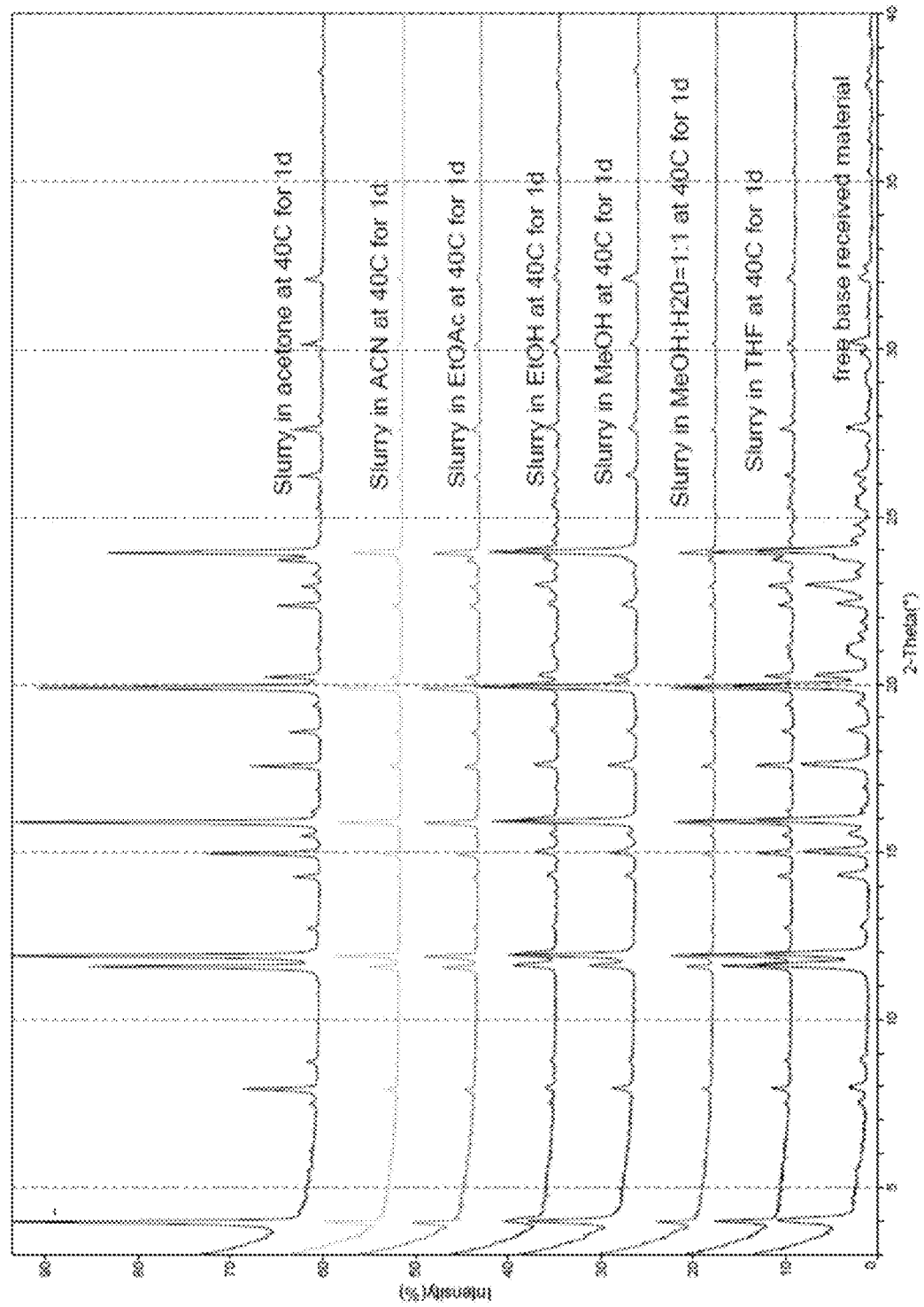
FIG. 1 is an overlay of XRPD of Example 1 after purification in various solvents.

Metabolic deregulation is a hallmark of cancer as tumors exhibit an increased demand for nutrients and macromolecules to fuel their rapid proliferation. Glutamine (Gln), the most abundant amino acid in circulation, plays an essential role in providing cancer cells with biosynthetic intermediates required to support proliferation and survival. Specifically, glutaminolysis, or the enzymatic conversion of glutamine to glutamate, provides proliferating cancer cells with a source of nitrogen for amino acid and nucleotide synthesis, and a carbon skeleton to fuel ATP and NADPH synthesis through the TCA cycle. In addition to supporting cell growth, glutamine metabolism plays a critical role in maintaining cellular redox homeostasis as glutamate can be converted into glutathione, the major intracellular antioxidant.

Glutaminolysis is regulated by mitochondrial glutaminase (GLS), the rate limiting enzyme that catalyzes the conversion of Gln to glutamate and ammonia. Mammalian cells contain 2 genes that encode glutaminase: the kidney-type (GLS1) and liver-type (GLS2) enzymes. Each has been detected in multiple tissue types, with GLS1 being widely distributed throughout the body. GLS1 is a phosphate-activated enzyme that exists in humans as two major splice variants, a long form (referred to as KGA) and a short form (GAC), which differ only in their C-terminal sequences. Both forms of GLS1 are thought to bind to the inner membrane of the mitochondrion in mammalian cells, although at least one report suggests that glutaminase may exist in the intramembrane space, dissociated from the membrane. GLS is frequently overexpressed in human tumors and has been shown to be positively regulated by oncogenes such as Myc. Consistent with the observed dependence of cancer cell lines on glutamine metabolism, pharmcological inhibition of GLS offers the potential to target Gln addicted tumors.

Thus, there is a need for glutaminase inhibitors that are specific and capable of being formulated for in vivo use.

Accordingly, disclosed herein are new compositions and methods for inhibiting glutaminase activity.

Provided is the compound

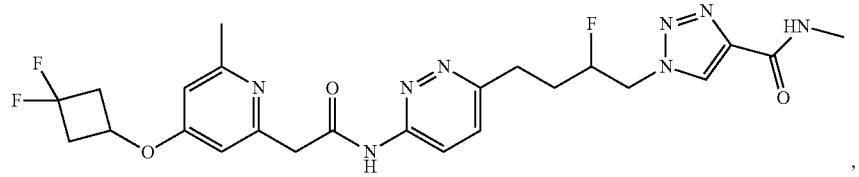

or a salt, solvate, or polymorph thereof.

Also provided is the compound

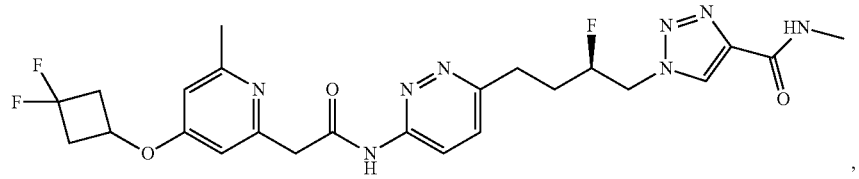 [SMILES: CNC(=O)c1cn(C[C@H](F)CCc2ccc(NC(=O)Cc3cc(OC4CC(F)(F)C4)cc(C)n3)nn2)nn1]

or a salt, solvate, or polymorph thereof.

Also provided is the compound

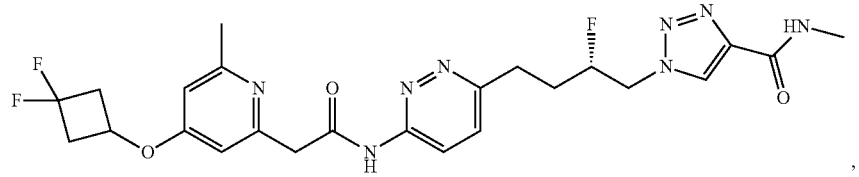 [SMILES: CNC(=O)c1cn(C[C@@H](F)CCc2ccc(NC(=O)Cc3cc(OC4CC(F)(F)C4)cc(C)n3)nn2)nn1]

or a salt, solvate, or polymorph thereof.

In certain embodiments, the compound is a solvate. In certain embodiments, the solvate is DMSO. In certain embodiments, wherein the DMSO is associated with the compound in a 1:1 ratio.

Also provided is a salt of structural Formula I

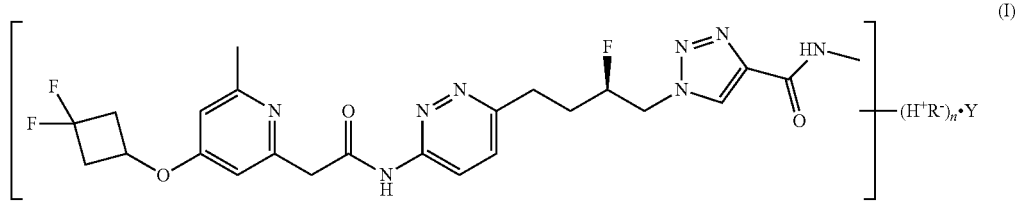

or a solvate or polymorph thereof, wherein:

$R^-$ is chosen from $Cl^-$, $Br^-$, $I^-$, $HSO_4^-$, $SO_4^{2-}$, $NO_3^-$, $CH_3SO_3^-$, $PhSO_3^-$, $4\text{-MePhSO}_3^-$, and $NaphthaleneSO_3^-$;

n is an integer from 0 to 2; and

Y is an optional solvate.

In certain embodiments, $R^-$ is chosen from $Cl^-$, $HSO_4^-$, $CH_3SO_3^-$, and $4\text{-MePhSO}_3^-$.

In certain embodiments, n is 1.

In certain embodiments, Y is absent (i.e., the salt is anhydrous).

In certain embodiments, $R^-$ is $CH_3SO_3^-$ (i.e., the salt is the mesylate).

In certain embodiments, the mesylate salt is characterized as having one or more x-ray powder diffraction peaks chosen from about 9.2, about 10.8, about 13.8, about 16.7, about 17.3, about 18.4, about 18.7, about 19.9, about 20.6, about 21.4, about 22.1, about 22.3, about 22.6, about 22.9, about 24.1, and about 32.1 degrees 2-theta. In certain embodiments, the salt has three or more of the peaks. In certain embodiments, the salt has five or more of the peaks.

In certain embodiments, the mesylate salt displays an endothermic peak in DSC with onset of 180° C.±1° C. In certain embodiments, the mesylate salt displays weight loss in DSC of less than 1.0% from 30° C. to 200° C. In certain embodiments, the mesylate salt is anhydrous.

In certain embodiments, $R^-$ is $Cl^-$ (i.e., the salt is the chloride).

In certain embodiments, the chloride salt is characterized as having one or more x-ray powder diffraction peaks chosen from about 4.6, about 9.26, about 11.0, about 12.6, about 13.2, about 13.8, about 16.5, about 19.0, about 20.8, about 22.0, about 22.4, about 22.7, about 24.2, about 25.0, and about 33.4 degrees 2-theta. In certain embodiments, the salt has three or more of the peaks. In certain embodiments, the salt has five or more of the peaks.

In certain embodiments, R⁻ is 4-MePhSO₃⁻ (i.e., the salt is the tosylate).

In certain embodiments, the tosylate salt is characterized as having one or more x-ray powder diffraction peaks chosen from about 4.5, about 9.0, about 10.3, about 10.5, about 10.7, about 11.1, about 11.7, about 13.6, about 14.3, about 17.1, about 17.3, about 17.6, about 18.5, about 18.9, about 19.0, about 19.2, about 19.8, about 20.1, about 20.4, about 20.8, about 21.4, about 21.8, about 22.4, about 22.6, about 23.4, about 24.3, about 25.1, about 26.0, about 26.3, about 27.2, about 27.4, and about 28.2 degrees 2-theta. In certain embodiments, the salt has three or more of the peaks. In certain embodiments, the salt has five or more of the peaks.

In certain embodiments, the tosylate salt displays an endothermic peak in DSC with onset of 185° C.±1° C. In certain embodiments, the tosylate salt displays weight loss in DSC of less than 1.0% from 30° C. to 200° C. In certain embodiments, the tosylate salt is anhydrous.

In certain embodiments, R⁻ is HSO₄⁻ (i.e., the salt is the sulfate salt).

Also provided is the solid compound

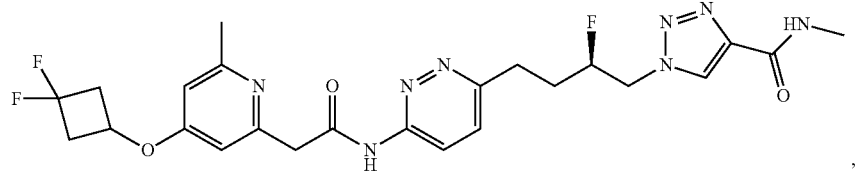

or a polymorph thereof. In certain embodiments, the compound or polymorph thereof is crystalline.

In certain embodiments, the polymorph is Polymorph A.
In certain embodiments, the polymorph is Polymorph B.
In certain embodiments, the polymorph is Polymorph C.
In certain embodiments, the polymorph is Polymorph D.
Solid Polymorph D of the compound

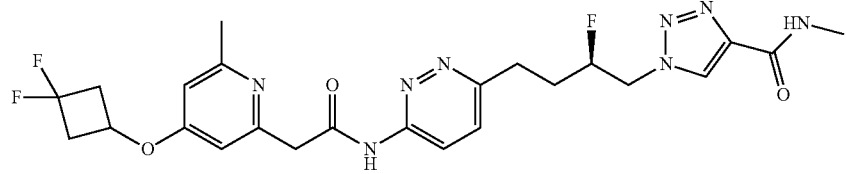 [SMILES: CNC(=O)c1cn(C[C@H](F)CCc2ccc(NC(=O)Cc3cc(OC4CC(F)(F)C4)cc(C)n3)nn2)nn1]

is provided herein.

In certain embodiments, Polymorph D is characterized as having one or more x-ray powder diffraction peaks chosen from about 4.0, about 8.0, about 11.6, about 11.9, about 14.9, about 15.9, about 17.6, about 19.9, about 20.2, about 22.4, about 23.7, and about 23.9 degrees 2-theta. In certain embodiments, Polymorph D has three or more of the peaks. In certain embodiments, Polymorph D has five or more of the peaks.

In certain embodiments, Polymorph D displays an endothermic peak in DSC with onset of 197° C.±1° C. In certain embodiments, Polymorph D is anhydrous. In certain embodiments, Polymorph D displays weight loss in DSC of less than 1% from 30° C. to 200° C.

Also provided is a composition comprising a compound, salt, solvate, or polymorph as recited herein, and a pharmaceutically acceptable carrier, adjuvant, or vehicle.

Also provided is a method of inhibiting GLS1 activity in a biological sample comprising contacting the biological sample with a compound, salt, solvate, or polymorph as recited herein.

Also provided is a method of treating a GLS1-mediated disorder in a subject in need thereof, comprising the step of administering to the subject a compound, salt, solvate, or polymorph as recited herein.

In certain embodiments, the subject is a human.

In certain embodiments, the GLS1-mediated disorder is chosen from cancer, immunological disorders, and neurological disorders.

In certain embodiments, the GLS1-mediated disorder is cancer.

In certain embodiments, the cancer is chosen from Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor, or a variant thereof.

Also provided herein is a method of treating a GLS1-mediated disorder in a subject in need thereof, comprising the sequential or co-administration of a compound, salt, solvate, or polymorph as recited herein, and another therapeutic agent.

In certain embodiments, the therapeutic agent is chosen from a taxane, inhibitor of bcr-abl, inhibitor of EGFR, DNA damaging agent, and antimetabolite.

In certain embodiments, the therapeutic agent is chosen from aminoglutethimide, amsacrine, anastrozole, asparaginase, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

In certain embodiments, the therapeutic agent is docetaxel.

In certain embodiments, the method further comprises administering non-chemical methods of cancer treatment.

In certain embodiments, the method further comprises administering radiation therapy.

In certain embodiments, the method further comprises administering surgery, thermoablation, focused ultrasound therapy, cryotherapy, or any combination thereof.

Also provided herein is a compound, salt, solvate, or polymorph as recited herein for use in human therapy.

Also provided herein is a compound, salt, solvate, or polymorph as recited herein for use in treating a GLS1-mediated disease.

Also provided herein is the use of a compound, salt, solvate, or polymorph as recited herein for the manufacture of a medicament to treat a GLS1-mediated disease.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B"

is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1 \ldots$ to $n_2$" or "between $n_1 \ldots$ and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

GLS1 inhibitor is used herein to refer to a compound that exhibits an IC50 with respect to GLS1 activity of no more than about 100 µM and more typically not more than about 50 µM, as measured in the GLS1 enzyme assay described generally herein below. IC50 is that concentration of inhibitor that reduces the activity of an enzyme (e.g., GLS1) to half-maximal level. Certain compounds disclosed herein have been discovered to exhibit inhibition against GLS1. In certain embodiments, compounds will exhibit an IC50 with respect to GLS1 of no more than about 10 µM; in further embodiments, compounds will exhibit an IC50 with respect to GLS1 of no more than about 5 µM; in yet further embodiments, compounds will exhibit an IC50 with respect to GLS1 of not more than about 1 µM; in yet further embodiments, compounds will exhibit an IC50 with respect to GLS1 of not more than about 200 nM, as measured in the GLS1 binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock (farm animals) such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate ($HSO_4^-$), butyrate, camphorate, camphorsulfonate, citrate, digluconate, formate, fumarate, gentisate, glutarate, glycerophosphate, glycolate, hemisulfate, heptanoate, hexanoate, hippurate, hydrochloride (HCl, chloride, $Cl^-$), hydrobromide (HBr, bromide, $Br^-$), hydroiodide (HI, iodide, $I^-$), 2-hydroxyethansulfonate (isethionate), lactate, maleate, malonate, DL-mandelate, mesitylenesulfonate, methanesulfonate (mesylate, MsOH, $MeSO_3H$, $CH_3SO_3H$, $CH_3SO_3^-$), naphthylenesulfonate, nicotinate, 2-naphthalenesulfonate, nitrate ($NO_3^-$), oxalate, pamoate, pectinate, persulfate, 3-phenylproprionate, phosphonate, picrate, pivalate, propionate, pyroglutamate, succinate, sulfate ($SO_4^{2-}$), sulfonate, tartrate, L-tartrate, trichloroacetate, trifluoroacetate, phosphate, glutamate, bicarbonate, para-toluenesulfonate (tosylate, TsOH, Ts, p-tosylate, methylbenzenesulfonate, 4-$MePhSO_3^-$), phenylsulfonate ($PhSO_3^-$), $HOSO_2CH_2CH_2SO_3^-$, $^-OSO_2CH_2CH_2SO_3^-$, and undecanoate. Acid addition salts can be named in terms of the acid used to form the salt, or the anion present in the salt. Thus, for example, the terms "chloride salt" and "hydrochloride salt" are understood to represent the same salt. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Compounds

The present disclosure provides the compound

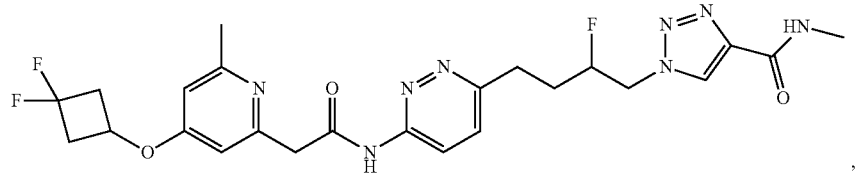

or a salt, solvate, or polymorph thereof.

Also provided is the compound

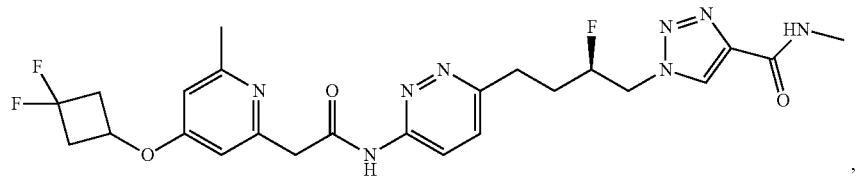 [SMILES: CNC(=O)c1cn(C[C@H](F)CCc2ccc(NC(=O)Cc3cc(OC4CC(F)(F)C4)cc(C)n3)nn2)nn1]

or a salt, solvate, or polymorph thereof.

Also provided is the compound
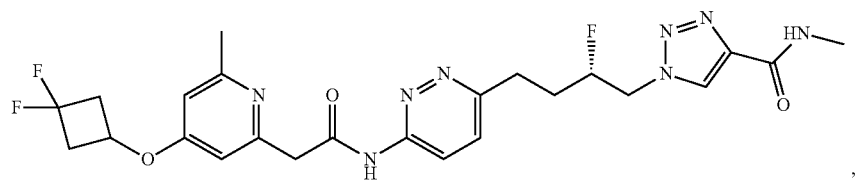 [SMILES: CNC(=O)c1cn(C[C@@H](F)CCc2ccc(NC(=O)Cc3cc(OC4CC(F)(F)C4)cc(C)n3)nn2)nn1]
or a salt, solvate, or polymorph thereof.
Also provided is a salt of structural Formula I, or an embodiment thereof, as disclosed herein.
In certain embodiments, the compound, salt, or polymorph thereof is chosen from:
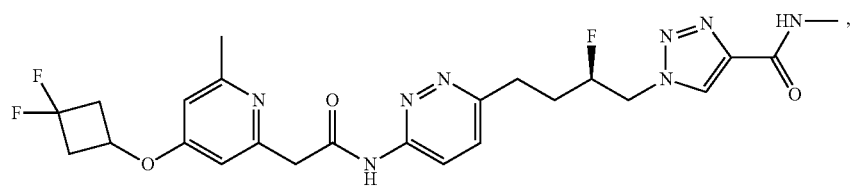
HCl
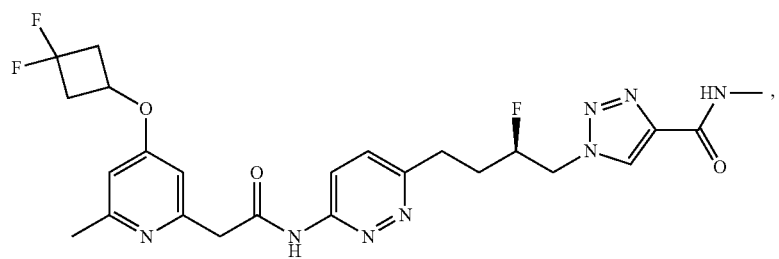
H₂SO₄
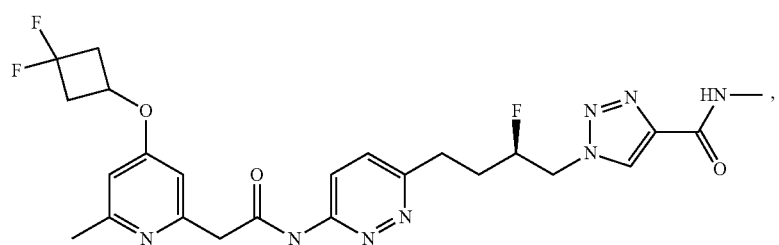
MeSO₃H
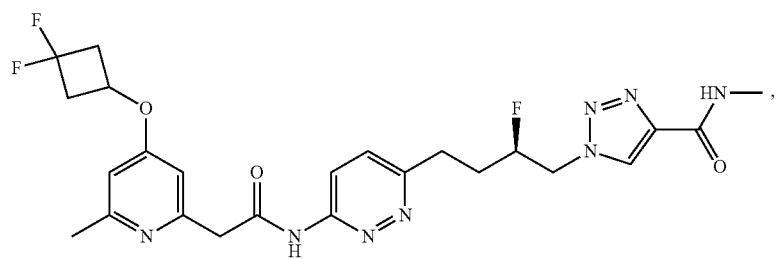
HBr

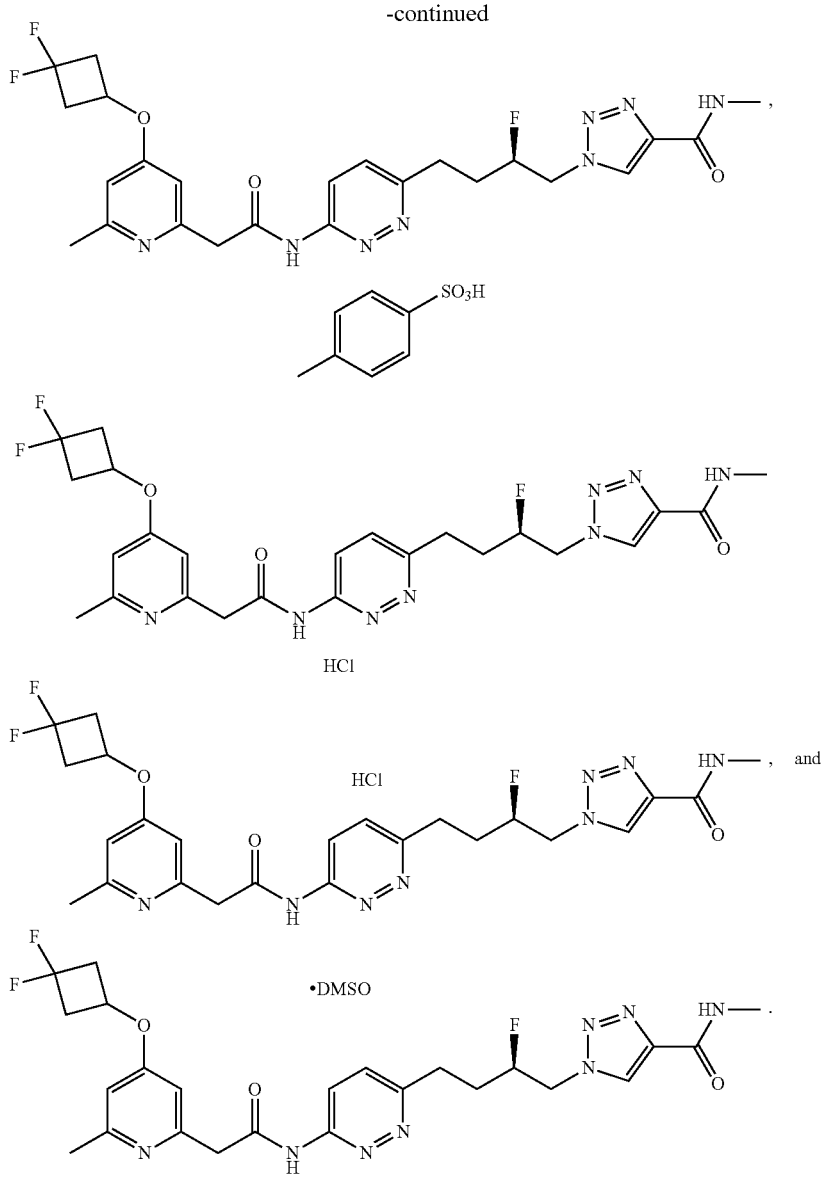

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Compounds described herein can be administered as follows:

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present invention may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Methods of Treatment

The present disclosure provides compounds and pharmaceutical compositions that inhibit glutaminase activity, particularly GLS1 activity and are thus useful in the treatment or prevention of disorders associated with GLS1. Compounds and pharmaceutical compositions of the present disclosure selectively modulate GLS1 and are thus useful in the treatment or prevention of a range of disorders associated with GLS1 and include, but are not limited to, cancer, immunological or neurological diseases associated with GLS1.

Neurological Disorders

In some embodiments, the compounds and pharmaceutical compositions of the present disclosure may be useful in the treatment or prevention of neurological diseases.

The most common neurotransmitter is glutamate, derived from the enzymatic conversion of glutamine via glutaminase. High levels of glutamate have been shown to be neurotoxic. Following traumatic insult to neuronal cells, there occurs a rise in neurotransmitter release, particularly glutamate. Accordingly, inhibition of glutaminase has been hypothesized as a means of treatment following an ischemic insult, such as stroke.

Huntington's disease is a progressive, fatal neurological condition. In genetic mouse models of Huntington's disease, it was observed that the early manifestation of the disease correlated with dysregulated glutamate release (Raymond et al., Neuroscience, 2011). In HIV-associated dementia, HIV infected macrophages exhibit upregulated glutaminase activity and increased glutamate release, leading to neuronal damage (Huang et al., J. Neurosci., 2011). Similarly, in another neurological disease, the activated microglia in Rett Syndrome release glutamate causing neuronal damage. The release of excess glutamate has been associated with the up-regulation of glutaminase (Maezawa et al., J. Neurosci, 2010). In mice bred to have reduced glutaminase levels, sensitivity to psychotic-stimulating drugs, such as amphetamines, was dramatically reduced, thus suggesting that glutaminase inhibition may be beneficial in the treatment of schizophrenia (Gaisler-Salomon et al., Neuropsychopharmacology, 2009). Bipolar disorder is a devastating illness that is marked by recurrent episodes of mania and depression. This disease is treated with mood stabilizers such as lithium and valproate; however, chronic use of these drugs appear to increase the abundance of glutamate receptors (Nanavati et al., J. Neurochem., 2011), which may lead to a decrease in the drug's effectiveness over time. Thus, an alternative treatment may be to reduce the amount of glutamate by inhibiting glutaminase. This may or may not be in conjunction with the mood stabilizers. Memantine, a partial antagonist of N-methyl-D-aspartate receptor (NMDAR), is an approved therapeutic in the treatment of Alzheimer's disease. Currently, research is being conducted looking at memantine as a means of treating vascular dementia and Parkinson's disease (Oliverares et al., Curr. Alzheimer Res., 2011). Since memantine has been shown to partially block the NMDA glutamate receptor also, it is not unresasonable to speculate that decreasing glutamate levels by inhibiting glutaminase could also treat Alzheimer's disease, vascular dementia and Parkinson's disease. Alzheimer's disease, bipolar disorder, HIV-associated dementia, Huntington's disease, ischemic insult, Parkinson's disease, schizophrenia, stroke, traumatic insult and vascular dementia are but a few of the neurological diseases that have been correlated to increased levels of glutamate. Thus, inhibiting glutaminase with a compound described herein can reduce or prevent neurological diseases. Therefore, in certain embodiments, the compounds may be used for the treatment or prevention of neurological diseases.

Immunological Disorders

In some embodiments, the compounds and pharmaceutical compositions of the present disclosure may be useful in the treatment or prevention of immunological diseases.

Activation of T lymphocytes induces cell growth, proliferation, and cytokine production, thereby placing energetic and biosynthetic demands on the cell. Glutamine serves as an amine group donor for nucleotide synthesis, and glutamate, the first component in glutamine metabolism, plays a direct role in amino acid and glutathione synthesis, as well as being able to enter the Krebs cycle for energy production (Carr et al., J. Immunol., 2010). Mitogen-induced T cell proliferation and cytokine production require high levels of glutamine metabolism, thus inhibiting glutaminase may serve as a means of immune modulation. In multiple sclerosis, an inflammatory autoimmune disease, the activated microglia exhibit up-regulated glutaminase and release increased levels of extracellular glutamate. Glutamine levels are lowered by sepsis, injury, burns, surgery and endurance exercise (Calder et al., Amino Acids, 1999). These situations put the individual at risk of immunosuppression. In fact, in general, glutaminase gene expression and enzyme activity are both increased during T cell activity. Patients given glutamine following bone marrow transplantation resulted in a lower level of infection and reduced graft v. host disease (Crowther, Proc. Nutr. Soc., 2009). T cell proliferation and activation is involved in many immunological diseases, such as inflammatory bowel disease, Crohn's disease, sepsis, psoriasis, arthritis (including rheumatoid arthritis), multiple sclerosis, graft v. host disease, infections, lupus and diabetes. In an embodiment of the invention, the compounds described herein can be used to treat or prevent immunological diseases.

Cancer

In some embodiments, the compounds and pharmaceutical compositions of the present disclosure may be useful in the treatment or prevention of cancer.

In addition to serving as the basic building blocks of protein synthesis, amino acids have been shown to contribute to many processes critical for growing and dividing cells, and this is particularly true for cancer cells. Nearly all definitions of cancer include reference to dysregulated proliferation. Numerous studies on glutamine metabolism in cancer indicate that many tumors are avid glutamine consumers (Souba, Ann. Surg., 1993; Collins et al., J. Cell. Physiol., 1998; Medina, J. Nutr., 2001; Shanware et al., J. Mol. Med., 2011). An embodiment of the invention is the use of the compounds described herein for the treatment of cancer.

In some embodiments, the compounds of the present disclosure may be used to prevent or treat cancer, wherein the cancer is one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia or Wilms Tumor.

In certain embodiments, the cancer to be treated is one specific to T-cells such as T-cell lymphomia and lymphblastic T-cell leukemia.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-cancer drugs, anti-proliferative drugs, and anti-inflammatory drugs.

GLS1 inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a GLS1 inhibitor compound, as described herein, in combination with another therapeutic agent. By way of example only, the therapeutic effectiveness of a GLS1 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a GLS1 inhibitor as described herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a GLS1 inhibitor is optionally used in combination with procedures that provide additional benefit to the patient. A GLS1 inhibitor and any additional therapies are optionally administered before, during or after the occurrence of a disease or condition, and the timing of administering the composition containing a GLS1 inhibitor varies in some embodiments. Thus, for example, a GLS1 inhibitor is used as a prophylactic and is administered continuously to subjects with a propensity to develop conditions or diseases in order to prevent the occurrence of the disease or condition. A GLS1 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A GLS1 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a GLS1 inhibitor may be optimally used together with one or more of the following non-limiting examples of anti-cancer agents:

1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);
2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;
3) antimitotics, which are often plant alkaloids and terpenoids, or derivatives thereof, including but not limited to taxanes such as docetaxel (TAXITERE) and paclitaxel (ABRAXANE, TAXOL); vinca alkaloids such as vincristine (ONCOVIN), vinblastine, vindesine, and vinorelbine (NAVELBINE);
4) topoisomerase inhibitors, including but not limited to camptothecin (CTP), irinotecan (CAMPTOSAR), topotecan (HYCAMTIN), teniposide (VUMON), and etoposide (EPOSIN);
5) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;
6) aromatase inhibitors, including but not limited to aminoglutethimide, anastrozole (ARIMIDEX), letrozole (FEMARA), vorozole (RIVIZOR), exemestane (AROMASIN);
7) angiogenesis inhibitors, including but not limited to genistein, sunitinib (SUTENT) and bevacizumab (AVASTIN);
8) anti-steroids and anti-androgens such as aminoglutethimide (CYTADREN), bicalutamide (CASODEX), cyproterone, flutamide (EULEXIN), nilutamide (NILANDRON);
9) tyrosine kinase inhibitors, including but not limited to imatinib (GLEEVEC), erlotinib (TARCEVA), lapatininb (TYKERB), sorafenib (NEXAVAR), and axitinib (INLYTA);
10) mTOR inhibitors such as everolimus, temsirolimus (TORISEL), and sirolimus;
11) monoclonal antibodies such as trastuzumab (HERCEPTIN) and rituximab (RITUXAN);
12) other agents, such as amsacrine; *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Where a subject is suffering from or at risk of suffering from an inflammatory condition, a GLS1 inhibitor compound described herein is optionally used together with one or more agents or methods for treating an inflammatory condition in any combination. Therapeutic agents/treatments for treating an autoimmune and/or inflammatory condition include, but are not limited to any of the following examples:
1) corticosteroids, including but not limited to cortisone, dexamethasone, and methylprednisolone;
2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);
3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);
4) CD20 blockers, including but not limited to rituximab (RITUXAN);
5) Tumor Necrosis Factor (TNF) blockers, including but not limited to etanercept (ENBREL), infliximab (REMICADE) and adalimumab (HUMIRA);
6) interleukin-1 receptor antagonists, including but not limited to anakinra (KINERET);
7) interleukin-6 inhibitors, including but not limited to tocilizumab (ACTEMRA);
8) interleukin-17 inhibitors, including but not limited to AIN457;
9) Janus kinase inhibitors, including but not limited to tasocitinib; and
10) syk inhibitors, including but not limited to fostamatinib.

Compound Synthesis

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; $Bu_3SnH$=tributyltin hydride; $CD_3OD$=deuterated methanol; $CDCl_3$=deuterated chloroform; CDI=1,1'-Carbonyldiimidazole; DAST=(diethylamino)sulfur trifluoride; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl) carbodiimide hydrochloride; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-PrOH=isopropanol; LAH=lithium aluminiumhydride; LDA=lithium diisopropyl amide; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; Pd(Ph$_3$)$_4$=tetrakis(triphenylphosphine)palladium(0); Pd$_2$(dba)$_3$=tris(dibenzylideneacetone)dipalladium(0); PdCl$_2$(PPh$_3$)$_2$=bis(triphenylphosphine)palladium(II) dichloride; PG=protecting group; prep-HPLC=preparative high-performance liquid chromatography; PMBCl=para-methoxybenzyl chloride; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TEA=Et$_3$N=triethylamine; TFA=trifluoroacetic acid; TFAA=trifluoroacetic anhydride; THF=tetrahydrofuran; Tol=toluene; TsCl=tosyl chloride; Xantphos=4,5-Bis(diphenylphosphino)-9,9-dimethylxanthene; X-Phos=2-dicyclohexylphosphino-2',4',6'-triisopropylbiphenyl.

General Methods for Preparing Compounds

The following schemes can be used to practice the present invention. Additional structural groups, including but not limited to those defined elsewhere in the specification and not shown in the compounds described in the schemes can be incorporated to give various compounds disclosed herein, or intermediate compounds which can, after further manipulations using techniques known to those skilled in the art, be converted to compounds of the present invention. For example in certain embodiments the A-ring in the structures described in the schemes—wherein A is a heteroaromatic ring—can be substituted with various groups as defined herein.

Non-limiting examples include the following compounds and pharmaceutically acceptable salts thereof.

EXAMPLE 1

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide Step 1: 3,6-diiodopyridazine A mixture of 3,6-dichloropyridazine (60.00 g, 402.7 mmol) and 55% aqueous hydrogen iodide solution (51.51 g, 402.7 mmol, 30.30 mL) was stirred at 90° C. for 12 h. Solid was isolated by filtration and then suspended in a sat. aq. NaHCO$_3$ solution (300 mL). Solid was isolated by filtration, washing with petroleum ether (2×200 mL), to give the title compound as a yellow solid, which was used without further purification (120.0 g, 90%). MS (ES$^+$) C$_4$H$_2$I$_2$N$_2$ requires: 332, found: 333 [M+H]+.

Step 2: di-tert-butyl 2-(6-iodopyridazin-3-yl)malonate

To a suspension of NaH (27.12 g, 678.0 mmol, 60% in mineral oil) in THF (750 mL) were added di-tert-butyl propanedioate (97.75 g, 452.0 mmol, 100.8 mL) and the mixture was stirred at 28° C. for 15 min. 3,6-diiodopyridazine (75.00 g, 225.99 mmol) was added, and the reaction mixture was stirred at reflux for 8 h. The reaction mixture was quenched with a sat. aq. NH$_4$Cl solution (500 mL) and extracted with 1:1 EtOAc/petroleum ether (3×500 mL). The combined organic layers were dried over Na$_2$SO$_4$, filtered and concentrated under reduced pressure. The residue was purified by SiO$_2$ gel chromatography (10:1 petroleum ether/EtOAc) to give the title compound as a white solid (83.00 g, 87%). MS (ES$^+$) C$_{15}$H$_{21}$IN$_2$O$_4$ requires: 420, found: 421 [M+H]$^+$.

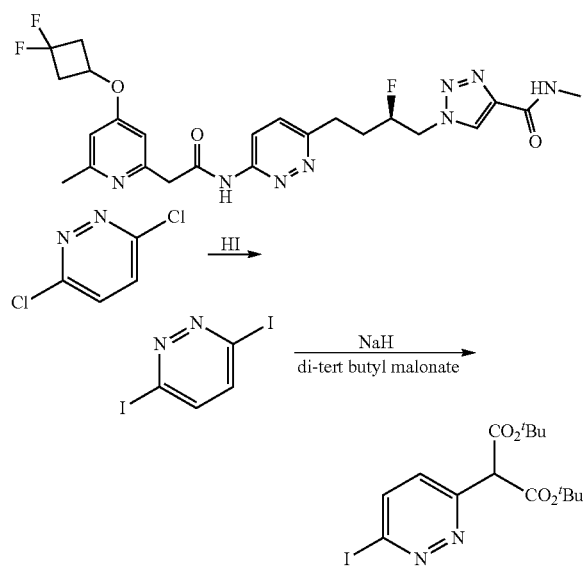

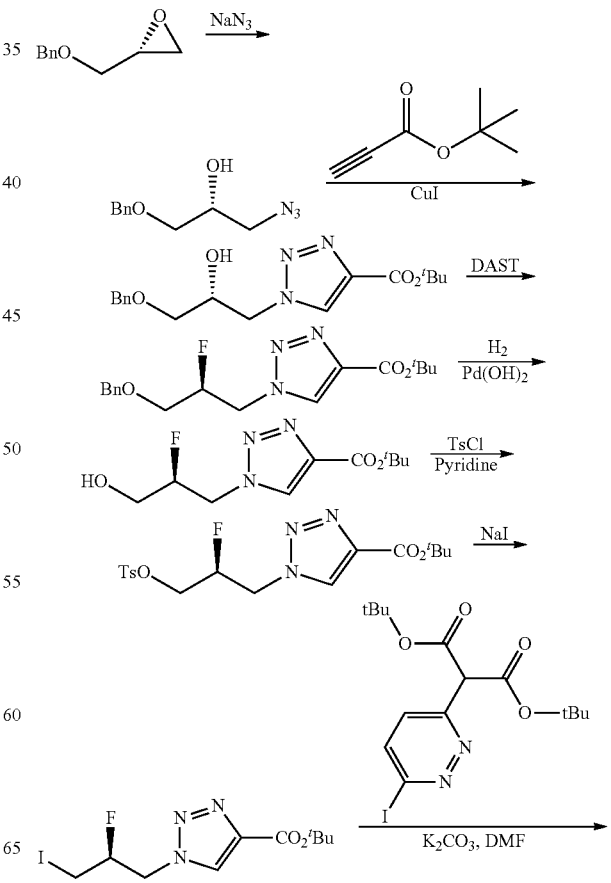

-continued

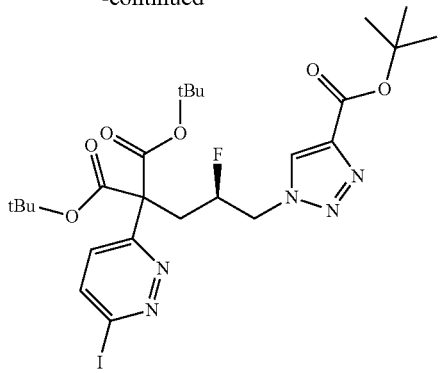

Step 3: (R)-1-azido-3-(benzyloxy)propan-2-ol

To a solution of (R)-2-((benzyloxy)methyl)oxirane (2.423 ml, 15.89 mmol) and NH$_4$Cl (1.70 g, 31.8 mmol) in MeOH (39.5 ml) and water (5.92 ml) was added sodium azide (5.17 g, 79.0 mmol) and the resulting mixture was stirred at RT overnight. The mixture was concentrated under reduced pressure and the residue was partitioned between EtOAc (50 mL) and water (60 mL). The two layers were separated, and the aqueous layer was extracted with EtOAc (3×50 mL). The organic layers were combined, dried over MgSO4, filtered, and concentrated under reduced pressure to give the title compound as a colorless oil (3.01 g, 91%). MS (ES$^+$) C$_{10}$H$_{13}$N$_3$O$_2$ requires: 207, found: 208 [M+H]$^+$.

Step 4: (R)-tert-butyl 1-(3-(benzyloxy)-2-hydroxypropyl)-1H-1,2,3-triazole-4-carboxylate To a solution of (R)-1-azido-3-(benzyloxy)propan-2-ol (3.01 g, 14.5 mmol), tert-butyl propiolate (2.393 ml, 17.43 mmol), DIEA (0.253 ml, 1.45 mmol), and AcOH (0.083 ml, 1.45 mmol) in DCM (58.1 ml) was added CuI (0.138 g, 0.726 mmol) and the resulting mixture was stirred at RT overnight. SiO$_2$ gel (10 g) was added to the stirring mixture and the resulting suspension was filtered and washed with DCM (20 mL) and EtOAc (20 mL). The filtrate was concentrated under reduced pressure to give crude title compound as an orange oil, which was used without further purification (3.95 g, 82%). MS (ES$^+$) C$_{17}$H$_{23}$N$_3$O$_4$ requires: 333. found: 334 [M+H]$^+$.

Step 5: (S)-tert-butyl 1-(3-(benzyloxy)-2-fluoropropyl)-1H-1,2,3-triazole-4-carboxylate To a 0° C. solution of (R)-tert-butyl 1-(3-(benzyloxy)-2-hydroxypropyl)-1H-1,2,3-triazole-4-carboxylate (3.95 g, 11.8 mmol) and pyridine (1.909 ml, 23.70 mmol) in DCM (23.70 ml) was added DAST (3.13 ml, 23.7 mmol). The resulting mixture was stirred at RT for 2.5 h, then filtered through a plug of SiO$_2$ gel, rinsing with DCM (50 mL). The filtrate was concentrated under reduced pressure and the residue was adsorbed onto Celite and purified by SiO$_2$ chromatography (0 to 50% EtOAc in hexanes) to give the title compound as a tan crystalline solid (1.781 g, 45% yield). MS (ES$^+$) C$_{17}$H$_{22}$FN$_3$O$_3$ requires: 335, found: 336 [M+H]+.

Step 6: (S)-tert-butyl 1-(2-fluoro-3-hydroxypropyl)-1H-1,2,3-triazole-4-carboxylate A reaction vessel was charged with (S)-tert-butyl 1-(3-(benzyloxy)-2-fluoropropyl)-1H-1,2,3-triazole-4-carboxy-late (1.78 g, 5.31 mmol) and EtOAc (53.1 ml) under an atmosphere of N$_2$. The solution was purged with N$_2$ for 10 min. and then with N$_2$ still flowing, Pd(OH)$_2$ on carbon (0.746 g, 1.06 mmol) was added. The resulting suspension was stirred as it was purged with H$_2$ for 2 min. The reaction mixture was stirred under an atmosphere of H$_2$ at 1 atm for 12 h, then purged with N$_2$, filtered through Celite and concentrated under reduced pressure to give the title compound as pale yellow crystals (1.32 g, 101% yield). MS (ES$^+$) C$_{10}$H$_{16}$FN$_3$O$_3$ requires: 245, found: 246 [M+H]$^+$.

Step 7: (S)-tert-butyl 1-(2-fluoro-3-(tosyloxy)propyl)-1H-1,2,3-triazole-4-carboxylate To a solution of (S)-tert-butyl 1-(2-fluoro-3-hydroxypropyl)-1H-1,2,3-triazole-4-carboxylate (1.32 g, 5.38 mmol) and DMAP (0.986 g, 8.07 mmol) in DCM (26.9 ml) was added 4-methylbenzene-1-sulfonyl chloride (1.23 g, 6.46 mmol) while the solution was maintained at RT by a water bath. The resulting mixture was stirred at RT for 1.5 h, then diluted with EtOAc (100 mL) and washed with sat. aq. NH$_4$Cl (2×40 mL). The organic layer was dried over MgSO$_4$, filtered and concentrated under reduced pressure to give the crude title compound, which was used without further purification (1.803 g, 84%). MS (ES$^+$) C$_{17}$H$_{22}$FN$_3$O$_5$S requires: 399, found: 400 [M+H]$^+$.

Step 8: (S)-tert-butyl 1-(2-fluoro-3-iodopropyl)-1H-1,2,3-triazole-4-carboxylate To a solution of (S)-tert-butyl 1-(2-fluoro-3-(tosyloxy)propyl)-1H-1,2,3-triazole-4-carboxylate (2.12 g, 5.31 mmol) in acetone (26.5 ml) was added sodium iodide (0.796 g, 5.31 mmol) and the resulting mixture was stirred at 80° C. for 3 h. Additional sodium iodide (1.6 g) was added and the mixture as stirred at 90° C. for 2 h. The mixture was allowed to cool to RT, then diluted with 1:1 EtOAc/hexanes (150 mL) and sequentially washed with H$_2$O (2×50 mL) and a sat. aq. NaCl solution (50 mL). The organic layer was dried over MgSO4, filtered, and concentrated under reduced pressure. The residue was adsorbed onto Celite and purified by SiO$_2$ gel chromatography (0 to 50% EtOAc/hexanes) to give the title compound as a white crystalline solid (1.71 g, 91%). MS (ES$^+$) C$_{10}$H$_{15}$FIN$_3$O$_2$ requires: 355, found: 356 [M+H]$^+$.

Step 9: (R)-di-tert-butyl 2-(3-(4-(tert-butoxycarbonyl)-1H-1,2,3-triazol-1-yl)-2-fluoropropyl)-2-(6-iodopyridazin-3-yl)malonate A mixture of potassium carbonate (0.412 g, 2.98 mmol), di-tert-butyl 2-(6-iodopyridazin-3-yl)malonate (1.25 g, 2.98 mmol), and (S)-tert-butyl 1-(2-fluoro-3-iodopropyl)-1H-1,2,3-triazole-4-carboxylate (1.00 g, 2.82 mmol) in a vial was degassed and then DMF (9.39 ml) was added. The mixture was degassed and backfilled with nitrogen for three cycles and then stirred for 80 hours at 25° C. The mixture was diluted with ethyl acetate and hexanes (1:1, 200 mL) and washed with water twice (100 mL+100 mL). The combined aqueous layer was extracted with ethyl acetate hexanes (1:1, 100 mL). The combined organic layer was concentrated, was added brine and the organic layer was concentrated under reduced pressure. The residue was purified by SiO$_2$ gel chromatography (5 to 60% EtOAc in hexanes) to give the title compound (1.36 g, 74.6% yield) as a yellow liquid. MS (ES+) C$_{25}$H$_{35}$FIN$_5$O$_6$ requires: 647, found: 648 [M+H]$^+$.

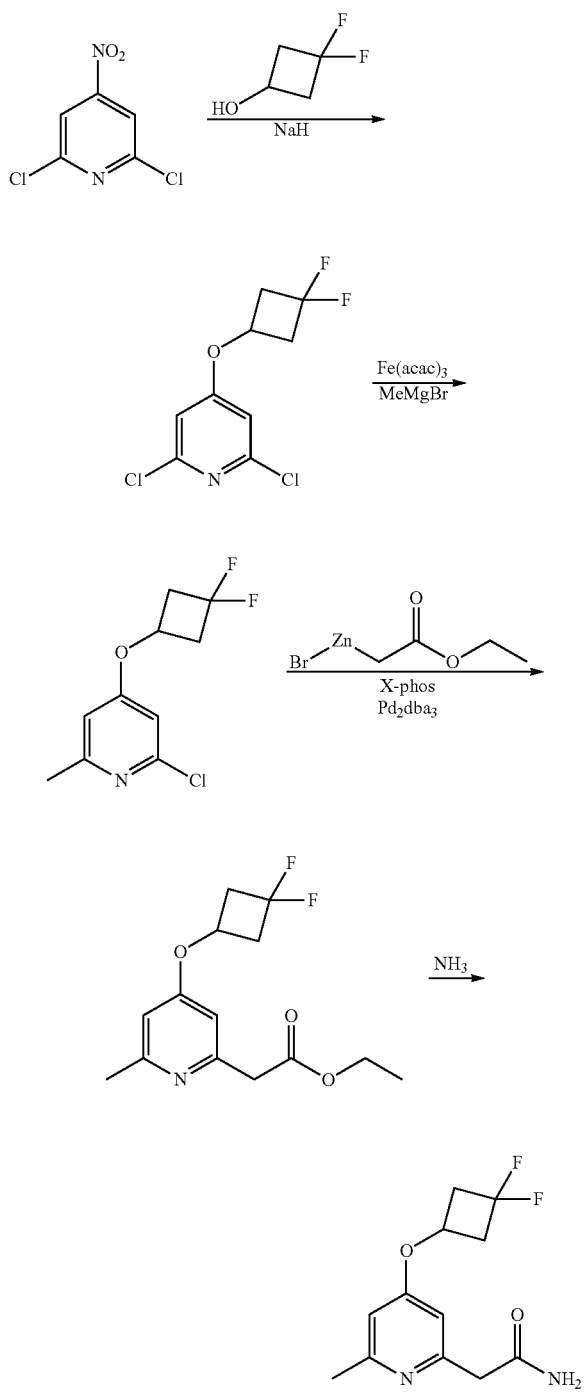

Step 10: 2,6-dichloro-4-(3,3-difluorocyclobutoxy)pyridine

To a suspension of NaH (8.88 g, 60% in mineral oil, 222 mmol) in THF (800 ml) at 0° C. was added 3,3-difluorocyclobutanol (20 g, 185 mmol) dropwise over a period of 10 min. Right after the completion of addition (bubbling should have quickly stopped), 2,6-dichloro-4-nitropyridine (35.7 g, 185 mmol) was added portionwise and the resulting mixture was stirred at 0° C. for 1 h. Sat. aq. NH$_4$Cl (200 mL) and water (800 ml) were added, and the layers were separated. The aqueous phase was extracted with EtOAc (3×500 mL), and the combined organic layers were washed with sat. aq. NaCl, dried over MgSO$_4$, filtered and concentrated under reduced pressure. The residue was purified by SiO$_2$ gel chromatography (0 to 8% EtOAc in hexanes) to give the title compound as a white crystalline solid (45.0 g, 96%). MS (ES$^+$) C$_9$H$_7$Cl$_2$F$_2$NO requires: 253, found: 254 [M+H]$^+$.

Step 11: 2-chloro-4-(3,3-difluorocyclobutoxy)-6-methylpyridine

To a solution of 2,6-dichloro-4-(3,3-difluorocyclobutoxy)pyridine (45 g, 177 mmol), THF (800 ml), NMP (200 ml) and ferric acetylacetonate (1.877 g, 5.31 mmol) at 0° C. was added dropwise methylmagnesium bromide (3 M in ether, 77 ml, 230 mmol) and the resulting mixture was stirred at 0° C. for 0.5 h. The reaction was quenched with sat. aq. NH$_4$Cl (100 mL) at 0° C., water (900 ml) was added, and the layers were separated. The aqueous phase was extracted with EtOAc (3×500 mL), and the combined organic layers were washed with sat. aq. NaCl, dried over MgSO$_4$, filtered and concentrated under reduced pressure. The residue was purified by SiO$_2$ gel chromatography (0 to 20% EtOAc in hexanes) to give the title compound as a colorless liquid (36.5 g, 88%). MS (ES$^+$) C$_{10}$H$_{10}$ClF$_2$NO requires: 233, found: 234 [M+H]+.

Step 12: ethyl 2-(4-(3,3-difluorocyclobutoxy)-6-methylpyridin-2-yl)acetate

A degassed solution of 2-chloro-4-(3,3-difluorocyclobutoxy)-6-methylpyridine (33.0 g, 141 mmol), (2-ethoxy-2-oxoethyl)zinc(II) bromide (0.5 M in THF, 706 ml, 353 mmol), Pd2(dba)3 (6.47 g, 7.06 mmol) and XPhos (3.37 g, 7.06 mmol) was stirred at 50° C. for 1 h. The reaction mixture was allowed to cool to RT and sat. aq. NH$_4$Cl (100 mL) and water (900 mL) were added. Precipitate was removed by filtration, and the filtrate layers were separated. The aqueous phase was extracted with EtOAc (3×500 mL), and the combined organic layers were washed with sat. aq. NaCl, dried over MgSO$_4$, filtered and concentrated under reduced pressure. The residue was purified by SiO$_2$ gel chromatography (0 to 60% EtOAc in hexanes) to give the title compound as a yellow liquid (27.8 g, 69%). MS (ES$^+$) C$_{14}$H$_{17}$F$_2$NO$_3$ requires: 285, found: 286 [M+H]$^+$.

Step 13: 2-(4-(3,3-difluorocyclobutoxy)-6-methylpyridin-2-yl)acetamide

A solution of ethyl 2-(4-(3,3-difluorocyclobutoxy)-6-methylpyridin-2-yl)acetate (27.8 g, 97.0 mmol) and NH$_3$/MeOH (7 M, 557 ml, 3898 mmol) in a pressure bottle was stirred at 85° C. for 20 h. The reaction mixture was allowed to cool to RT, then concentrated under reduced pressure. The resulting solid was triturated with ether and isolated by filtration to give the title compound as an off-white solid (22.4 g, 90%). MS (ES$^+$) C$_{12}$H$_{14}$F$_2$N$_2$O$_2$ requires: 256, found: 257 [M+H]$^+$.

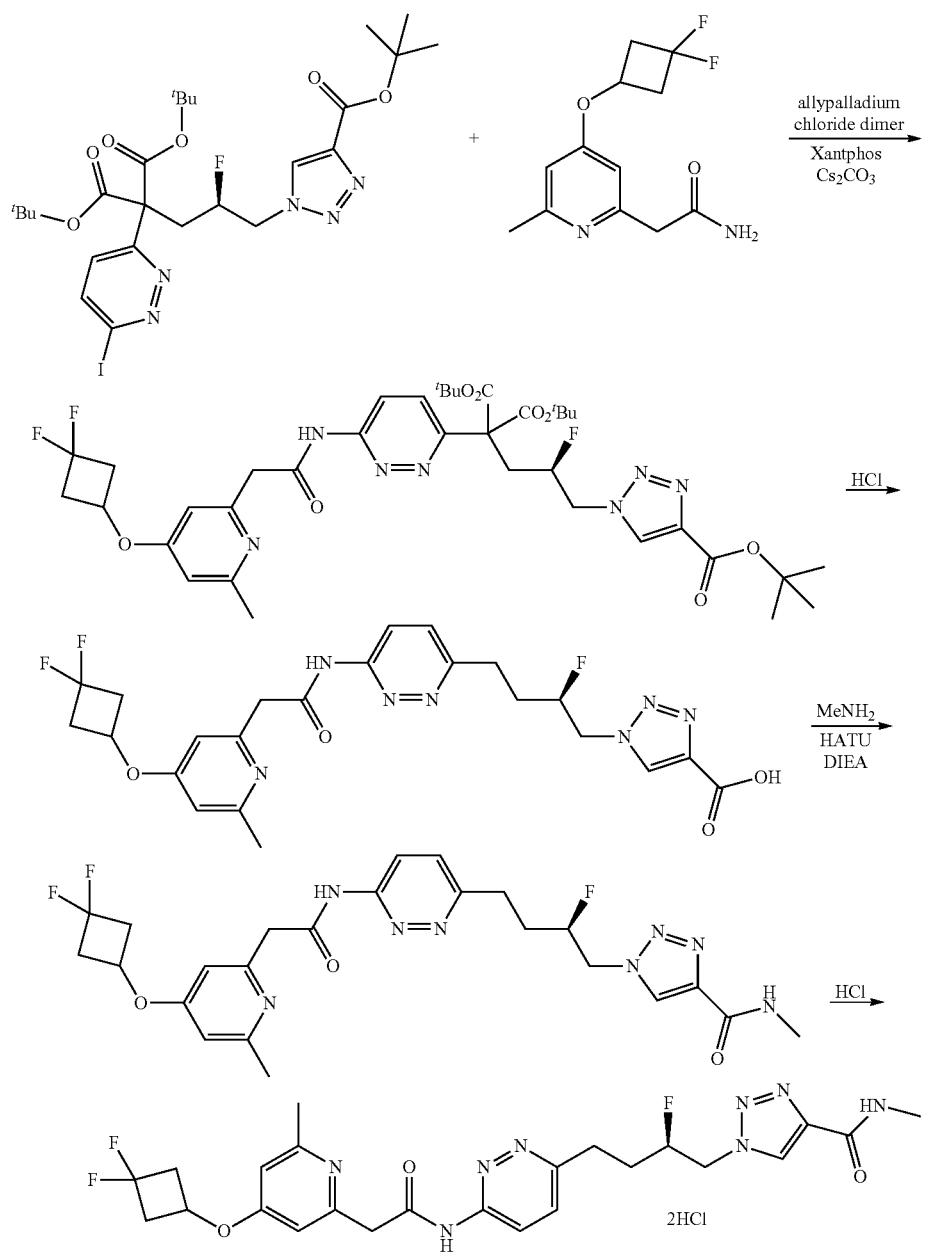

Step 14: di-tert-butyl (R)-2-(3-(4-(tert-butoxycarbonyl)-1H-1,2,3-triazol-1-yl)-2-fluoropropyl)-2-(6-(2-(4-(3,3-difluorocyclobutoxy)-6-methylpyridin-2-yl)acetamido)pyridazin-3-yl)malonate A degassed solution of (R)-di-tert-butyl 2-(3-(4-(tert-butoxycarbonyl)-1H-1,2,3-triazol-1-yl)-2-fluoropropyl)-2-(6-iodopyridazin-3-yl)malonate (42.4 g, 65.6 mmol), 2-(4-(3,3-difluorocyclobutoxy)-6-methylpyridin-2-yl)acetamide (14.0 g, 54.6 mmol), cesium carbonate (35.6 g, 109 mmol), Xantphos (6.32 g, 10.9 mmol) and allylpalladium chloride dimer (1.00 g, 2.73 mmol) in dioxane (300 ml) was stirred at 70° C. for 16 h. The reaction mixture was allowed to cool to RT, then filtered and the filtrate was concentrated under reduced pressure. The residue was purified by SiO$_2$ gel chromatography (0 to 3% MeOH in DCM) to give the title compound (36.5 g, 86%) as a foamy yellow solid. MS (ES$^+$) C$_{37}$H$_{48}$F$_3$N$_7$O$_8$ requires: 775, found: 776 [M+H]$^+$.

Step 15: (R)-1 (4 (6 (2 (4 (3,3-difluorocyclobutoxy)-6-methylpyridin-2-yl)acetamido) pyridazin-3-yl)-2-fluorobutyl)-1H-1,2,3-triazole-4-carboxylic acid A solution of (R)-di-tert-butyl 2-(3-(4-(tert-butoxycarbonyl)-1H-1,2,3-triazol-1-yl)-2-fluoropropyl)-2-(6-(2-(4-(3,3-difluorocyclobutoxy)-6-methylpyridin-2-yl)acetamido)pyridazin-3-yl)malonate (36.0 g, 46.4 mmol) in an HCl in dioxane solution (4.0 M, 696.0 ml, 2784 mmol) was stirred at 70° C. for 16 h. White precipitate formed. The reaction mixture was allowed to cool to RT. Precipitate was isolated by filtration, washed with EtOAc, and dried in vacuo to give the title compound as an off-white solid, which was used without further purification in the next step. MS (ES+) $C_{23}H_{24}F_3N_7O_4$ requires: 519, found: 520 [M+H]+.

Step 16: (R)-1 (4 (6 (2 (4 (3,3-difluorocyclobutoxy)-6-methylpyridin-2-yl)acetamido) pyridazin-3-yl)-2-fluorobutyl)-N-methyl-1H-1,2,3-triazole-4-carboxamide To a solution of crude (R)-1-(4-(6-(2-(4-(3,3-difluorocyclobutoxy)-6-methylpyridin-2-yl)acetamido)pyridazin-3-yl)-2-fluorobutyl)-1H-1,2,3-triazole-4-carboxylic acid hydrochloride prepared in the previous step (assumed 46.4 mmol) in DMF (200 ml) at 0° C. was added HATU (17.64 g, 46.4 mmol), DIEA (40.5 ml, 232 mmol) and methanamine in THF (2.0 M, 27.8 ml, 55.7 mmol) and the resulting mixture was stirred at 20° C. for 1 h. The volatiles were removed under reduced pressure. Water (1000 mL) and DCM (500 ml) were added, and the layers were separated. The aqueous phase was extracted with DCM (3×300 mL), the combined organic layers were washed with sat. aq. NaCl, dried over MgSO4, filtered and concentrated under reduced pressure. The residue was purified by SiO2 gel chromatography (0 to 8% MeOH in DCM) to give the title compound (16.8 g, 68.0% yield) as a white solid. MS (ES+) $C_{24}H_{27}F_3N_8O_3$ requires: 532, found: 533 [M+H]+. 1H NMR (DMSO-d6) δ 11.30 (s, 1 H), 8.51 (s, 1 H), 8.47 (q, J=4.4, 1 H), 8.22 (d, J=9.1 Hz, 1 H), 7.60 (d, J=9.3 Hz, 1 H), 6.79 (d, J=2.5 Hz, 1 H), 6.72 (d, J=2.5 Hz, 1 H), 5.09-4.96 (m, 1 H), 4.90-4.70 (m, 3 H), 3.87 (s, 2 H), 3.28-3.18 (m, 2 H), 3.08-2.98 (m, 2 H), 2.76 (d, J=4.9 Hz, 3 H), 2.75-2.63 (m, 2 H), 2.39 (s, 3H), 2.20-1.95 (m, 2 H).

Step 17: (R)-1 (4 (6 (2 (4 (3,3-difluorocyclobutoxy)-6-methylpyridin-2-yl)acetamido) pyridazin-3-yl)-2-fluorobutyl)-N-methyl-1H-1,2,3-triazole-4-carboxamide dihydrochloride To a solution of (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide (12.71 g, 23.87 mmol) in MeOH (20 ml) and DCM (60 ml) at 0° C. was added HCl in dioxane (4.0 M, 11.93 ml, 47.70 mmol) and the resulting mixture was stirred for 5 min. then concentrated under reduced pressure. The residue was redissolved in MeCN and water, lyophilized, and the resulting solid was triturated with EtOAc and dried in vacuo to give the title compound (14.03 g, 97%) as a white solid. MS (ES+) $C_{24}H_{27}F_3N_8O_3$ requires: 532, found: 533 [M+H]+. 1H NMR (DMSO-d6) δ 11.66 (s, 1 H), 8.53 (s, 1 H), 8.47 (q, J=5.3, 1 H), 8.23 (d, J=9.1 Hz, 1 H), 7.73 (d, J=9.5 Hz, 1 H), 7.44 (d, J=2.0 Hz, 1 H), 7.39 (d, J=2.0 Hz, 1 H), 4.96-5.11 (m, 2 H), 4.67-4.86 (m, 2 H), 4.36 (s, 2 H), 3.34 (m, 2 H), 3.07 (m, 2 H), 2.87 (m, 2 H), 2.76 (d, J=4.9 Hz, 3 H), 2.68 (s, 3 H), 2.24-1.95 (m, 2 H). The title compound (2 mg/mL, 10 μL per injection) was analyzed on a Shimadzu Prominence HPLC system with a Lux Cellulose 4 column (4.6× 150 millimeter, 5 micrometer, 1 mL/min) using a mobile phase of water: acetonitrile (50:50), and showed an ee of >98%. Retention time: 11.3 mins.

Example 1 disclosed above may also be made by Scheme 2.

SCHEME 2:

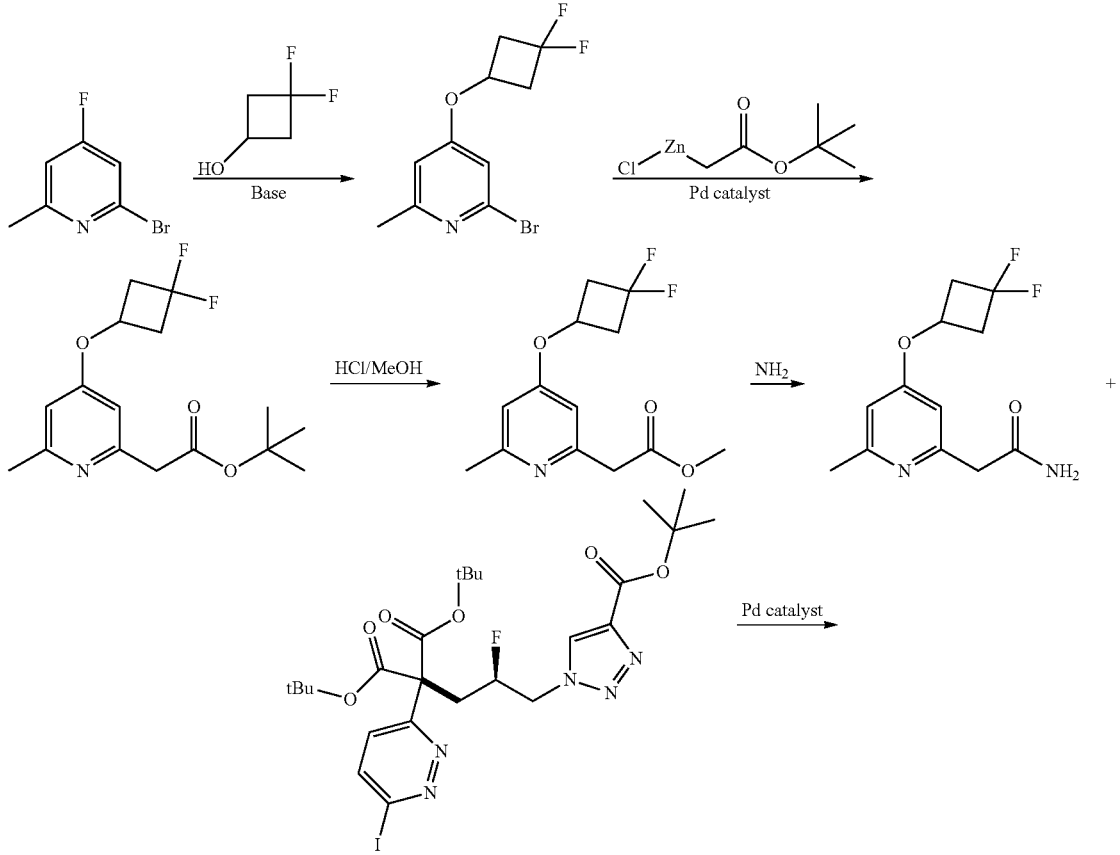

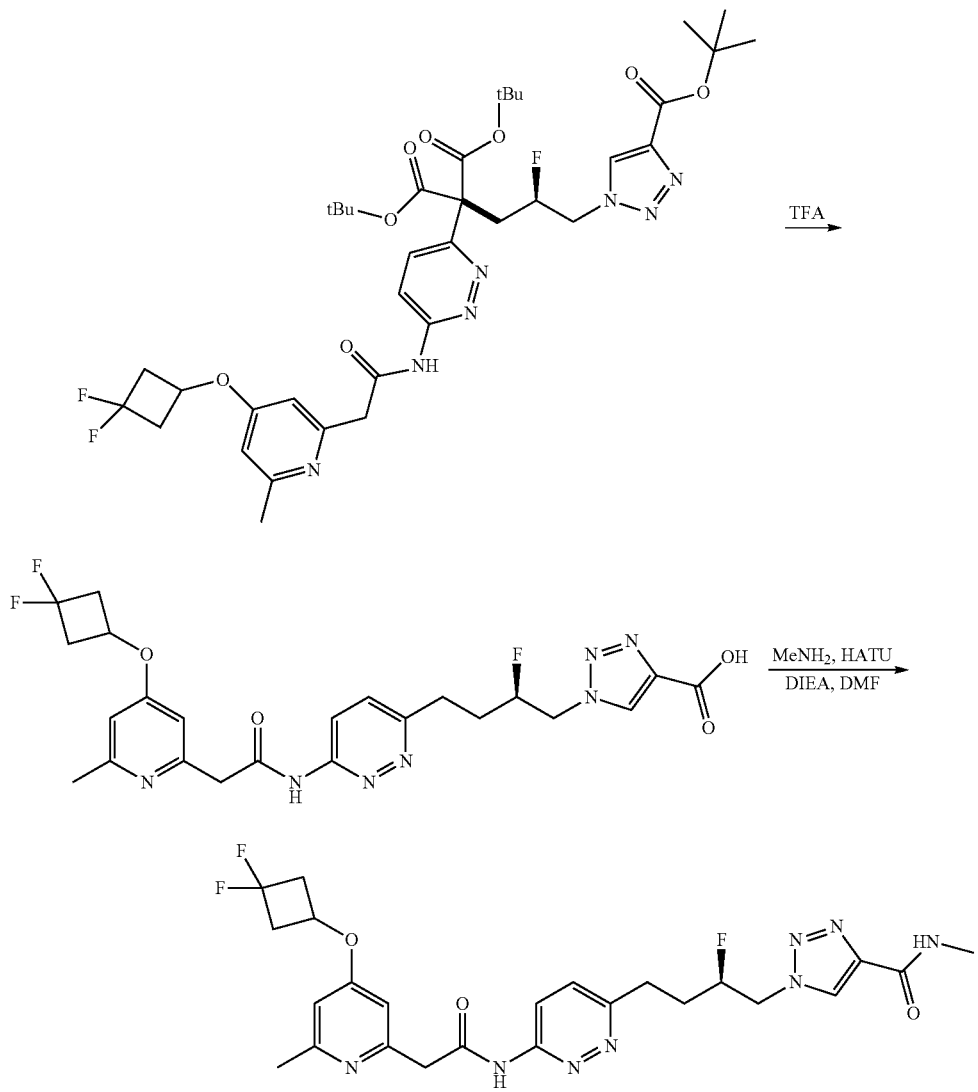

EXAMPLE 2

(S)-1-(4-(6-(2-(4-(3,3-difluorocyclobutoxy)-6-methylpyridin-2-yl)acetamido) pyridazin-3-yl)-2-fluorobutyl)-N-methyl-1H-1,2,3-triazole-4-carboxamide dihydrochloride

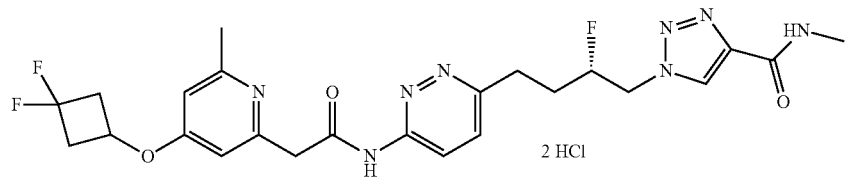 [SMILES: CNC(=O)c1cn(C[C@@H](F)CCc2ccc(NC(=O)Cc3cc(OC4CC(F)(F)C4)cc(C)n3)nn2)nn1]

Made in the same fashion as Example 1. MS (ES⁺) $C_{24}H_{27}F_3N_8O_3$ requires: 532, found: 533 [M+H]+. The title compound (2 mg/mL, 10 µL per injection) was analyzed on a Shimadzu Prominence HPLC system with a Lux Cellulose 4 column (4.6×150 millimeter, 5 micrometer, 1 mL/min) using a mobile phase of water: acetonitrile (50:50), and showed an ee of >98%. Retention time: 9.3 mins.

EXAMPLE 3

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide hydrochloride

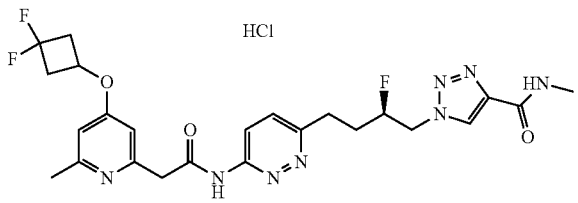 [SMILES: CNC(=O)c1cn(C[C@H](F)CCc2ccc(NC(=O)Cc3cc(OC4CC(F)(F)C4)cc(C)n3)nn2)nn1 ; Cl]

To a solution of (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide (20 mg, 0.038 mmol) in dioxane (1.8 mL) at RT was added aqueous HCl (37.6 µl, 0.038 mmol, 1.00 M) drop wise. A whitish precipitate formed immediately. The resulting mixture was stirred at RT for 15 min. The mixture was diluted with Et$_2$O (1.8 mL), cooled to 0° C., and the supernatant removed. The remaining solid was diluted with water (2 mL) to form a clear solution and lyophilized to obtain the title compound as a white solid (19 mg, 89%). MS (ES+) $C_{24}H_{27}F_3N_8O_3$·HCl requires: 532, found: 533 [M+H]$^+$. $^1$H NMR (600 MHz, DMSO-d$_6$) δ 15.20 (br s, 1H), 11.55 (s, 1H), 8.52 (s, 1H), 8.50-8.44 (m, 1H), 8.17 (d, J=9.1 Hz, 1H), 7.64 (d, J=9.2 Hz, 1H), 7.38 (d, J=21.5 Hz, 2H), 5.11-4.95 (m, 2H), 4.86-4.69 (m, 2H), 4.29 (s, 2H), 3.37-3.30 (m, 2H), 3.12-2.99 (m, 2H), 2.91-2.80 (m, 2H), 2.76 (d, J=4.5 Hz, 3H), 2.66 (s, 3H), 2.21-2.07 (m, 1H), 2.07-1.96 (m, 1H).

EXAMPLE 4

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide sulfate

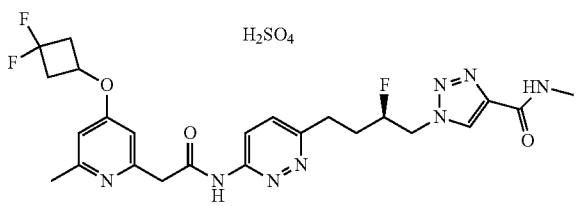 [SMILES: CNC(=O)c1cn(C[C@H](F)CCc2ccc(NC(=O)Cc3cc(OC4CC(F)(F)C4)cc(C)n3)nn2)nn1 ; "H2SO4"]

Prepared using the procedure in Example 3 to give the title compound as a white solid (89%). MS (ES+) $C_{24}H_{27}F_3N_8O_3$·H$_2$SO$_4$ requires: 532, found: 533 [M+H]+. $^1$H NMR (600 MHz, DMSO-d$_6$) δ 14.70 (br s, 1H), 11.55 (s, 1H), 8.52 (s, 1H), 8.50-8.43 (m, 1H), 8.17 (d, J=9.1 Hz, 1H), 7.65 (d, J=9.1 Hz, 1H), 7.39 (d, J=14.5 Hz, 2H), 5.12-4.95 (m, 2H), 4.87-4.70 (m, 2H), 4.24 (s, 2H), 3.39-3.28 (m, 2H), 3.11-2.99 (m, 2H), 2.92-2.81 (m, 2H), 2.76 (d, J=4.6 Hz, 3H), 2.65 (s, 3H), 2.22-2.08 (m, 1H), 2.08-1.92 (m, 1H).

EXAMPLE 5

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide methanesulfonate

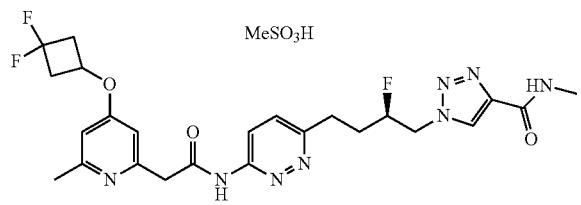 [SMILES: "MeSO3H" ; CNC(=O)c1cn(C[C@H](F)CCc2ccc(NC(=O)Cc3cc(OC4CC(F)(F)C4)cc(C)n3)nn2)nn1]

Prepared using the procedure in Example 3 using MeSO$_3$H (1.0 M in CH$_2$Cl$_2$) to give the title compound as a white solid (93%). MS (ES+) $C_{24}H_{27}F_3N_8O_3$·CH$_3$SO$_3$H requires: 532, found: 533 [M+H]+. $^1$H NMR (600 MHz, DMSO-d$_6$) δ 14.71 (br s, 1H), 11.53 (s, 1H), 8.52 (s, 1H), 8.50-8.44 (m, 1H), 8.17 (d, J=9.1 Hz, 1H), 7.64 (d, J=9.1 Hz, 1H), 7.34 (d, J=17.3 Hz, 2H), 5.12-4.96 (m, 2H), 4.86-4.68 (m, 2H), 4.21 (s, 2H), 3.34-3.28 (m, 2H), 3.10-3.00 (m, 2H), 2.91-2.80 (m, 2H), 2.76 (d, J=4.6 Hz, 3H), 2.63 (s, 3H), 2.30 (s, 3H), 2.21-2.07 (m, 1H), 2.07-1.94 (m, 1H).

EXAMPLE 6

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide hydrobromide

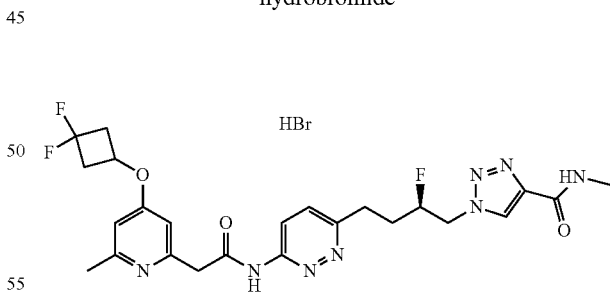

Prepared using the procedure in Example 3 to give the title compound as a white solid (87%). MS (ES+) $C_{24}H_{27}F_3N_8O_3$·HBr requires: 532, found: 533 [M+H]+. $^1$H NMR (600 MHz, DMSO-d$_6$) δ 14.76 (br s, 1H), 11.56 (s, 1H), 8.52 (s, 1H), 8.50-8.43 (m, 1H), 8.17 (d, J=9.2 Hz, 1H), 7.65 (d, J=9.2 Hz, 1H), 7.41 (d, J=15.7 Hz, 2H), 5.11-4.97 (m, 2H), 4.86-4.70 (m, 2H), 4.26 (s, 2H), 3.39-3.29 (m, 2H), 3.11-2.99 (m, 2H), 2.92-2.80 (m, 2H), 2.76 (dd, J=4.8, 1.2 Hz, 3H), 2.66 (s, 3H), 2.22-2.08 (m, 1H), 2.08-1.93 (m, 1H).

EXAMPLE 7

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide 4-methylbenzenesulfonate

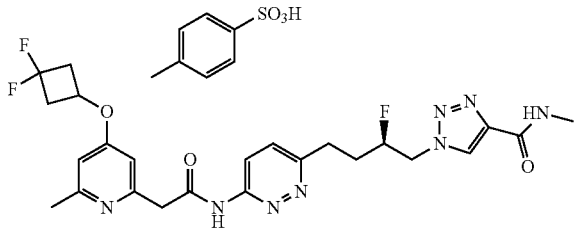 [SMILES: CNC(=O)c1cn(C[C@H](F)CCc2ccc(NC(=O)Cc3cc(OC4CC(F)(F)C4)cc(C)n3)nn2)nn1 ; Cc1ccc(S(=O)(=O)O)cc1]

Prepared using the procedure in Example A using aqueous TsOH (1.0 M) to give the title compound as a white solid (86%). MS (ES+) $C_{24}H_{27}F_3N_8O_3$·TsOH requires: 532, found: 533 [M+H]+. $^1$H NMR (600 MHz, DMSO-$d_6$) δ 14.69 (br s, 1H), 11.54 (s, 1H), 8.52 (s, 1H), 8.49-8.44 (m, 1H), 8.17 (d, J=9.1 Hz, 1H), 7.64 (d, J=9.1 Hz, 1H), 7.47 (d, J=8.0 Hz, 2H), 7.37 (d, J=15.9 Hz, 2H), 7.10 (dd, J=8.1, 1.0 Hz, 2H), 5.12-4.94 (m, 2H), 4.88-4.68 (m, 2H), 4.23 (s, 2H), 3.37-3.27 (m, 2H), 3.10-2.99 (m, 2H), 2.92-2.80 (m, 2H), 2.76 (d, J=4.7 Hz, 3H), 2.64 (s, 3H), 2.28 (s, 3H), 2.22-2.07 (m, 1H), 2.07-1.94 (m, 1H).

To obtain a crystalline solid, the title compound (5.0 mg) was stirred as a slurry in EtOH (200 uL) in a sealed vial for 48 h. The suspension initially dissolved and then slowly reformed small, needle-like crystals as observed under an optical microscope. The mixture was concentrated and the crystalline solid analyzed by HNMR, which was identical to the parent compound.

EXAMPLE 8

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide dihydrochloride

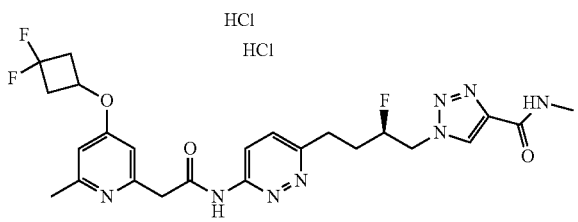 [SMILES: Cl ; CNC(=O)c1cn(C[C@H](F)CCc2ccc(NC(=O)Cc3cc(OC4CC(F)(F)C4)cc(C)n3)nn2)nn1 ; Cl]

To a solution of (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide (5.00 g, 9.39 mmol) in MeOH (5 mL) and DCM (15 mL) at 0° C. was added HCl (4.69 ml, 18.7 mmol, 4 M in dioxane) and the resulting mixture was stirred for 5 min. The volatiles were removed under reduced pressure. The residue was re-dissolved in MeCN and water and lyophilized to give the title compound (5.69 g, 100%) as a white solid. MS (ES+) $C_{24}H_{27}F_3N_8O_3$·2HCl requires: 532, found: 533 [M+H]+. $^1$H NMR (600 MHz, DMSO-$d_6$) δ 14.85 (br s, 1H), 11.55 (s, 1H), 8.52 (s, 1H), 8.47 (m, 1H), 8.17 (d, J=9.1 Hz, 1H), 7.64 (d, J=9.1 Hz, 1H), 7.39 (d, J=12.8 Hz, 2H), 5.11-4.97 (m, 2H), 4.85-4.71 (m, 2H), 4.25 (s, 2H), 3.38-3.29 (m, 2H), 3.10-3.00 (m, 2H), 2.91-2.81 (m, 2H), 2.76 (d, J=4.7 Hz, 3H), 2.65 (s, 3H), 2.20-1.96 (m, 2H).

EXAMPLE 9

Polymorphs of (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide

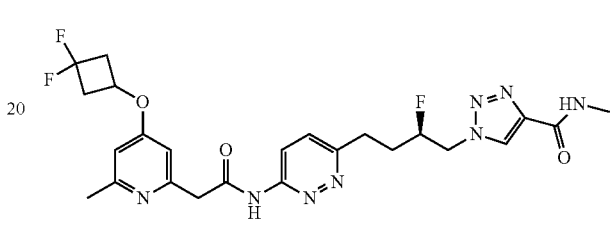

Polymorph A: The title compound (5.00 mg, 9.39 μmol) was suspended in 50 uL of 20% water in acetone (v/v), and the mixture was heated at 95° C. for 10 min. The suspension became a clear solution and the sample was left standing at RT to crystallize. The solids formed were observed under an optical microscope and found to be very fine, hair-like needles.

Polymorph B: The title compound (5.00 mg, 9.39 μmol) was suspended in 50 uL of 10% water in DMSO (v/v), and the mixture was heated at 95° C. for 10 min. The suspension became a clear solution and the sample was left standing at RT to crystallize. The solids formed were observed under an optical microscope and found to be rod-like crystals.

Polymorph C: The title compound (5.00 mg, 9.39 μmol) was suspended in 100 uL of 40% ethanol in anisole (v/v), and the mixture was heated at 95° C. for 10 min. The suspension became a clear solution and the sample was left standing at RT to crystallize. The solids formed were observed under an optical microscope and found to be fine, plate-like.

EXAMPLE 10

(R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide 1:1 DMSO solvate

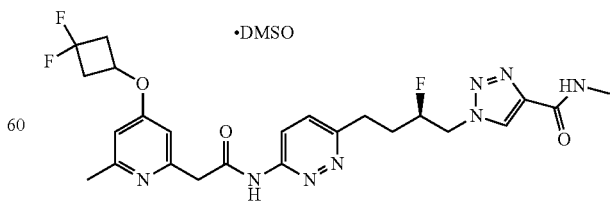

A suspension of (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide (100 mg, 0.188 mmol) in 1 mL of 15% water in DMSO (v/v) was heated at 95° C. for 1 min. The resulting clear solution was cooled to 80° C. and stirred for 10 min. The stirring was stopped and the mixture was allowed to cool by 10° C. every 20 min until the temperature reached 40° C. The mixture was then allowed to cool to RT overnight. The mixture was diluted with 1 mL of acetone, vortexed very briefly to breakdown the suspension, and filtered. The collected solids were rinsed with acetone (2×1 mL). The solid was dried under high vacuum overnight to obtain the title compound as a clear, crystalline solid (86 mg, 79%). This material appears as rod-like crystals under an optical microscope. MS (ES+) $C_{24}H_{27}F_3N_8O_3$.DMSO requires: 532, found: 533 [M+H]+.
$^1$H NMR (600 MHz, $CD_3OD$) δ 8.36 (d, J=9.1 Hz, 1 H), 8.34 (s, 1 H), 7.61 (d, J=9.2 Hz, 1 H), 6.79 (d, J=1.9 Hz, 1 H), 6.72 (d, J=1.9 Hz, 1 H), 4.90-5.15 (m, 1 H), 4.68-4.83 (m, 3 H), 3.91 (s, 2 H), 3.01-3.23 (m, 4 H), 2.92 (s, 3 H), 2.67-2.78 (m, 2 H), 2.65 (s, 6 H), 2.49 (s, 3 H), 2.24-1.99 (m, 2 H).

Physical Characterization of Example 1 Free Base and Salts

The Example 1 free base and salts were characterized by XRPD, DSC, TGA, PLM and DVS. The detailed procedures are listed below:

X-ray Powder Diffraction (XRPD) About 10 mg of test compound was weighed and distributed evenly onto a single crystal silicon plate. The sample was rotated at 10°/min. The diffraction pattern was measured with a with a Bruker D8 ADVANCE using a CuKα source (λ=1.54179 Å) operating at 40 KV of tube voltage and 40 mA of tube current. The scattering angle was scanned from 2θ=3° to 40° at a step rate of 10°/min.

Thermogravimetric Analysis (TGA) TGA was performed on a TA Instruments Q5000IR instrument. About 5 mg of test compound was weighed and transferred to an aluminum oxide crucible. The sample was heated from RT to 400° C. at a rate of 10° C./min under 50 mL/min $N_2$ purge.

Differential Scanning Calorimetry (DSC) DSC was performed on a TA Instruments Q2000 device. About 1 mg of test compound was weighed and transferred to a crimped aluminum pans with pinhole. The sample was heated from 30° C. to 400° C. at a rate of 10° C./min.

Polarized Light Microscope (PLM) An amount of the test compound as a powder was dispersed in silicone oil, and the morphology was examined with a Nikon LV100POL equipped with 5 megapixel CCD, 10× ocular lens, and objective lens chosen from 20× and 50×. The appropriate objective lens was chosen for the sample under examination.

Infrared Spectrometry (IR) was performed on a Thermo Nicolet 380 FT-IR spectrometer, using a DTGS detector with KBr windows and a Ge on KBr beamsplitter. 32 scans, having 4 cm$^{-1}$ resolution and with wavelength range of 4000 to 400 cm$^{-1}$ were collected and averaged.

High Performance Liquid Chromatography (HPLC) was run on an Agilent 1200 series HPLC instrument, equipped with a Amide_80, TSK_Gel (4.6 mm*150 mm, 3 μm) column. Mobile phase consisted of an 80:20 mix of solvent "A": solvent "B", wherein "A" was 85% $CH_3CN$: 15% aq $NH_4OAc$, and "B" was 10% $CH_3CN$: 90% aq $NH_4OAc$. Flow rate was 1.0 mL/min, at 25° C., for a total run time of 10 min. Detection was accomplished with an ELSD (SEDEX 85, 45° C., 3.5 bar, Nitrogen) detector.

$^1$H Nuclear Magnetic Resonance ($^1$H NMR) was recorded on a Bruker AVANCE III with manual phasing, pulse width 300 msec, acquisition time of 3.98 sec with 1 sec relaxation delay, time domain 24 K, 8 transients collected, and exponential multiplication of 0.5 for line broadening.

Dynamic Vapor Sorption (DVS) was examined with an SMS Advantage instrument. About 10 mg of sample was transferred into the instrument, and the weight change with respect to the atmospheric humidity at 25° C. was recorded accordingly, with the following parameters: Equilibrium: dm/dt: 0.01%/min. (for min: 10 min and max: 180 min); drying: 0% RH for 120 min; RH (%) measurement step: 10%; RH (%) measurement step scope: 0-90-0%.

As determined by XRPD, Example 1 free base was not fully crystalline and possibly contained partial amorphous content. PLM displayed birefringence phenomena and irregular block like shape. Also, DSC showed an endothermic peak with onset at 196° C. which was attributed to melting, An approximate 0.9% weight loss from 30° C. to 200° C. shown in TGA indicated that Example 1 free base is likely in anhydrous form.

EXAMPLE 11

Figure 3:
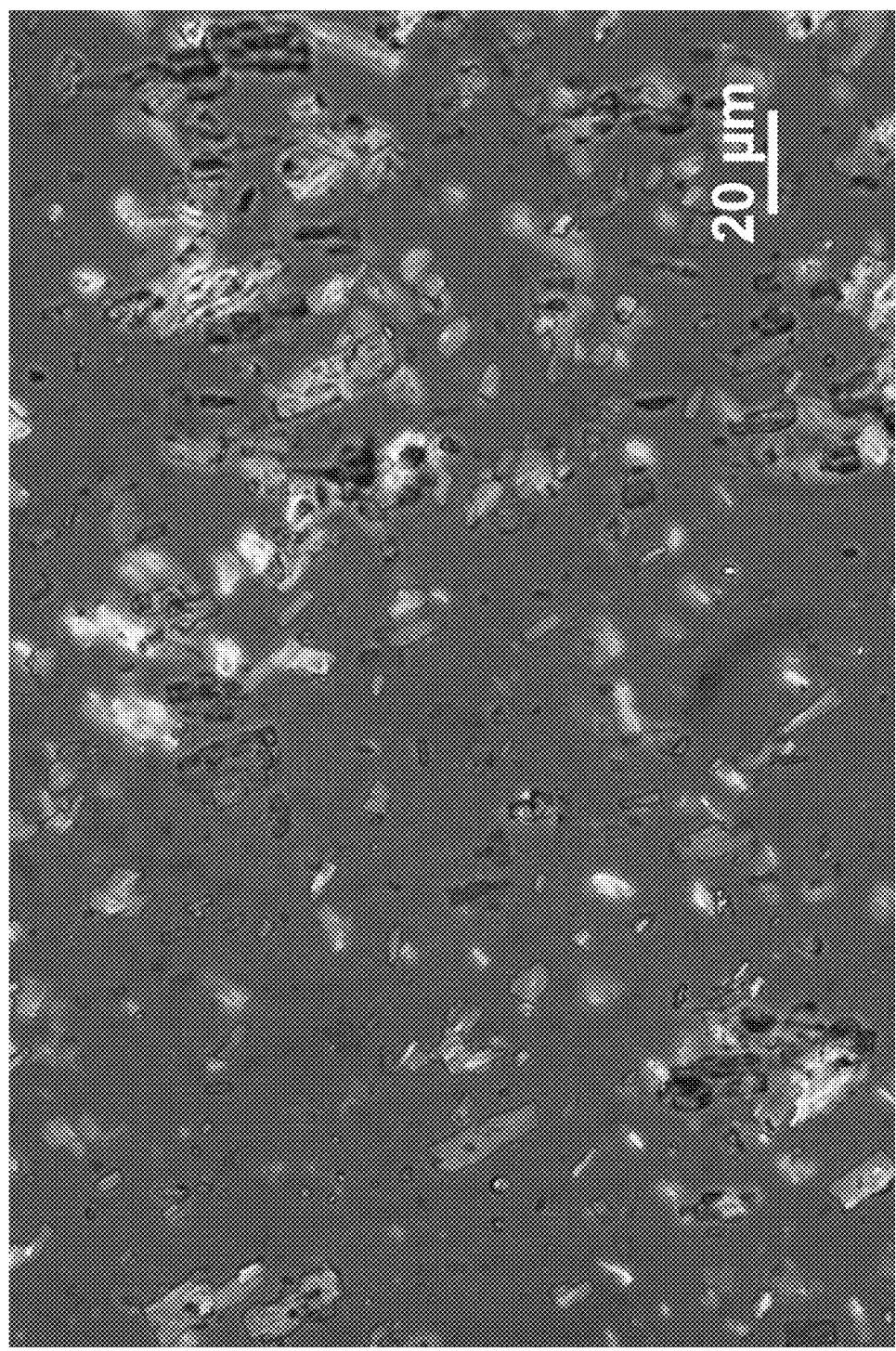
FIG. 3 depicts polarized light microscopy of Example 1 after recrystallization in acetone (Polymorph D).

Polymorph D of (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide A preliminary slurry test was conducted to purify the crystal form of Example 1 free base. About 30 mg of the title compound was weighed and transferred into a 2 mL glass vial. To the vial was added 1 mL of a selected solvent (acetone, acetonitrile, ethyl acetate, ethanol, methanol, 1:1 methanol:water, and tetrahydrofuran) to achieve a homogeneous suspension. The obtained suspension was agitated at 40° C. for 1 day on a thermomixer, then centrifuged at a speed of 10000 rpm. The supernatant was discarded to afford platelike crystals (FIG. 3).

Figure 2:
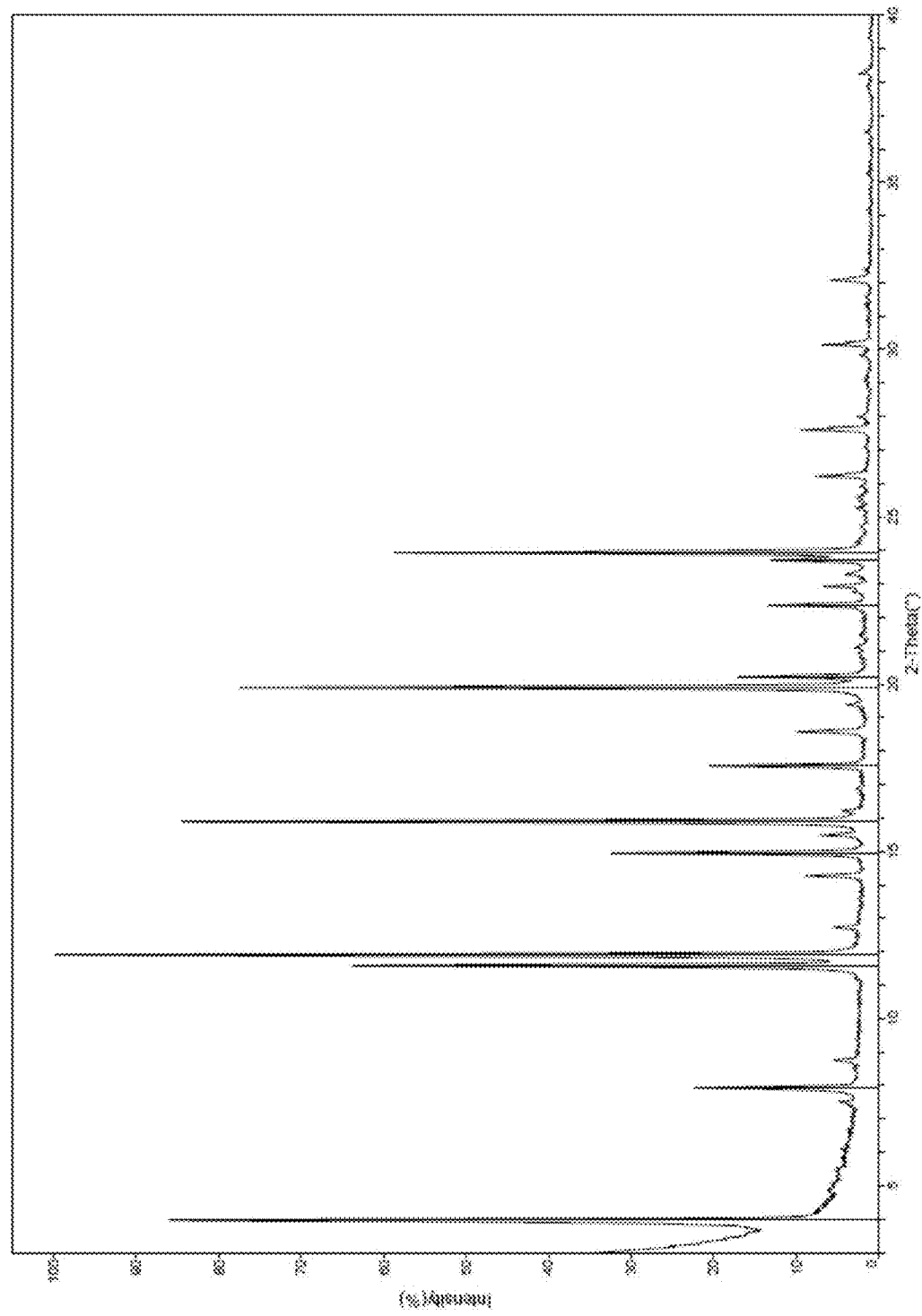
FIG. 2 is an XRPD of Example 1 after recrystallization in acetone (Polymorph D).
Figure 4:
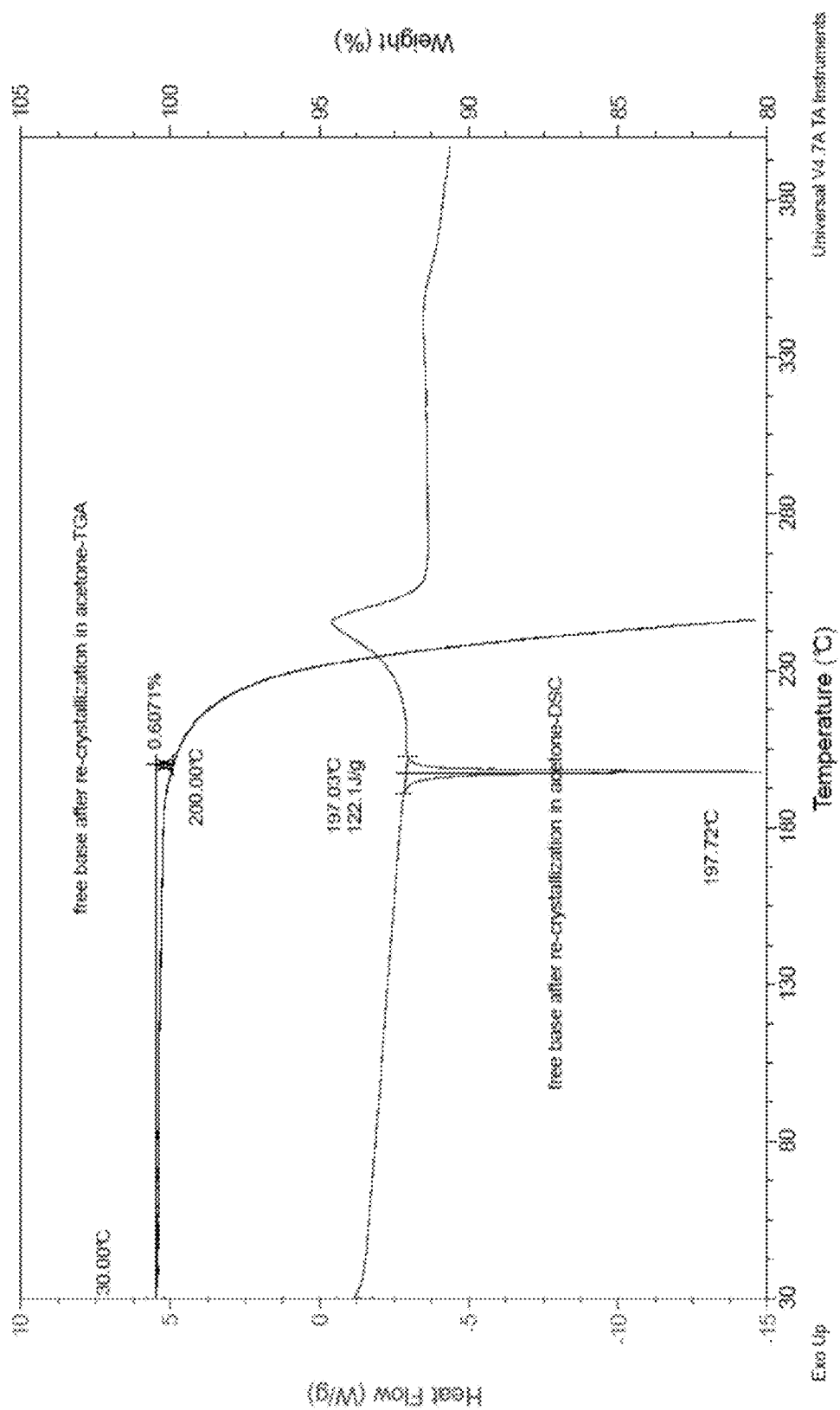
FIG. 4 depicts DSC and TGA behavior of Example 1 after purification in acetone (Polymorph D).
Figure 5:
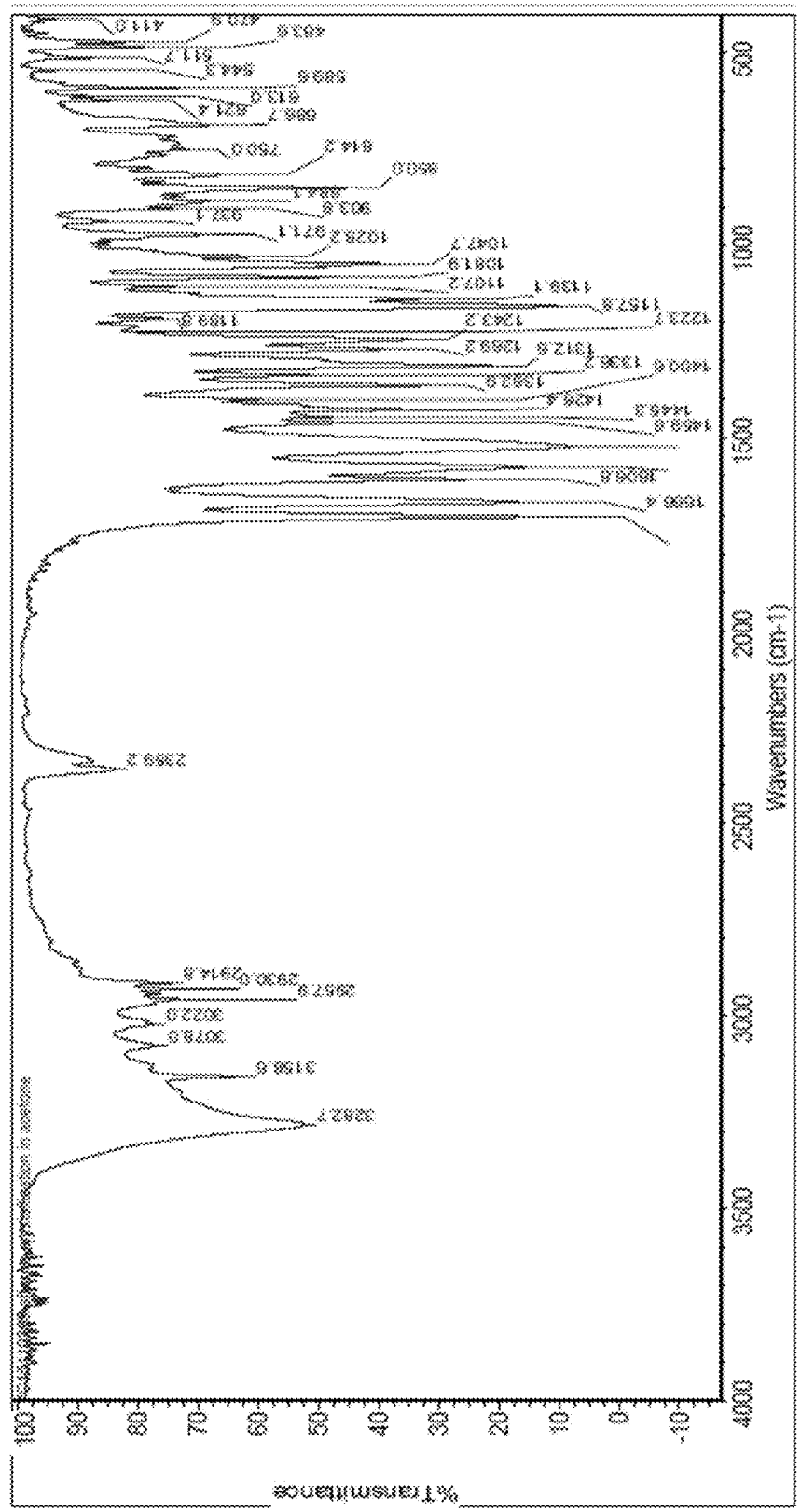
FIG. 5 displays the IR spectrum of purified free base Example 1 (Polymorph D).
Figure 6:
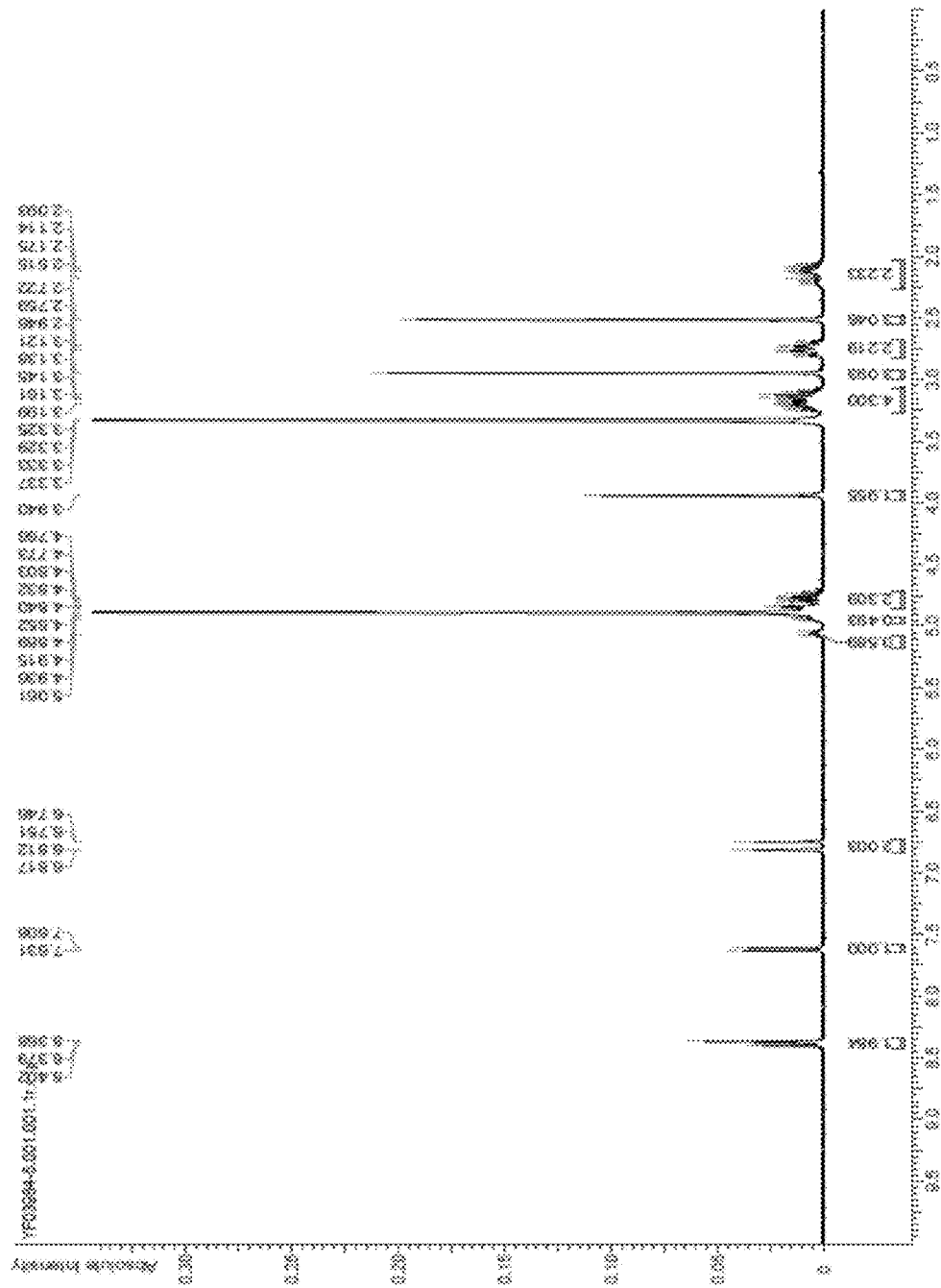
FIG. 6 displays the $^1$H NMR spectrum of purified free base Example 1 (Polymorph D).
Figure 10:
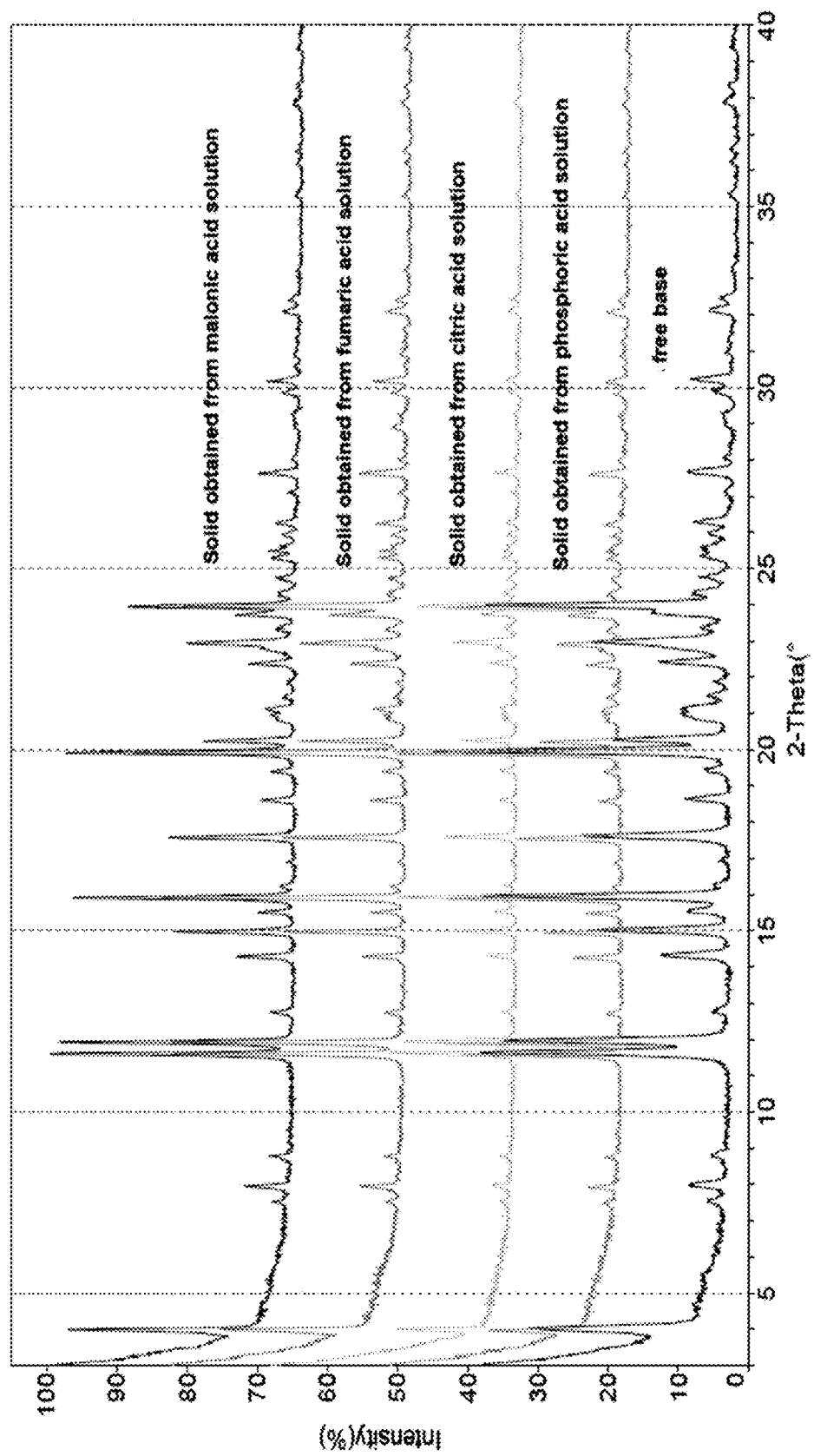
FIG. 10 is an overlay of the XRPD for additional salt candidates prepared by Method 1.

Based on the XRPD results (FIG. 1), the amorphous content was reduced via this purification procedure in most solvents, particularly in acetone (FIG. 2,). No obvious thermal dynamic change was found after recrystallization in acetone based on TGA-DSC profiles (FIG. 4), DSC showed a endothermic peak with onset at 197° C. which is attributed to melting. Loss of approximately 0.6% of from 30° C. to 200° C. shown in TGA indicated that Example 1 Polymorph D is likely in the anhydrous form. FIG. 5 displays the IR spectrum of Polymorph D. FIG. 10 displays the $^1$H NMR spectrum of Polymorph D.

$^1$H NMR (400 MHz, methanol-$d_4$) δ ppm 2.03-2.26 (m, 2 H), 2.51 (s, 3 H), 2.67-2.81 (m, 2 H), 2.95 (s, 3 H), 3.08-3.30 (m, 4 H), 3.94 (s, 2 H), 4.71-5.05 (m, 4 H), 6.75 (d, J=2.01 Hz, 1 H), 6.81 (d, J=2.01 Hz, 1 H), 7.62 (d, J=9.29 Hz, 1 H), 8.37 (s, 1 H), 8.39 (d, J=8.46 Hz, 1 H).

Provided herein is solid Example 1 (e.g. Polymorph D) characterized by having NMR peaks as disclosed above. In certain embodiments, solid Example 1 (e.g. Polymorph D) is characterized by having at least one, at least three, or at least five of the peaks as disclosed above. In certain embodiments, solid Example 1 (e.g. Polymorph D) is characterized by having between five and ten of the peaks as disclosed above. Such peaks may be referred to by their shift in parts per million.

Provided herein is solid Example 1 (e.g. Polymorph D) characterized by having one or more $^1$H nuclear magnetic resonance (NMR) chemical shifts at about 2.0-about 2.3, about 2.5, about 2.7-about 2.8, about 3.0, about 3.1-about 3.3, about 3.9, about 4.7-about 5.1, about 6.8, about 7.6, or about 8.4 parts per million. In certain embodiments, the solid Example 1 (e.g. Polymorph D) is characterized by having two, three, four, five, or more of the shifts. In certain embodiments, the solid Example 1 (e.g. Polymorph D) is characterized by having three or more of the shifts. In certain embodiments, the solid Example 1 (e.g. Polymorph D) is characterized by having five or more of the shifts.

Figure 7:
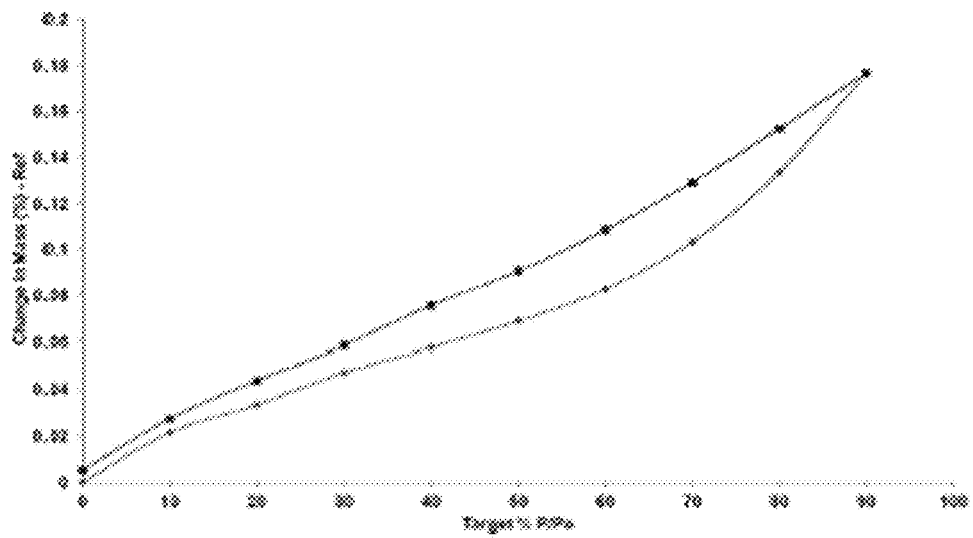
FIG. 7 depicts DVS of purified free base Example 1 (Polymorph D). The top graph depicts change in mass as a function of P/P$_0$ (the ordinate, "Change in Mass (%)—Ref", goes from 0 to 0.2 in increments of 0.02; the abscissa, "Target % P/P$_0$", from 0 to 100 in increments of 10). The bottom graph depicts change of mass as a function of time (the ordinate, "Change in Mass (%)—Ref", goes from 0 to 0.2 in increments of 0.02; the abscissa, "Time/mins", from 0 to 200 in increments of 20).
Figure 7:
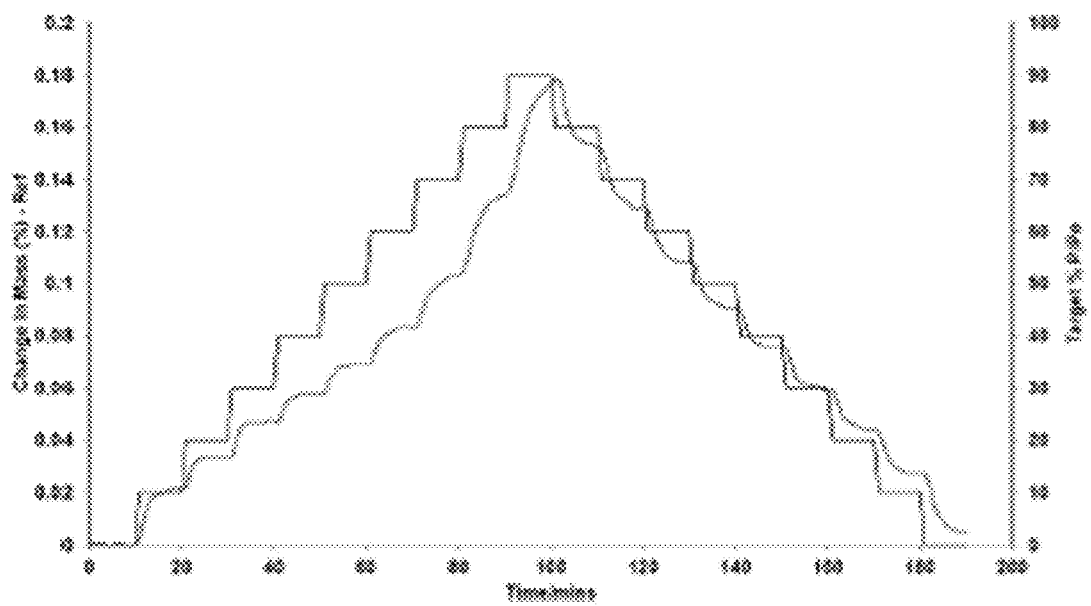
Figure 8:
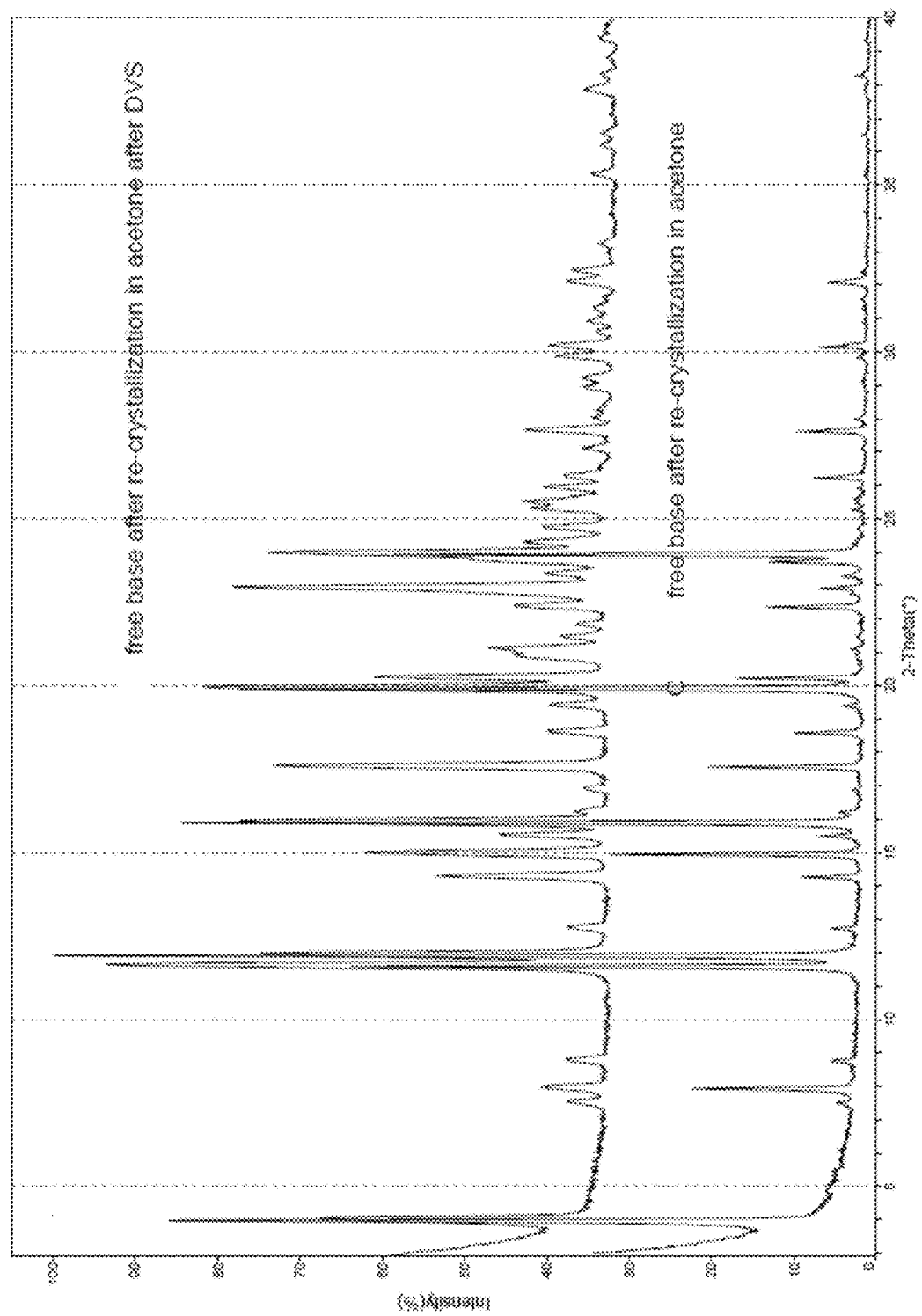
FIG. 8 is an overlay of the XRPD of Polymer D before and after DVS analysis.

The DVS result (FIG. 7 and Table 1) showed that Example 1 Polymorph D was non-hygroscopic with 0.1% water sorption from 0-80% RH, and no form transformation (FIG. 8) was found after DVS.

TABLE 1

DVS of purified free base Example 1 (Polymorph D).

| Target | Change of Mass | | |
|---|---|---|---|
| % $P/P_0$ | Sorption | Desorption | Hysteresis |
| 0 | 0.000 | 0.052 | |
| 10 | 0.0216 | 0.0276 | 0.0060 |
| 20 | 0.0336 | 0.0440 | 0.0104 |
| 30 | 0.0474 | 0.0587 | 0.0112 |
| 40 | 0.0578 | 0.0759 | 0.0181 |
| 50 | 0.0690 | 0.0906 | 0.0216 |
| 60 | 0.0828 | 0.1087 | 0.0259 |
| 70 | 0.1035 | 0.1294 | 0.0259 |
| 80 | 0.1337 | 0.1527 | 0.0190 |
| 90 | 0.1768 | 0.1768 | |

TABLE 2

XRPD of Polymorph D.

| 2-Theta | d(Å) | BG | Height | I % | Area | I % | FWHM |
|---|---|---|---|---|---|---|---|
| 3.967 | 22.2531 | 364 | 5375 | 82.4 | 39115 | 100.0 | 0.122 |
| 7.932 | 11.1367 | 179 | 1304 | 20.0 | 7483 | 19.1 | 0.096 |
| 11.584 | 7.6329 | 148 | 4108 | 63.0 | 22671 | 58.0 | 0.093 |
| 11.912 | 7.4234 | 154 | 6521 | 100.0 | 34719 | 88.8 | 0.089 |
| 14.956 | 5.9187 | 130 | 2025 | 31.1 | 9888 | 25.3 | 0.082 |
| 15.899 | 5.5696 | 126 | 5516 | 84.6 | 29798 | 76.2 | 0.091 |
| 17.561 | 5.0460 | 116 | 1238 | 19.0 | 5968 | 15.3 | 0.081 |
| 19.893 | 4.4594 | 109 | 5065 | 77.7 | 29715 | 76.0 | 0.098 |
| 20.222 | 4.3876 | 114 | 1009 | 15.5 | 6342 | 16.2 | 0.105 |
| 22.355 | 3.9736 | 110 | 780 | 12.0 | 4293 | 11.0 | 0.092 |
| 23.713 | 3.7490 | 111 | 748 | 11.5 | 6584 | 16.8 | 0.148 |
| 23.931 | 3.7154 | 107 | 3814 | 58.5 | 23368 | 59.7 | 0.103 |

Provided herein is solid Example 1 (e.g. Polymorph D) characterized by having XRPD peaks as disclosed above. In certain embodiments, solid Example 1 (e.g. Polymorph D) is characterized by having at least one, at least three, or at least five of the XRPD peaks as disclosed above. In certain embodiments, solid Example 1 (e.g. Polymorph D) is characterized by having between five and ten of the XRPD peaks as disclosed above. Such peaks may be referred to by their 2 theta shift.

Provided herein is solid Example 1 (e.g. polymorph D), characterized by having one or more X-ray powder diffraction peaks chosen from about 4.0, about 8.0, about 11.6, about 11.9, about 14.9, about 15.9, about 17.6, about 19.9, about 20.2, about 22.4, about 23.7, and about 23.9 degrees 2-theta. In certain embodiments, the Example 1 (e.g. polymorph D) is characterized by having two, three, four, five, or more of the peaks. In certain embodiments, the Example 1 (e.g. polymorph D) is characterized by having three or more of the peaks. In certain embodiments, the Example 1 (e.g. polymorph D) is characterized by having five or more of the peaks. Also provided is solid Example 1 (e.g. polymorph D), characterized by having a X-ray powder diffraction pattern as shown in FIG. 2.

Salt Preparation

Salt Preparation Method 1: The acids listed in Table 3 were selected to form salts with Example 1 in MeOH.

Step 1: Approximately 50 mg of Example 1 free base was dissolved in a 8 mL glass vial with 5 mL of MeOH to achieve a homogeneous suspension.

Step 2: An amount of solid acid was dissolved in a 8 mL glass vial with MeOH.

Step 3: A volume of acid solution sufficient to obtain a desired molar ratio of Example 1:acid (the volume of acid solutions added are listed in Table 3) was slowly titrated into the free base solution on the magnetic stirrer.

Step 4: The obtained liquid phase was stirred at room temperature for 24 hours to afford a precipitate, which was isolated by centrifugation.

The solid was analyzed with XRPD to determine if a new crystalline form was obtained, and then dried under vacuum at 40° C. overnight for further characterization. Example 1 and pure solid acid suspended in MeOH were used as XRPD standards.

Figure 9:
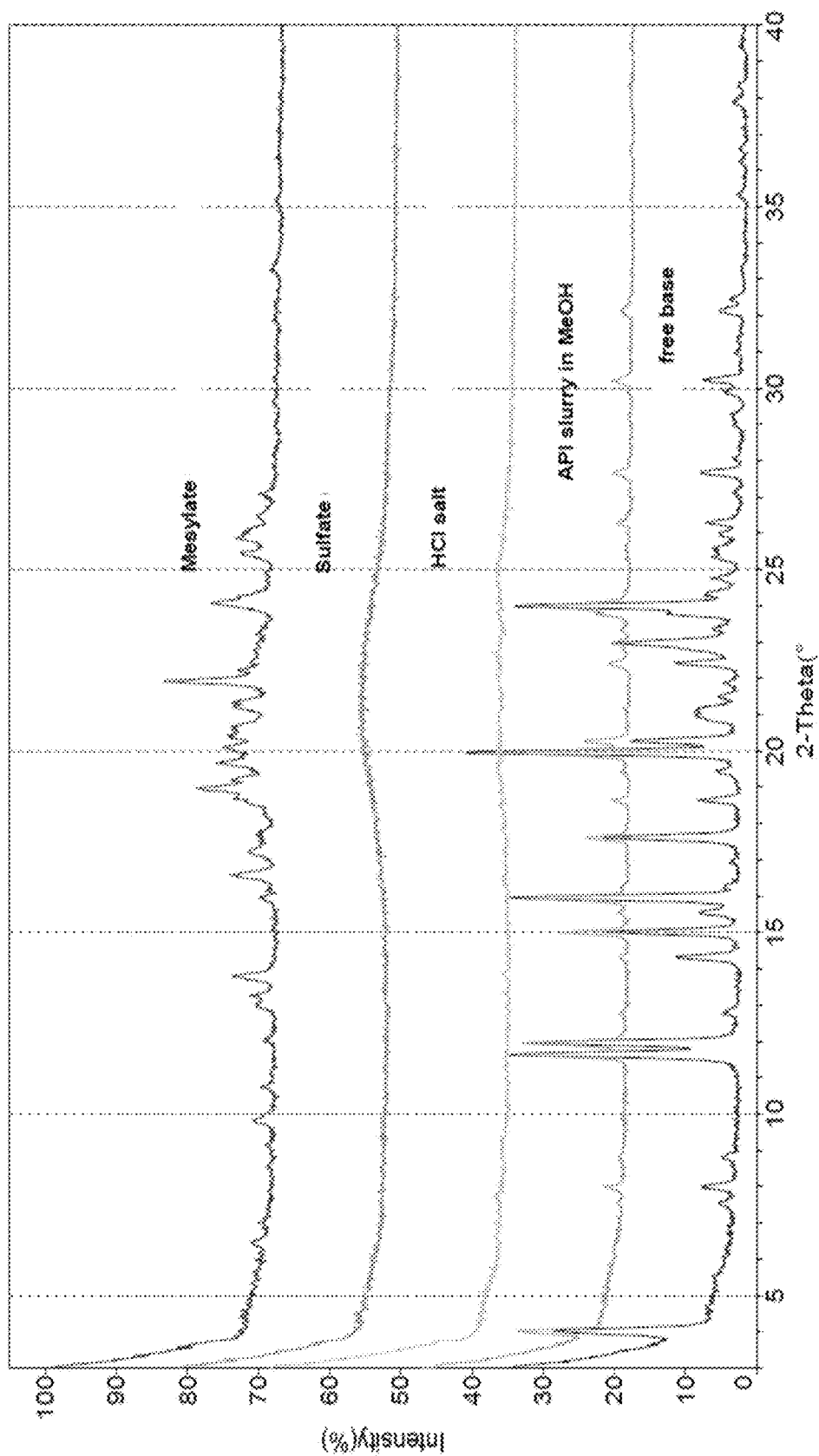
FIG. 9 is an overlay of the XRPD for salt candidates prepared by Method 1.

Results are disclosed in Table 3 and FIG. 9. Solids obtained from hydrochloric acid, sulfuric acid, and methanesulfonic acid showed different XRPD diffractograms compared with free base, suggesting the formation of chloride, sulfate, and mesylate salts, respectively. Use of acids selected from a different group afforded only free base, as determined by XRPD (FIG. 10).

TABLE 3

Salt preparation using Method 1.

| Acid | Molar Ratio | Acid solution concentration, mg/mL | Volume of acid solution | Observation | XRD pattern |
|---|---|---|---|---|---|
| HCl | 1:1 | 11.8 | 0.864 | Clear, and then 10 times of MTBE was added to produce precipitate | Amorphous |
| $H_2SO_4$ | 1:1 | 18.4 | 0.562 | Clear, and then 10 times of MTBE was added to produce precipitate | Amorphous |
| $H_3PO_4$ | 1:1 | 16.85 | 0.668 | No change | Free base |
| MsOH | 1:1 | 14.8 | 0.671 | Clear, and then 10 times of MTBE was added to produce precipitate | Poor crystalline |
| TsOH | 1:1 | 10 | 1.933 | Clear, and then 10 times of MTBE was added to produce precipitate, eventually redissolved | No solid |

TABLE 3-continued

Salt preparation using Method 1.

| Acid | Molar Ratio | Acid solution concentration, mg/mL | Volume of acid solution | Observation | XRD pattern |
|---|---|---|---|---|---|
| Citric acid | 1:1 | 10 | 2.171 | No change | Free base |
| Fumaric acid | 1:1 | 10 | 1.199 | No change | Free base |
| Malonic acid | 1:1 | 10 | 1.075 | No change | Free base |

Recrystallization of Method 1 Product: Potential salts (chloride, sulfate and mesylate) produced with Method 1 were recrystallized in several solvents in order to improve crystallinity.

About 2 mg of salt candidate was weighed into a 1.5 mL glass vial, and then 0.2 mL of solvent (EtOH, ACN, acetone, EtOAc and THF) was added. The obtained suspension was agitated at 40° C. for 1 day on a thermal mixer, then centrifuged at 10000 rpm. The resulting solid was dried under vacuum at 40° C. overnight for XRPD analysis.

Figure 11:
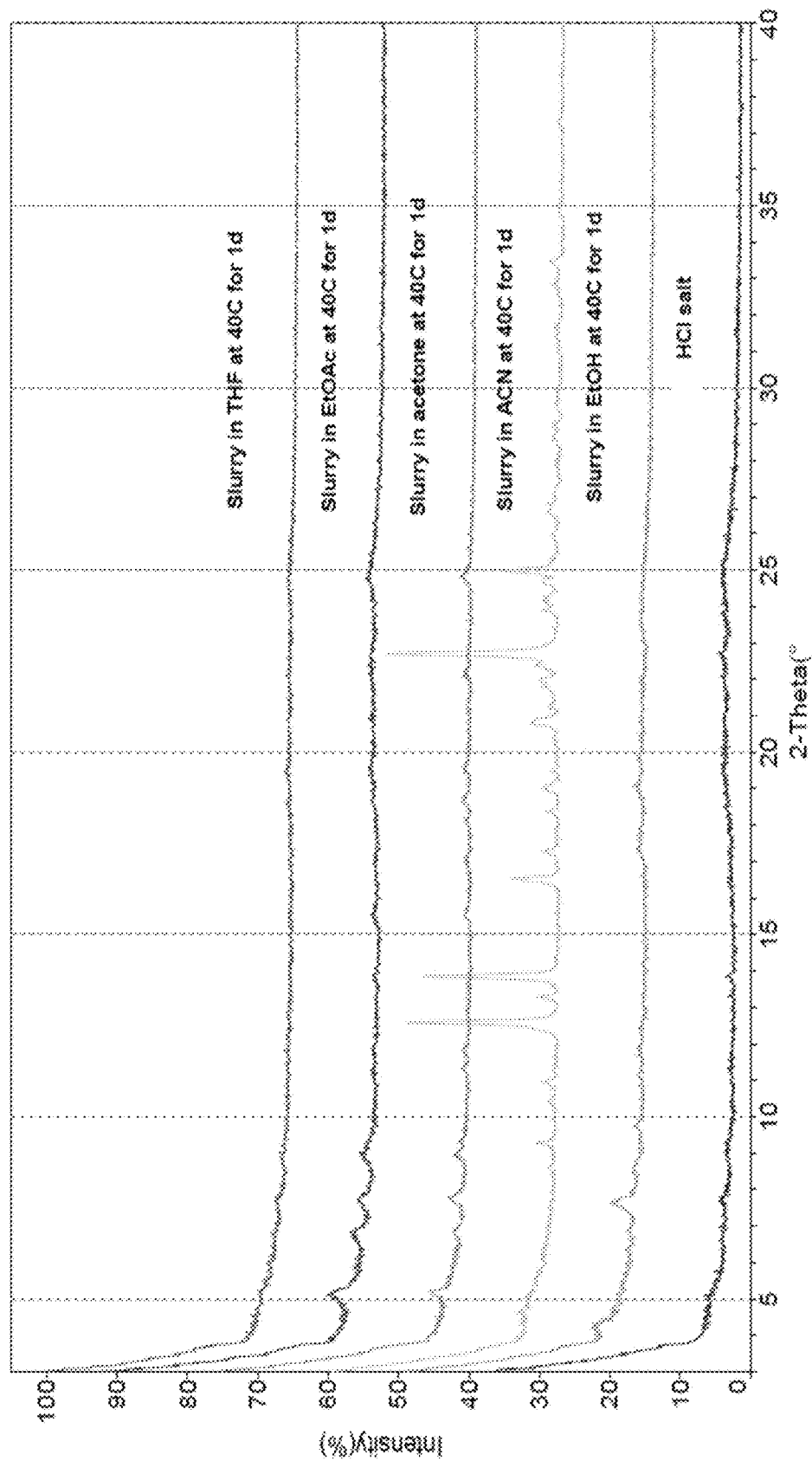
FIG. 11 is an overlay of the XRPD for the chloride salt as recrystallized from various solvents.
Figure 12:
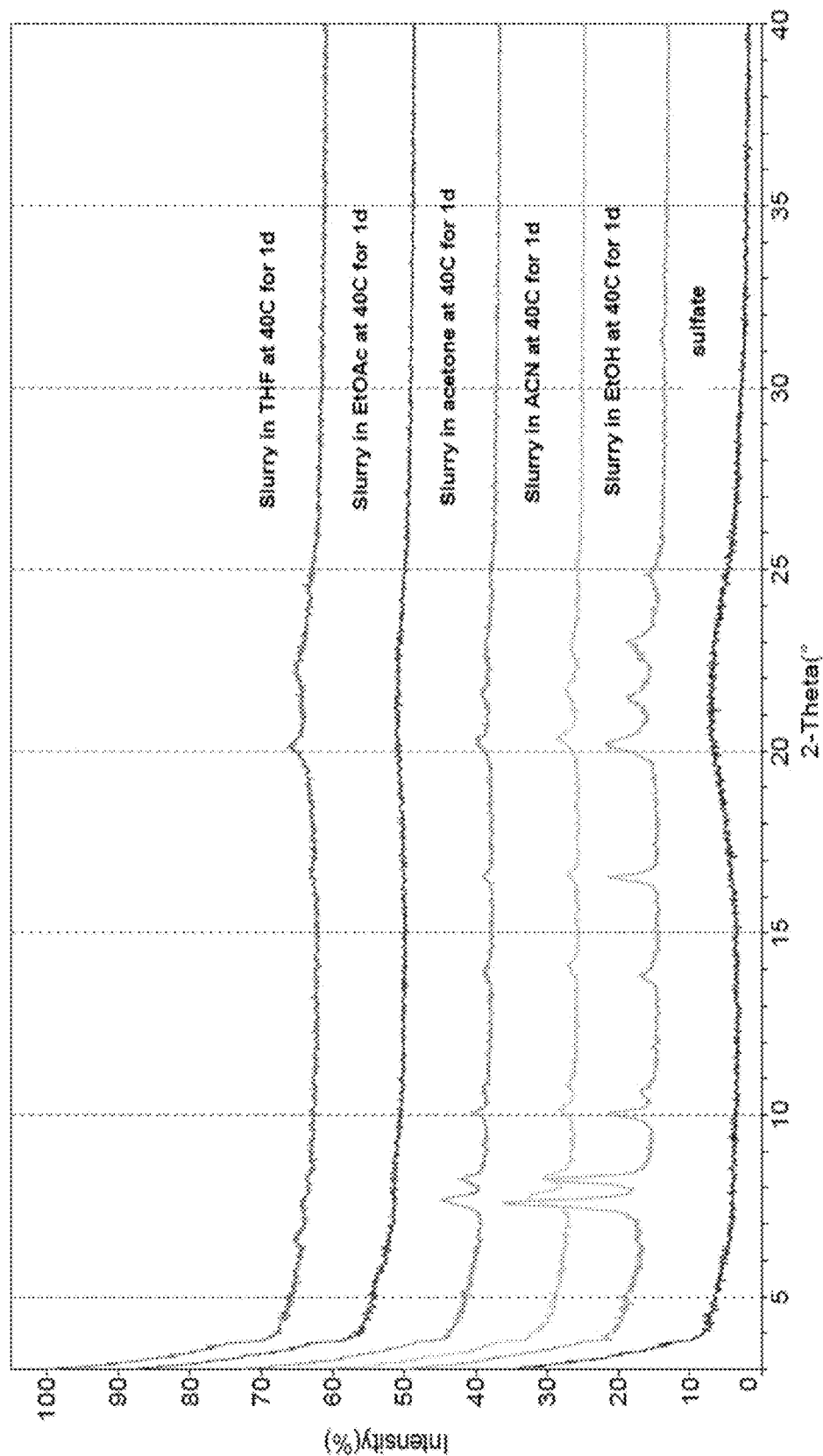
FIG. 12 is an overlay of the XRPD for the sulfate salt as recrystallized from various solvents.
Figure 13:
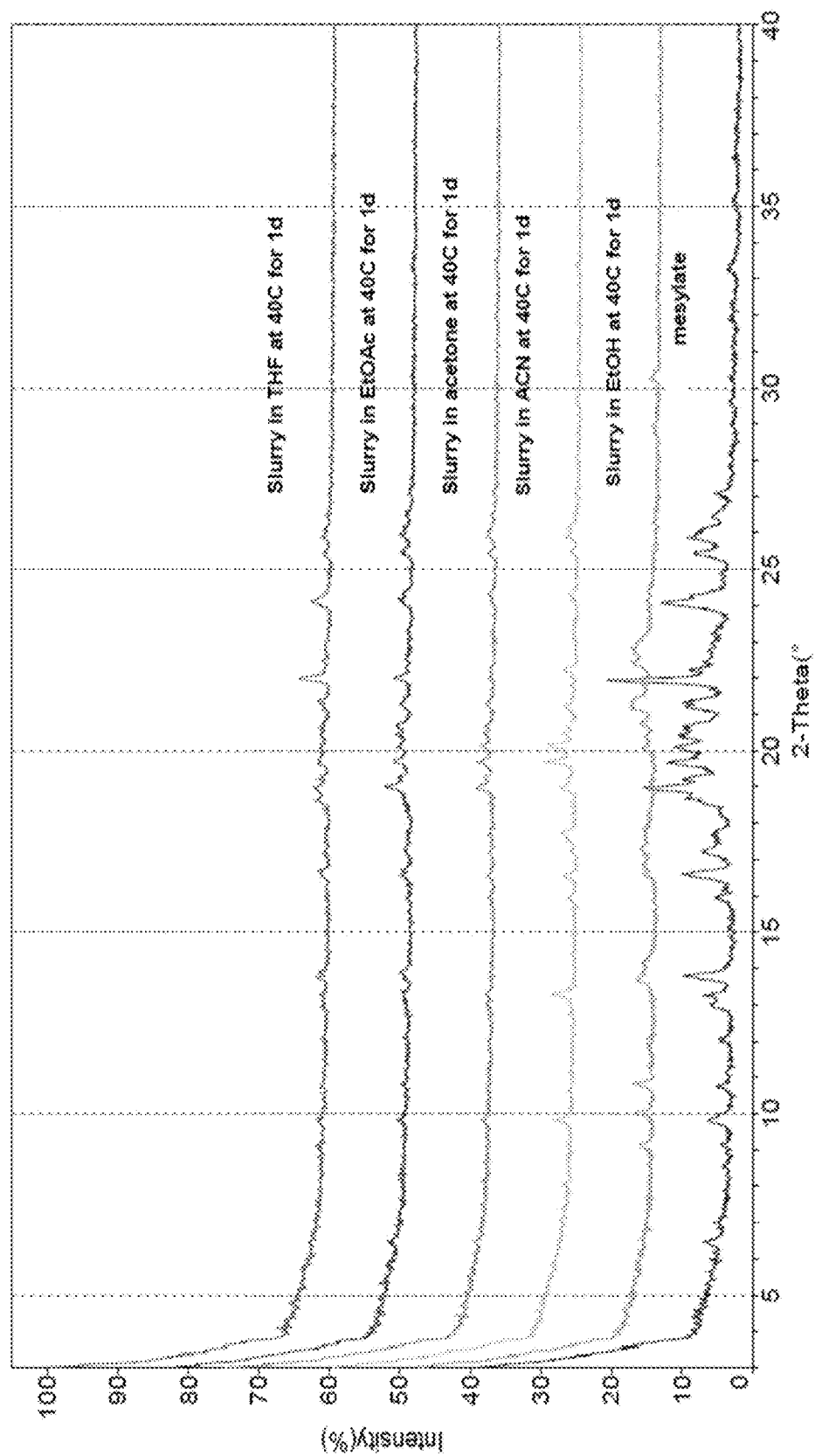
FIG. 13 is an overlay of the XRPD for the methanesulfonate salt as recrystallized from various solvents.

XRPD results (FIG. 11, FIG. 12, FIG. 13) demonstrated that the crystallinity of two of the three salts was improved via this recrystallization method in certain solvents: the chloride salt in ACN, the sulfate salt in EtOH.

Salt Preparation Method 2: This method employs a higher concentration of the free base, and slow evaporation of solvent, in order to obtain highly crystalline salt forms. Results with various acids, using EtOH as solvent, are disclosed in Table 4.

Step 1: About 10 mg of Example 1 free base was dissolved in a 1.5 mL glass vial with 0.2 mL of EtOH to achieve a homogeneous suspension.

Step 2: Next, an appropriate amount of solid acid was dissolved in a 8 mL glass vial with EtOH.

Step 3: A volume of acid solution sufficient to obtain a desired molar ratio of Example 1:acid was slowly titrated into free base solution with stirring on a magnetic stirrer. The volume of acid solutions add are listed in Table 4.

Step 4: The liquid phase thus obtained was stirred at room temperature for 24 hours to afford a precipitate.

The solid that was obtained through centrifugation was analyzed by XRPD to determine if a new crystalline form was obtained, and then dried under vacuum at 40° C. overnight for further characterization. Example 1 and pure solid acid suspended in MeOH were used as standards for Example 1 and pure solid acid, respectively.

Figure 14:
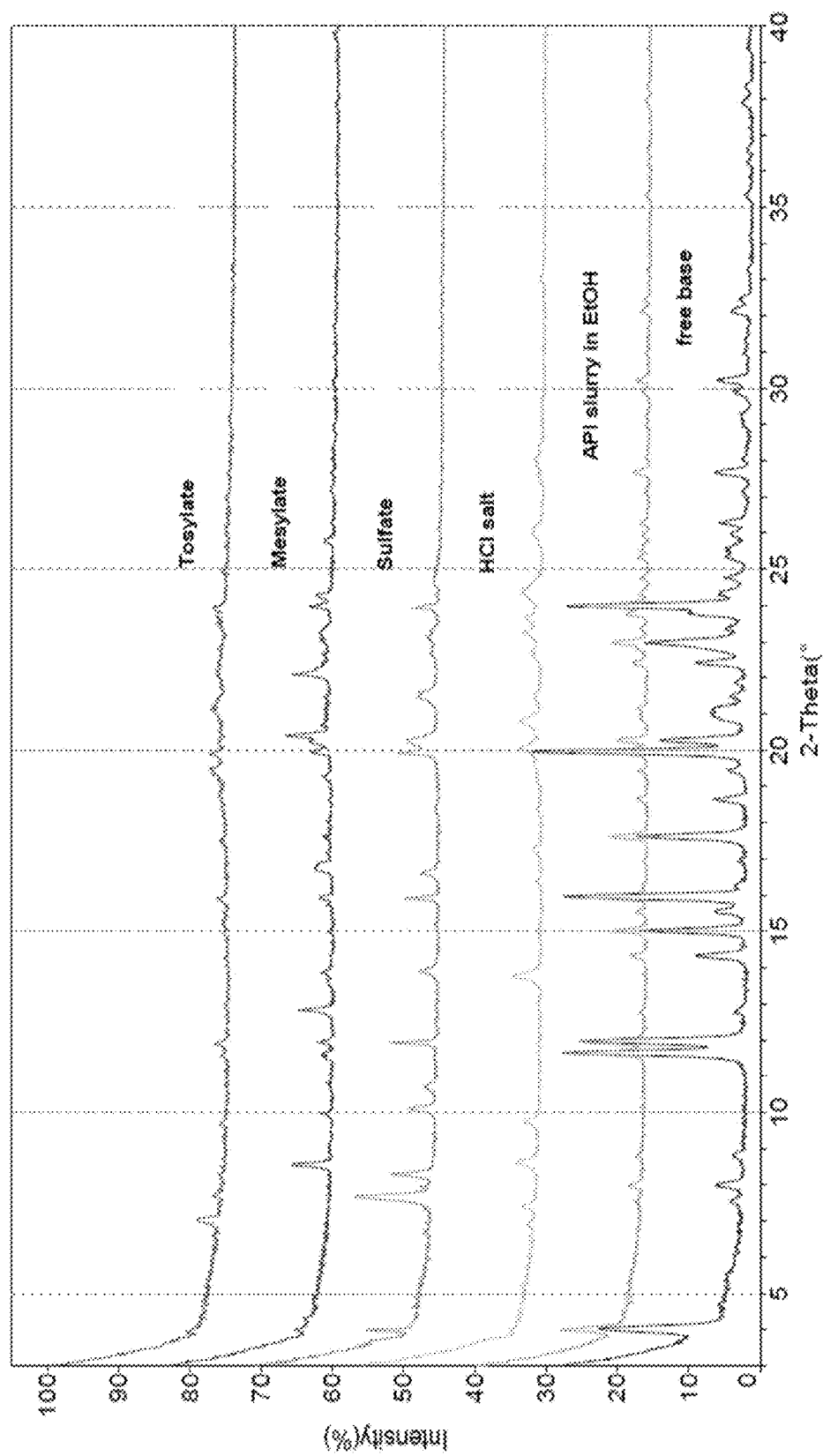
FIG. 14 is an overlay of the XRPD for salt candidates prepared by Method 2.

Based on the results disclosed in Table 4 and FIG. 14, chloride, sulfate, mesylate, and sulfate salts were potentially formed; however crystallinity of these salts was poor.

TABLE 4

Salt preparation using Method 2.

| Acid | Molar Ratio | Acid solution concentration, mg/mL | Volume of acid solution | Observation | XRD pattern |
|---|---|---|---|---|---|
| HCl | 1:1 | 59 | 0.034 | Clear, and then white solid precipitated | Poor crystalline |
| H$_2$SO$_4$ | 1:1 | 61.3 | 0.033 | Clear, and then white solid precipitated | Poor crystalline |
| MsOH | 1:1 | 49.3 | 0.040 | Clear, and then white solid precipitated | Poor crystalline |
| TsOH | 1:1 | 50 | 0.078 | Clear, and then allowed slow evaporation to afford solid | Poor crystalline |

Salt Preparation, Method 3: The 3rd round of salt synthesis was performed with an optimized procedure to generate highly crystalline salt forms. The details are listed below:

Step 1: Approximately 100 mg of Example 1 free base was dissolved in a 8 mL glass vial at 40° C. with 2 mL of ACN to achieve a homogeneous suspension.

Step 2: An appropriate amount of solid acid was dissolved in a 4 mL glass vial with ACN.

Step 3: A volume of acid solution sufficient to obtain a desired molar ratio of Example 1:acid was slowly titrated into a free base solution on a magnetic stirrer at a speed of 150 rpm. The volume of acid solutions add are listed in Table 5.

Step 4: The clear solution was kept stirring at room temperature without a cap and covered by aluminum foil with pinhole for 24 hours to allow for solvent evaporation.

Step 5: The obtained suspension was isolated by a centrifuge at a speed of 10000 rpm.

The supernatant was discarded and the resulting solid was analyzed by XRPD to determine if a new crystalline form was obtained, and then dried under vacuum at 40° C. overnight for further characterization. Example 1 and pure solid acid suspended in ACN were used as standards for Example 1 and pure solid acid control, respectively.

Figure 15:
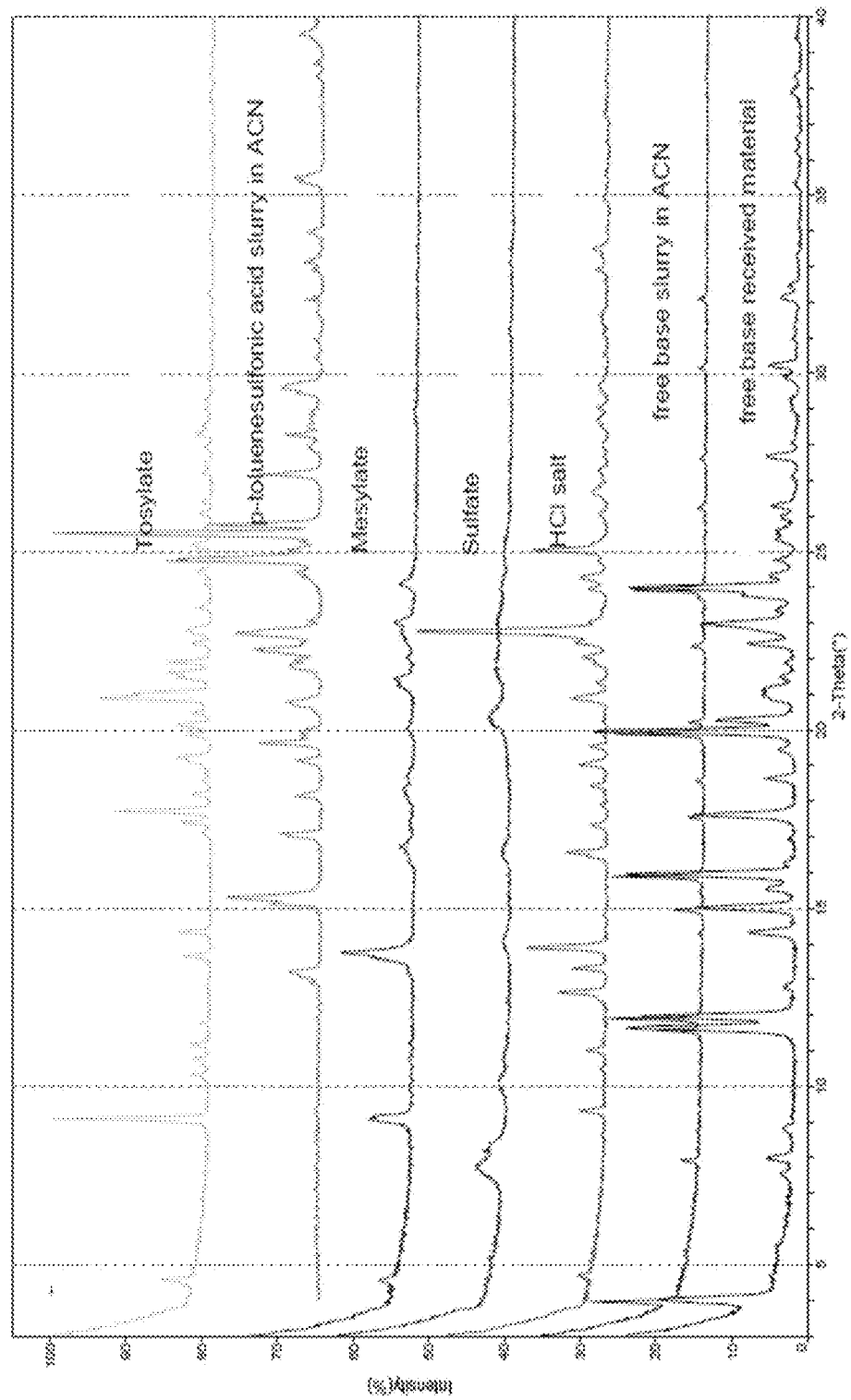
FIG. 15 is an overlay of the XRPD for salt candidates prepared by Method 3.
Figure 16:
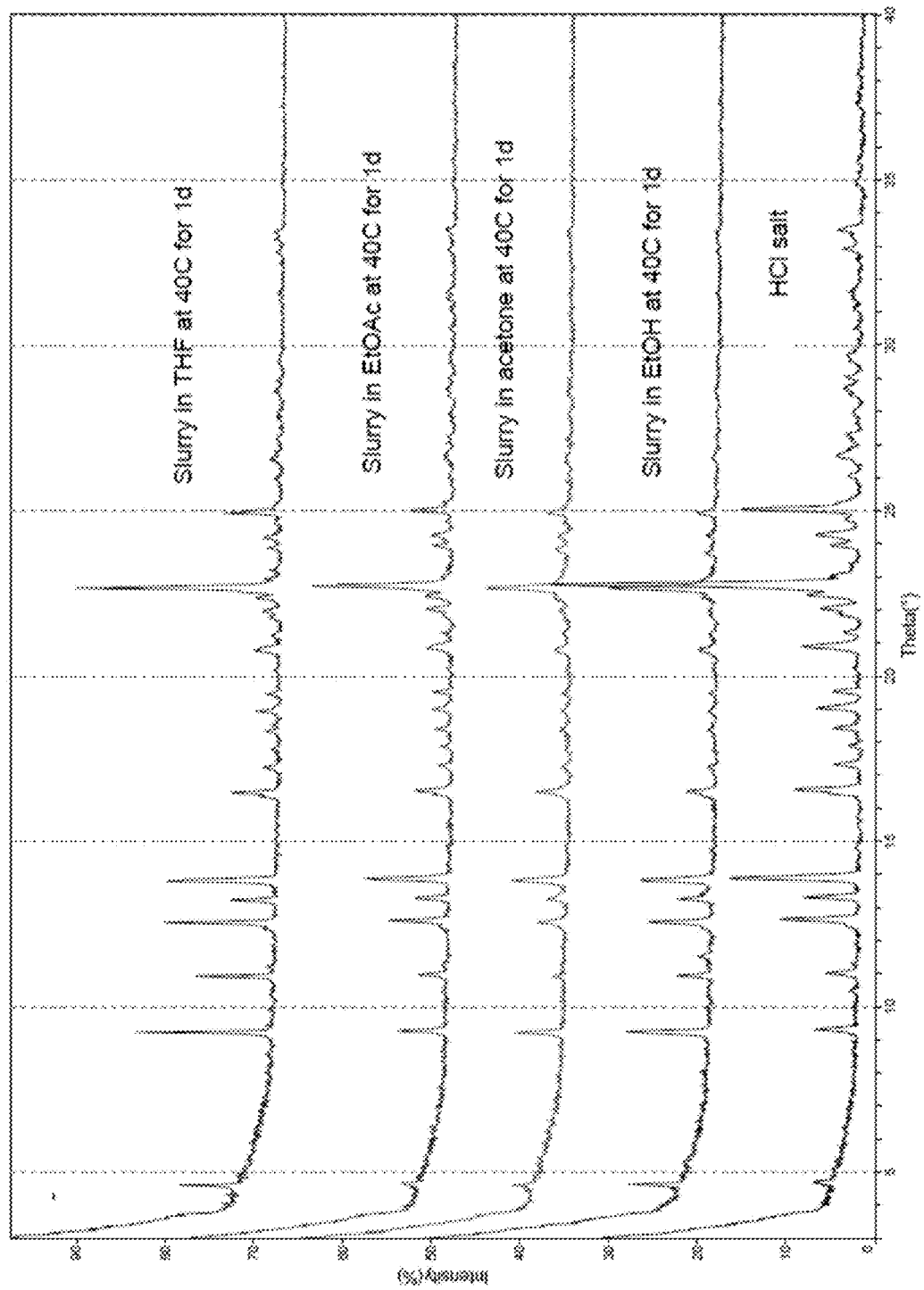
FIG. 16 is an overlay of the XRPD for the chloride salt as prepared by Method 3 and recrystallized from EtOAc.
Figure 17:
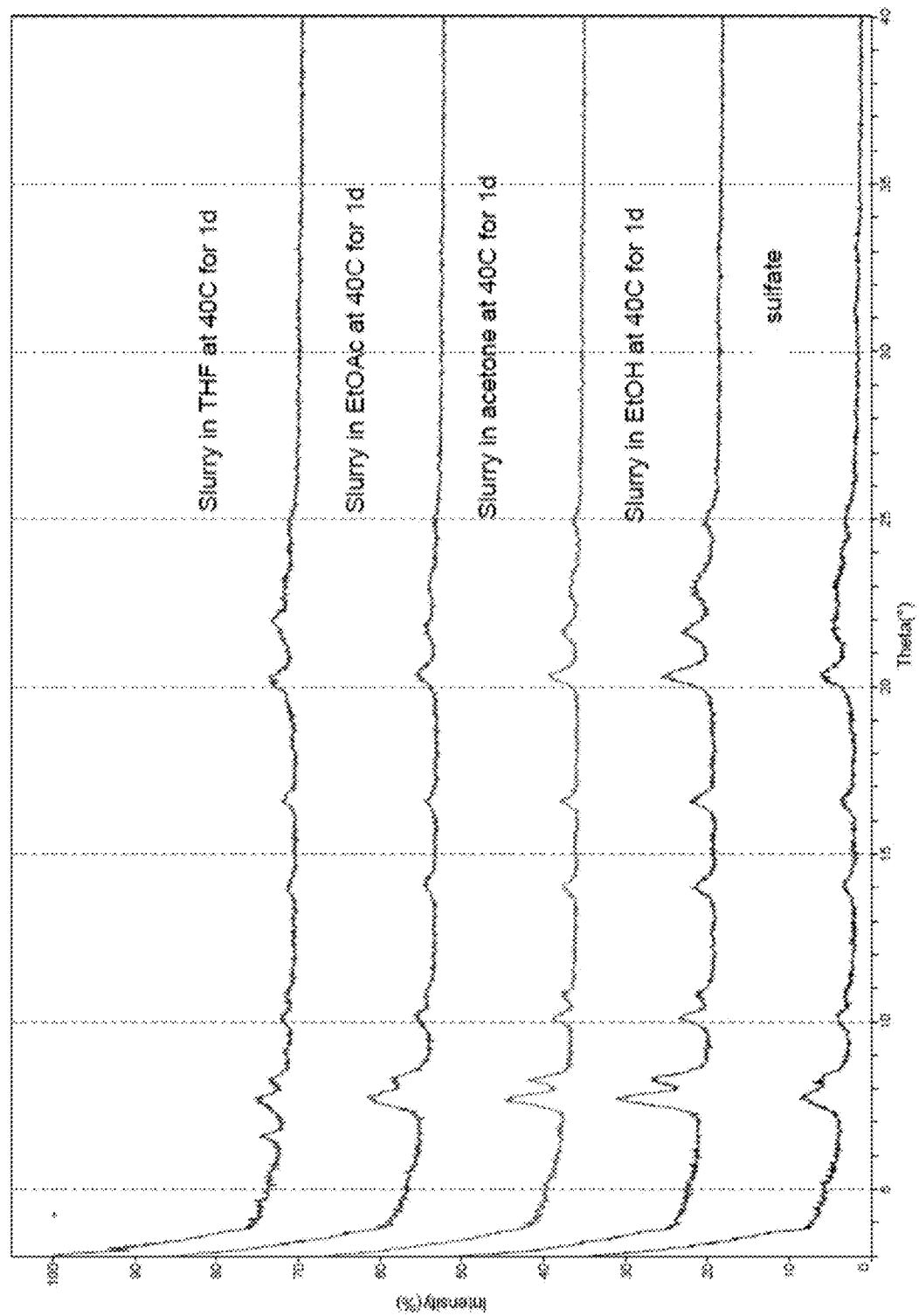
FIG. 17 is an overlay of the XRPD for the sulfate salt as prepared by Method 3 and recrystallized from EtOAc.
Figure 18:
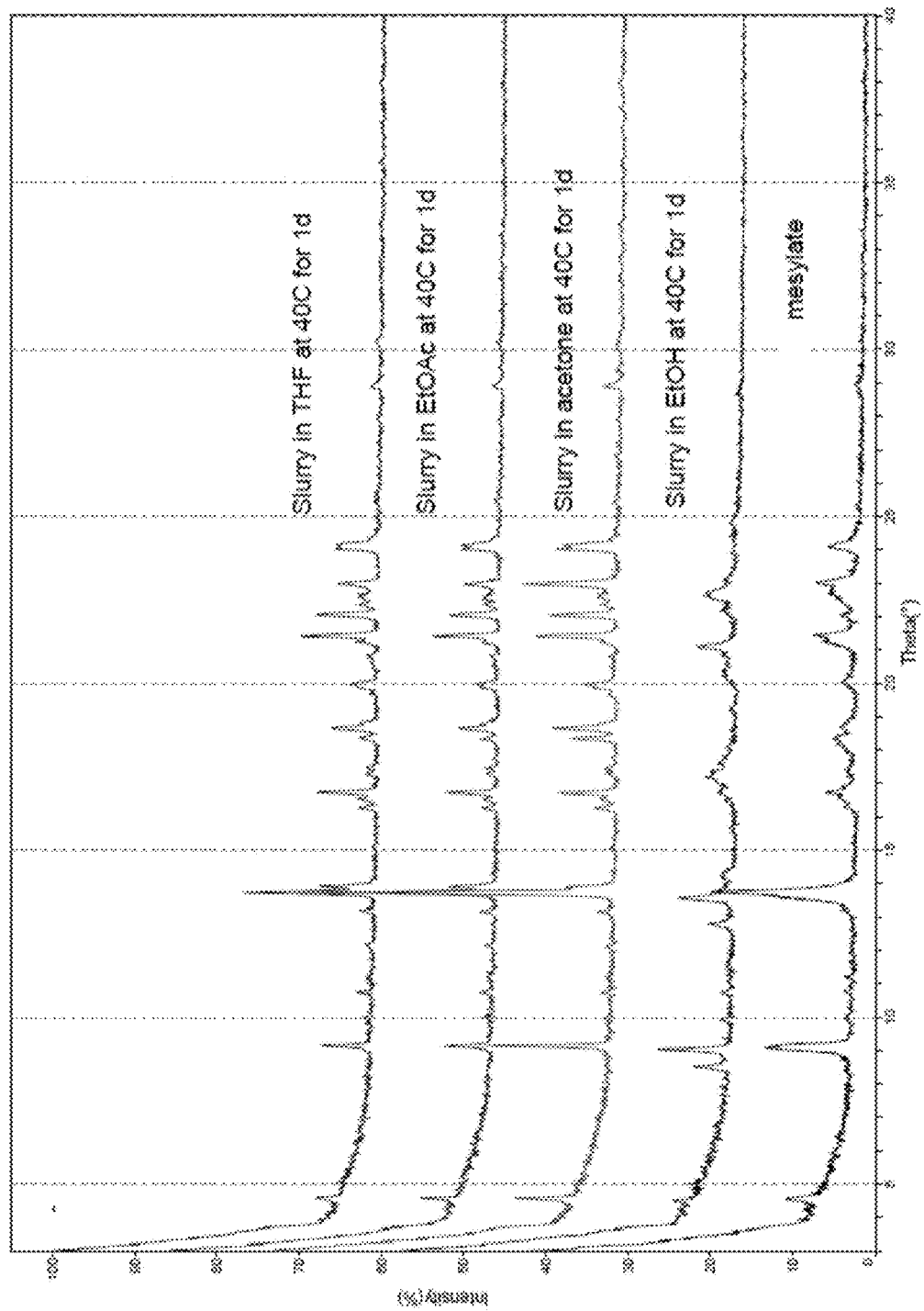
FIG. 18 is an overlay of the XRPD for the mesylate salt as prepared by Method 3 and recrystallized from EtOAc.
Figure 19:
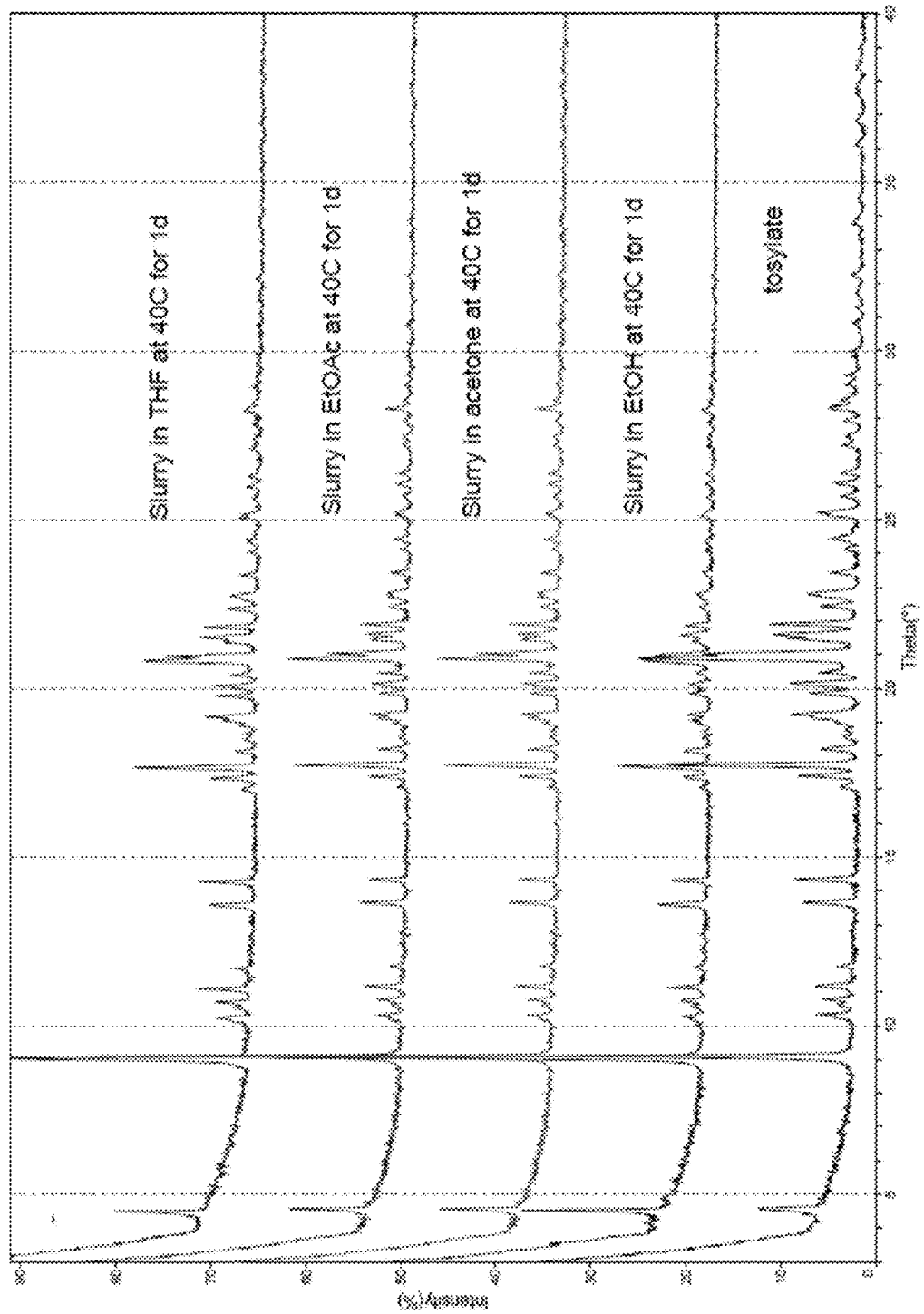
FIG. 19 is an overlay of the XRPD for the tosylate salt as prepared by Method 3 and recrystallized from EtOAc.

Based on the results disclosed in Table 5 and FIG. 15, two of the counterions (chloride and tosylate) provided salts exhibiting good crystal forms. The obtained salts were recrystallized in an attempt to improve crystallinity.

was obtained, and then dried under vacuum at 40° C. overnight for further characterization.

TABLE 5

Salt preparation using Method 3.

| Acid | Molar Ratio | Acid solution concentration, mg/mL | Volume of acid solution | Observation | XRD pattern |
|---|---|---|---|---|---|
| HCl | 1:1 | 59 | 0.034 | Clear, and then white solid precipitated immediately | Good crystalline |
| H$_2$SO$_4$ | 1:1 | 61.3 | 0.033 | Clear, and then white solid precipitated immediately | Poor crystalline |
| MsOH | 1:1 | 49.3 | 0.040 | Clear, and then white solid precipitated immediately | Poor crystalline |
| TsOH | 1:1 | 50 | 0.078 | Clear, and then white solid precipitated after 1 hour | Good crystalline |

Recrystallization of Method 3 Product: Four potential salts (chloride, sulfate, mesylate and tosylate) were recrystallized in several solvents in order to improve crystallinity. About 10 mg of salt candidate was weighed into a 1.5 mL glass vial separately, and then 0.2 mL of a selected solvent (EtOH, acetone, EtOAc and THF) was added. The obtained suspension was agitated at 40° C. for 1 day on a thermomixer and then centrifuged at 10000 rpm. The resulting solid was dried under vacuum at 40° C. overnight for XRPD test.

XRPD results (FIG. 16, FIG. 17, FIG. 18, FIG. 19) demonstrated that the crystallinity of three salts (chloride, mesylate and tosylate) was slightly improved via this recrystallization method, employing EtOAc.

Method 3 Scale-Up: Method 3, followed by optional EtOAc recrystallization, was repeated on a larger scale for the chloride, mesylate and tosylate salts.

Step 1: About 200 mg of Example 1 free base was dissolved in a 8 mL glass vial at 40° C. with 4 mL of ACN to achieve a homogeneous suspension.

Step 2: An amount of solid acid was dissolved in a 4 mL glass vial with ACN.

Step 3: A volume of acid solution sufficient to obtain a desired molar ratio of Example 1:acid (the volume of acid solutions added are listed in Table 6) was slowly titrated into a free base solution on a magnetic stirrer at 150 rpm.

Step 4: The clear solution was stirred at ambient temperature without a cap and covered by aluminum foil with pinhole for 24 hours to get precipitate.

Step 5: The obtained suspension was isolated by a centrifuge at a speed of 10000 rpm.

Figure 20:
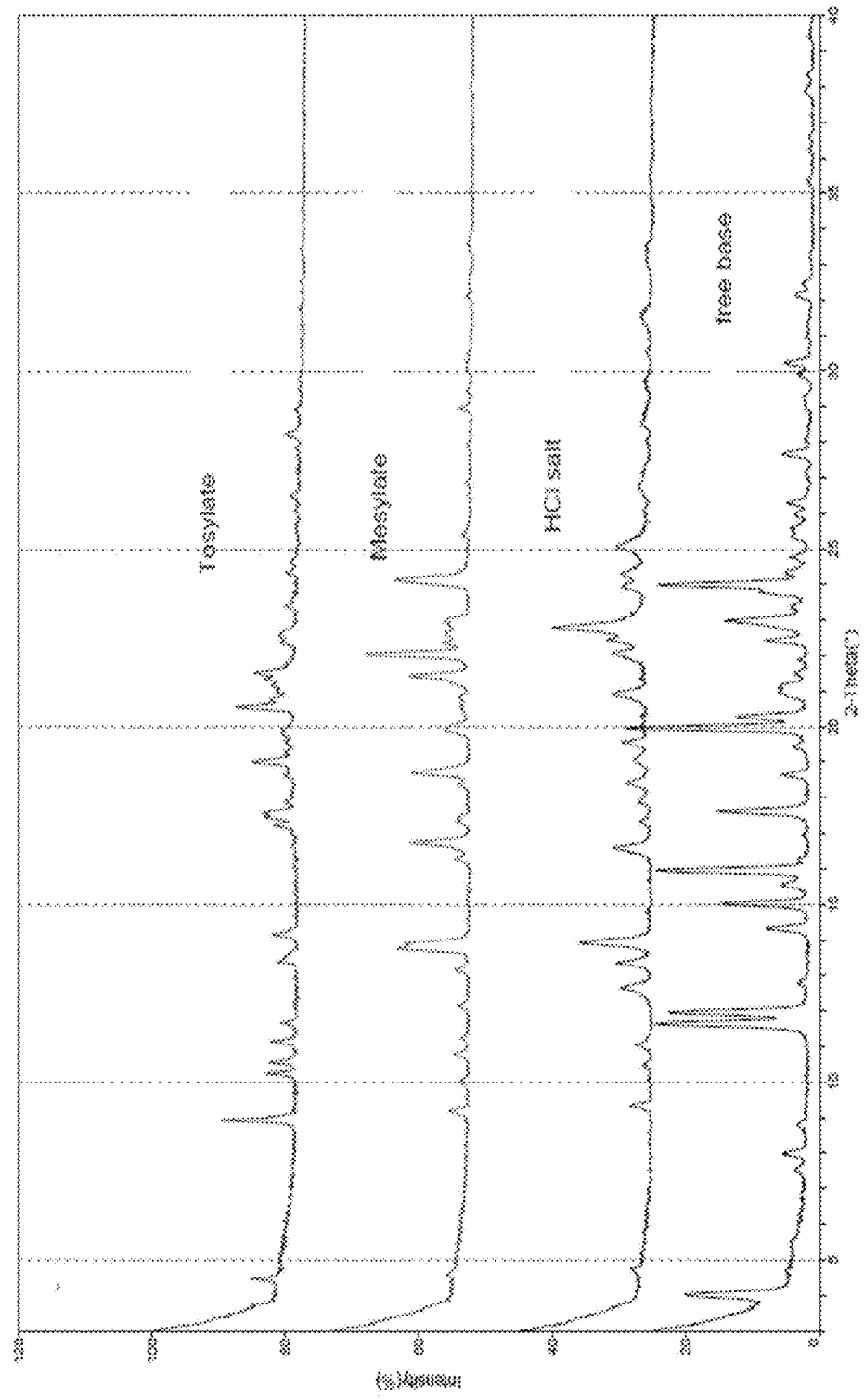
FIG. 20 is an overlay of the XRPD for the salt candidates from the Method 3 scale-up.
Figure 21:
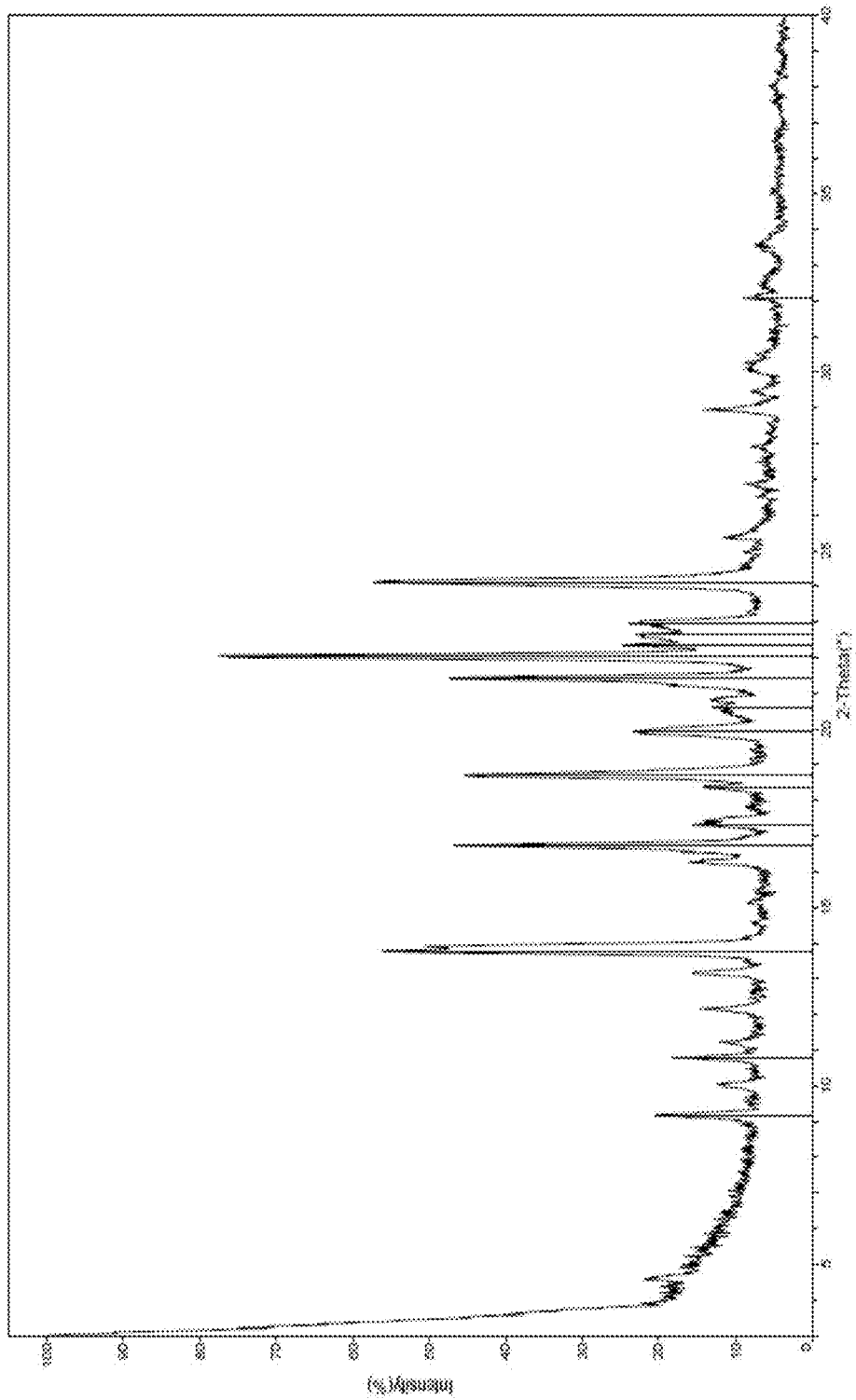
FIG. 21 is an XRPD of the mesylate salt as prepared by the Method 3 scale-up.

The supernatant was discarded and the resulting solid was analyzed by XRPD to determine if a new crystalline form Based on the results listed in Table 6 and FIG. 20, chloride, mesylate and tosylate salts were reproduced successfully. Mesylate salt (FIG. 21 and Table 7) appeared to be well crystallized during salt synthesis, while both chloride and tosylate salts require recrystallization in EtOAc to improve the crystallinity.

Recrystallization of Method 3 Scale-Up Product: About 100 mg of the salt was weighed into a 1.5 mL glass vial separately, and then 1 mL of EtOAc was added. The obtained suspension was agitated at 40° C. for 1 day on the thermomixer and then centrifuged at 10000 rpm. The resulting solid was dried under vacuum at 40° C. overnight for XRPD test.

Figure 22:
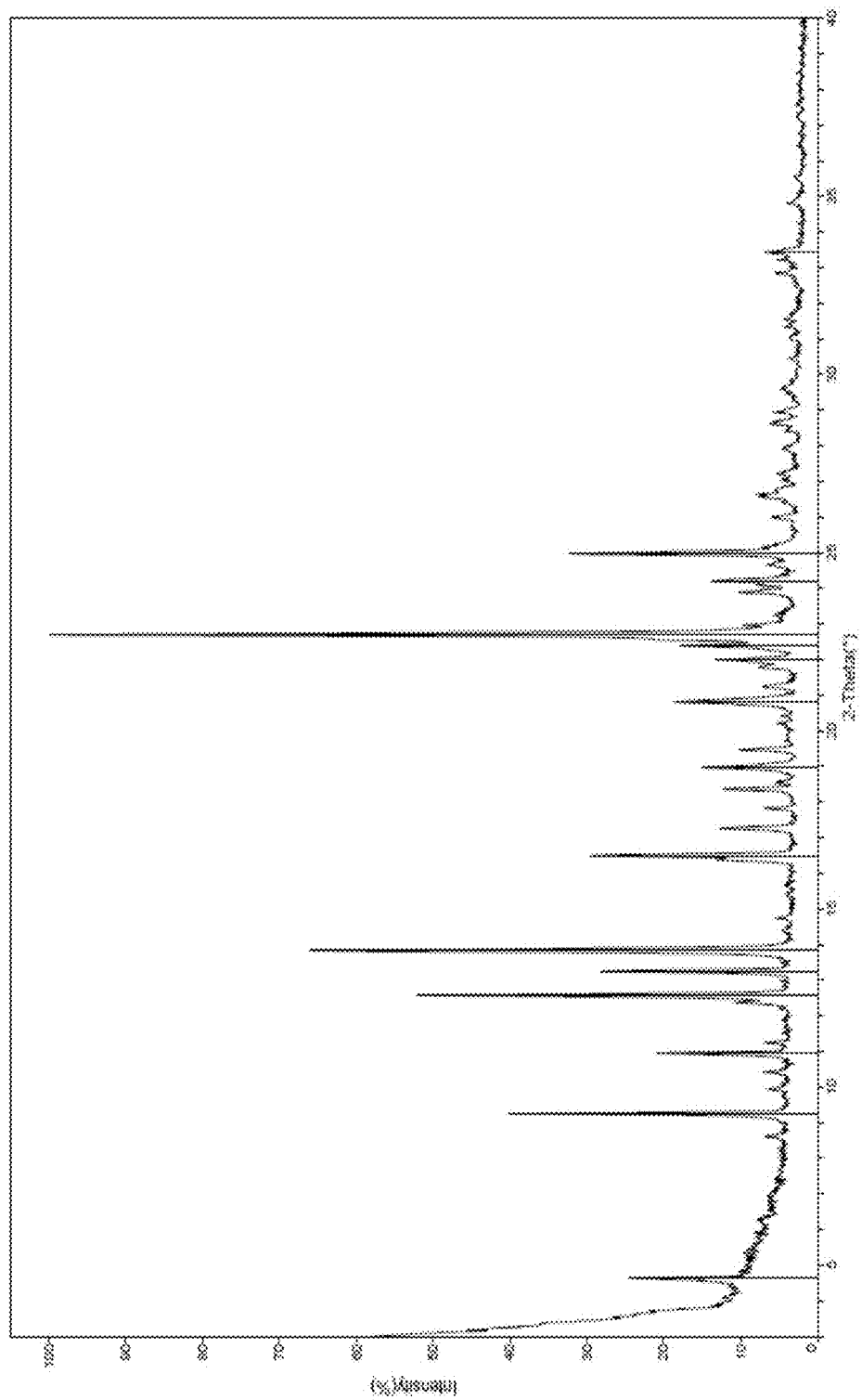
FIG. 22 is an XRPD of the chloride salt as prepared by the Method 3 scale-up and recrystallized from EtOAc.
Figure 23:
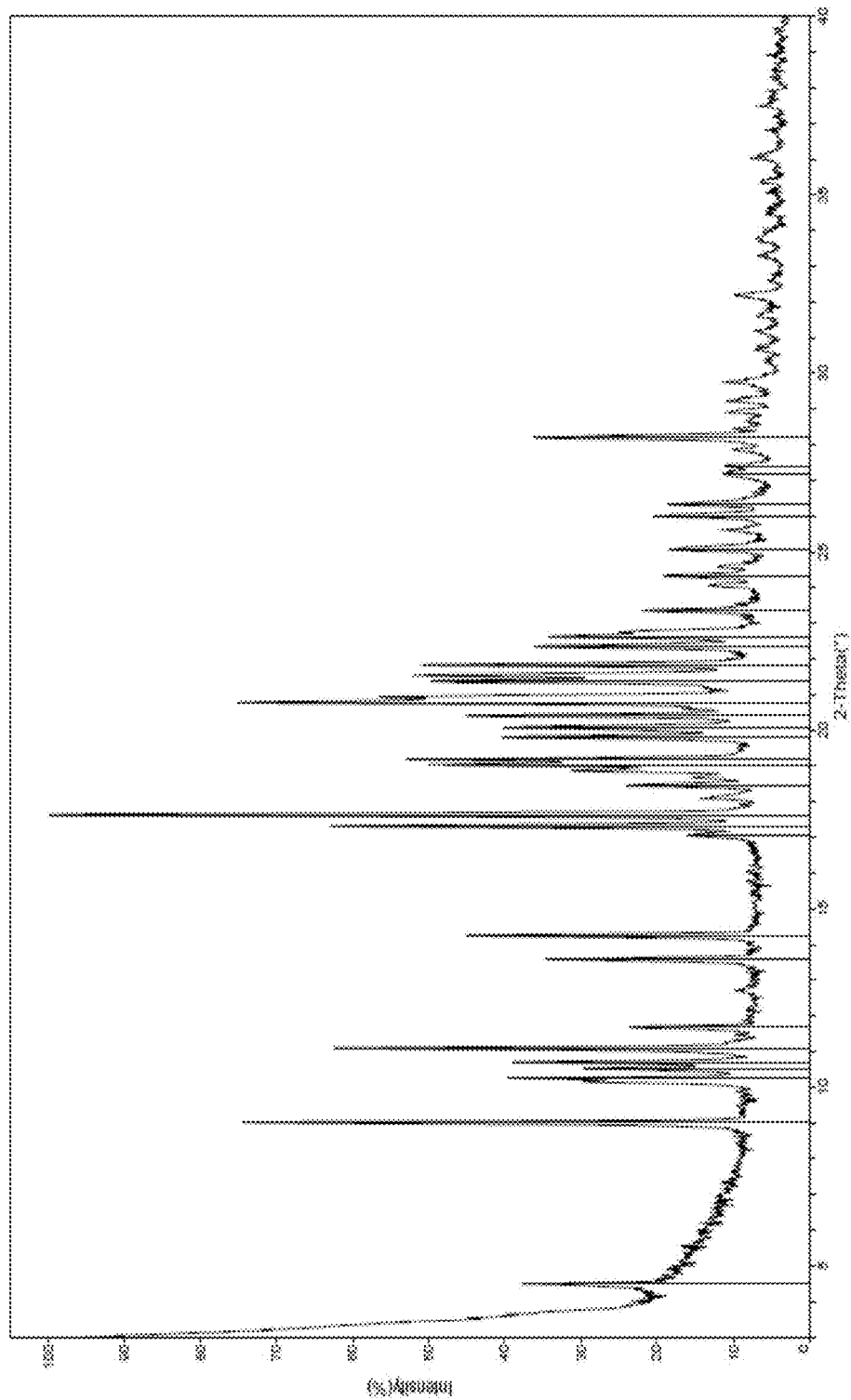
FIG. 23 is an XRPD of the tosylate salt as prepared by the Method 3 scale-up and recrystallized from EtOAc.

XRPD results (FIG. 22, FIG. 23 and Table 8, Table 9) showed the crystallinity of the chloride and tosylate salts were improved on using this recrystallization method. For this reason, the re-prepared chloride salt (recrystallized in EtOAc), mesylate and tosylate (recrystallized in EtOAc) were used for further characterization.

TABLE 6

Salt preparation using Method 3 Scale-Up.

| Acid | Molar Ratio | Acid solution concentration, mg/mL | Volume of acid solution | Observation | XRD pattern |
|---|---|---|---|---|---|
| HCl | 1:1 | 59 | 0.034 | Clear, and then white solid precipitated immediately | Good crystalline |
| H$_2$SO$_4$ | 1:1 | 59 | 0.68 | Clear, and then white solid precipitated immediately | Good crystalline |
| MsOH | 1:1 | 49.3 | 0.80 | Clear, and then white solid precipitated immediately | Good crystalline |
| TsOH | 1:1 | 50 | 1.57 | Clear, and then white solid precipitated after 1 hour | Good crystalline |

TABLE 7

XRPD peak listing of mesylate from Method 3 scale-up.

| 2-Theta | d(Å) | BG | Height | I % | Area | I % | FWHM |
|---|---|---|---|---|---|---|---|
| 9.176 | 9.6296 | 153 | 245 | 19.8 | 1880 | 12.7 | 0.129 |
| 10.791 | 8.1921 | 140 | 214 | 17.3 | 1714 | 11.6 | 0.134 |
| 13.772 | 6.4247 | 131 | 969 | 78.2 | 14796 | 100.0 | 0.256 |
| 16.733 | 5.2940 | 126 | 790 | 63.8 | 8447 | 57.1 | 0.179 |
| 17.321 | 5.1153 | 134 | 161 | 13.0 | 1879 | 12.7 | 0.196 |
| 18.385 | 4.8216 | 130 | 144 | 11.6 | 2268 | 15.3 | 0.264 |
| 18.703 | 4.7405 | 134 | 753 | 60.8 | 8833 | 59.7 | 0.197 |
| 19.927 | 4.4520 | 150 | 306 | 24.7 | 4164 | 28.1 | 0.228 |
| 20.620 | 4.3039 | 165 | 88 | 7.1 | 1711 | 11.6 | 0.326 |
| 21.410 | 4.1469 | 175 | 750 | 60.5 | 7402 | 50.0 | 0.165 |

TABLE 7-continued

XRPD peak listing of mesylate from Method 3 scale-up.

| 2-Theta | d(Å) | BG | Height | I % | Area | I % | FWHM |
|---|---|---|---|---|---|---|---|
| 22.054 | 4.0271 | 277 | 1239 | 100.0 | 10331 | 69.8 | 0.140 |
| 22.337 | 3.9768 | 165 | 317 | 25.6 | 9076 | 61.3 | 0.480 |
| 22.647 | 3.9230 | 158 | 289 | 23.3 | 10278 | 69.5 | 0.596 |
| 22.948 | 3.8723 | 140 | 326 | 26.3 | 6822 | 46.1 | 0.351 |
| 24.129 | 3.6853 | 139 | 982 | 79.3 | 13054 | 88.2 | 0.223 |
| 32.078 | 2.7879 | 83 | 91 | 7.3 | 1685 | 11.4 | 0.310 |

TABLE 8

XRPD peak listing of chloride salt from Method 3 scale-up and EtOAc recrystallization.

| 2-Theta | d(Å) | BG | Height | I % | Area | I % | FWHM |
|---|---|---|---|---|---|---|---|
| 4.632 | 19.0595 | 362 | 546 | 15.3 | 2967 | 10.9 | 0.091 |
| .9.255 | 9.5479 | 153 | 1332 | 37.2 | 5802 | 21.2 | 0.073 |
| 10.951 | 8.0728 | 142 | 630 | 17.6 | 3095 | 11.3 | 0.082 |
| 12.584 | 7.0284 | 149 | 1783 | 49.9 | 9975 | 36.5 | 0.094 |
| 13.246 | 6.6788 | 151 | 894 | 25.0 | 4362 | 16.0 | 0.082 |
| 13.831 | 6.3976 | 147 | 2306 | 64.5 | 14227 | 52.1 | 0.103 |
| 16.497 | 5.3690 | 118 | 974 | 27.2 | 6806 | 24.9 | 0.117 |
| 18.978 | 4.6723 | 117 | 432 | 12.1 | 3224 | 11.8 | 0.125 |
| 20.815 | 4.2639 | 126 | 556 | 15.5 | 4981 | 18.2 | 0.150 |
| 21.996 | 4.0376 | 140 | 350 | 9.8 | 2854 | 10.4 | 0.137 |
| 22.392 | 3.9671 | 135 | 522 | 14.6 | 4813 | 17.6 | 0.155 |
| 22.693 | 3.9152 | 139 | 3576 | 100.0 | 27325 | 100.0 | 0.128 |
| 24.210 | 3.6732 | 133 | 376 | 10.5 | 3024 | 11.1 | 0.135 |
| 24.977 | 3.5621 | 123 | 1070 | 29.9 | 8011 | 29.3 | 0.126 |
| 33.438 | 2.6776 | 75 | 175 | 4.9 | 2905 | 10.6 | 0.278 |

TABLE 9

XRPD peak listing of tosylate from Method 3 scale-up and EtOAc recrystallization.

| 2-Theta | d(Å) | BG | Height | I % | Area | I % | FWHM |
|---|---|---|---|---|---|---|---|
| 4.497 | 19.6325 | 446 | 431 | 20.1 | 2219 | 14.2 | 0.086 |
| 9.016 | 9.8006 | 190 | 1545 | 71.9 | 8550 | 54.7 | 0.093 |
| 10.255 | 8.6188 | 205 | 717 | 33.4 | 6223 | 39.8 | 0.146 |
| 10.536 | 8.3894 | 187 | 502 | 23.4 | 4445 | 28.4 | 0.148 |
| 10.714 | 8.2506 | 191 | 714 | 33.2 | 4310 | 27.6 | 0.101 |
| 11.104 | 7.9615 | 215 | 1242 | 57.8 | 6476 | 41.4 | 0.087 |
| 11.682 | 7.5690 | 183 | 362 | 16.9 | 1951 | 12.5 | 0.090 |
| 13.576 | 6.5171 | 162 | 643 | 29.9 | 3931 | 25.2 | 0.103 |
| 14.262 | 6.2050 | 156 | 894 | 41.6 | 5475 | 35.0 | 0.103 |
| 17.066 | 5.1914 | 172 | 199 | 9.3 | 2097 | 13.4 | 0.177 |
| 17.324 | 5.1146 | 175 | 1290 | 60.1 | 8180 | 52.4 | 0.106 |
| 17.640 | 5.0238 | 182 | 2148 | 100.0 | 13354 | 85.5 | 0.104 |
| 18.454 | 4.8040 | 194 | 364 | 16.9 | 2574 | 16.5 | 0.119 |
| 18.880 | 4.6964 | 193 | 537 | 25.0 | 9411 | 60.2 | 0.294 |
| 19.039 | 4.6575 | 202 | 963 | 44.8 | 9759 | 62.5 | 0.170 |
| 19.179 | 4.6239 | 201 | 1030 | 48.0 | 13207 | 84.5 | 0.215 |
| 19.794 | 4.4815 | 222 | 716 | 33.3 | 4549 | 29.1 | 0.107 |
| 20.069 | 4.4209 | 252 | 683 | 31.8 | 4899 | 31.4 | 0.120 |
| 20.402 | 4.3493 | 248 | 799 | 37.2 | 4594 | 29.4 | 0.096 |
| 20.782 | 4.2708 | 284 | 1471 | 68.5 | 15624 | 100.0 | 0.178 |
| 21.386 | 4.1514 | 267 | 891 | 41.5 | 10144 | 64.9 | 0.191 |
| 21.840 | 4.0661 | 230 | 956 | 44.5 | 5516 | 35.3 | 0.097 |
| 22.352 | 3.9742 | 198 | 641 | 29.8 | 4776 | 30.6 | 0.125 |
| 22.629 | 3.9261 | 188 | 607 | 28.3 | 7111 | 45.5 | 0.196 |
| 23.358 | 3.8053 | 168 | 338 | 15.7 | 2201 | 14.1 | 0.109 |
| 24.344 | 3.6532 | 158 | 282 | 13.1 | 2564 | 16.4 | 0.152 |
| 25.059 | 3.5506 | 154 | 271 | 12.6 | 2195 | 14.0 | 0.136 |
| 26.004 | 3.4237 | 143 | 330 | 15.4 | 3005 | 19.2 | 0.153 |
| 26.323 | 3.3829 | 140 | 288 | 13.4 | 2681 | 17.2 | 0.156 |
| 27.186 | 3.2775 | 132 | 129 | 6.0 | 2232 | 14.3 | 0.290 |
| 27.405 | 3.2518 | 130 | 126 | 5.9 | 2235 | 14.3 | 0.297 |
| 28.211 | 3.1606 | 136 | 706 | 32.9 | 6812 | 43.6 | 0.162 |

Provided herein salts of Example 1 characterized by having XRPD peaks as disclosed above. In certain embodiments, salts are characterized by having at least one, at least three, or at least five of the XRPD peaks as disclosed above. In certain embodiments, salts are characterized by having between five and ten of the XRPD peaks as disclosed above. Such peaks may be referred to by their 2 theta shift.

Accordingly, provided herein is the mesylate salt of Example 1 (i.e., wherein $R^-$ is $CH_3SO_3^-$). In certain embodiments, the mesylate salt is characterized by having one or more x-ray powder diffraction peaks chosen from about 9.2, about 10.8, about 13.8, about 16.7, about 17.3, about 18.4, about 18.7, about 19.9, about 20.6, about 21.4, about 22.1, about 22.3, about 22.6, about 22.9, about 24.1, and about 32.1 degrees 2-theta. In certain embodiments, the mesylate salt is characterized by having two, three, four, five, or more of the peaks. In certain embodiments, the mesylate salt is characterized by having three or more of the peaks. In certain embodiments, the mesylate salt is characterized by having five or more of the peaks.

Accordingly, provided herein is the chloride salt of Example 1 (i.e., wherein $R^-$ is $Cl^-$). In certain embodiments, the chloride salt is characterized by having one or more x-ray powder diffraction peaks chosen from about 4.6, about 9.26, about 11.0, about 12.6, about 13.2, about 13.8, about 16.5, about 19.0, about 20.8, about 22.0, about 22.4, about 22.7, about 24.2, about 25.0, and about 33.4 degrees 2-theta. In certain embodiments, the chloride salt is characterized by having two, three, four, five, or more of the peaks. In certain embodiments, the chloride salt is characterized by having three or more of the peaks. In certain embodiments, the chloride salt is characterized by having five or more of the peaks.

Accordingly, provided herein is the tosylate salt of Example 1 (i.e., wherein $R^-$ is 4-$MePhSO_3^-$). In certain embodiments, the chloride salt is characterized by having one or more x-ray powder diffraction peaks chosen from about 4.5, about 9.0, about 10.3, about 10.5, about 10.7, about 11.1, about 11.7, about 13.6, about 14.3, about 17.1, about 17.3, about 17.6, about 18.5, about 18.9, about 19.0, about 19.2, about 19.8, about 20.1, about 20.4, about 20.8, about 21.4, about 21.8, about 22.4, about 22.6, about 23.4, about 24.3, about 25.1, about 26.0, about 26.3, about 27.2, about 27.4, and about 28.2 degrees 2-theta. In certain embodiments, the tosylate salt is characterized by having two, three, four, five, or more of the peaks. In certain embodiments, the tosylate salt is characterized by having three or more of the peaks. In certain embodiments, the tosylate salt is characterized by having five or more of the peaks.

Also provided are salts of Example, characterized by having a X-ray powder diffraction pattern as shown in the relevant Figures.

Also provided herein is the sulfate salt of Example 1 (i.e., wherein $R^-$ is $HSO_4^-$).

Figure 24:
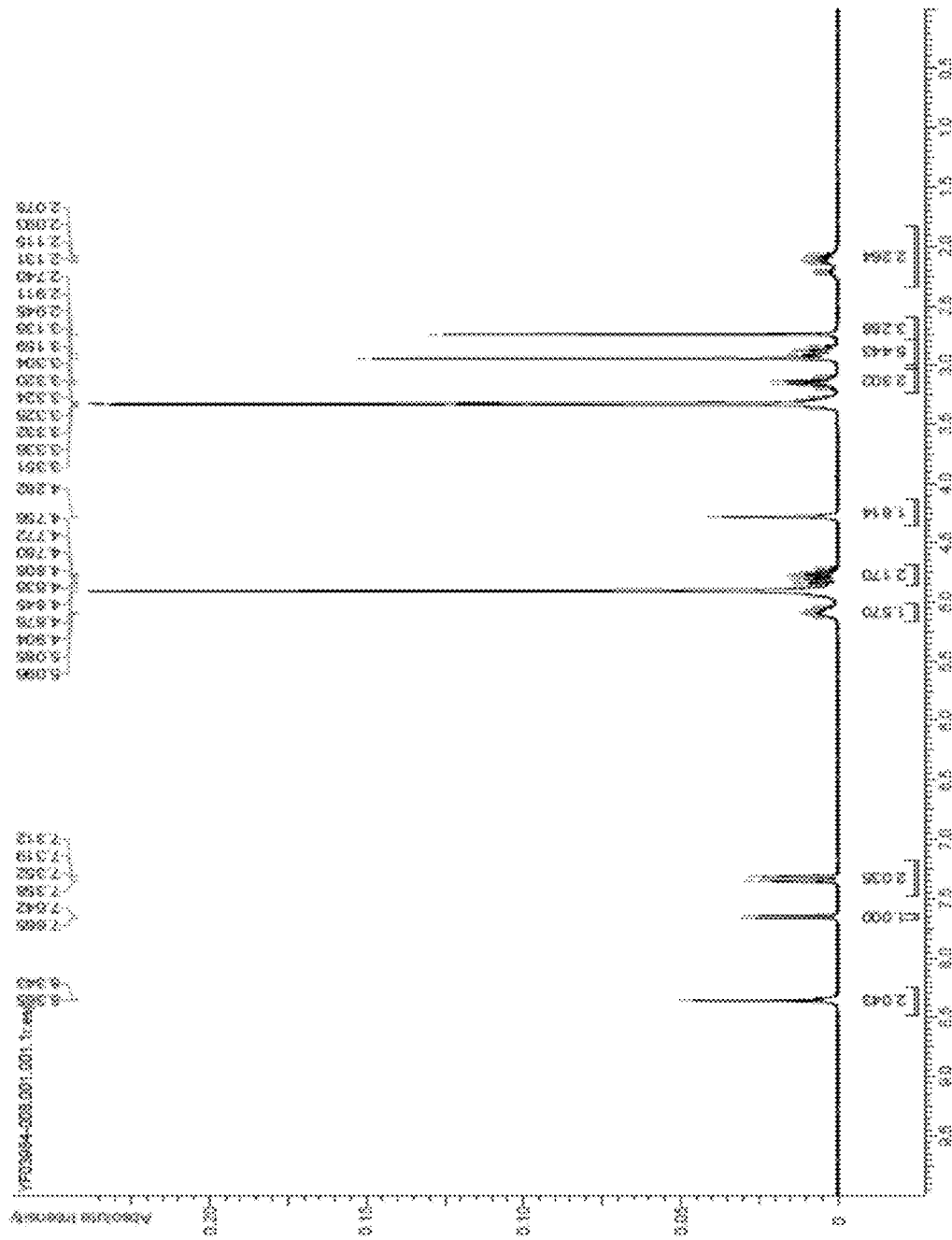
FIG. 24 depicts the $^1$H NMR in MeOD of the scale-up of purified chloride salt of Example 1.
Figure 25:
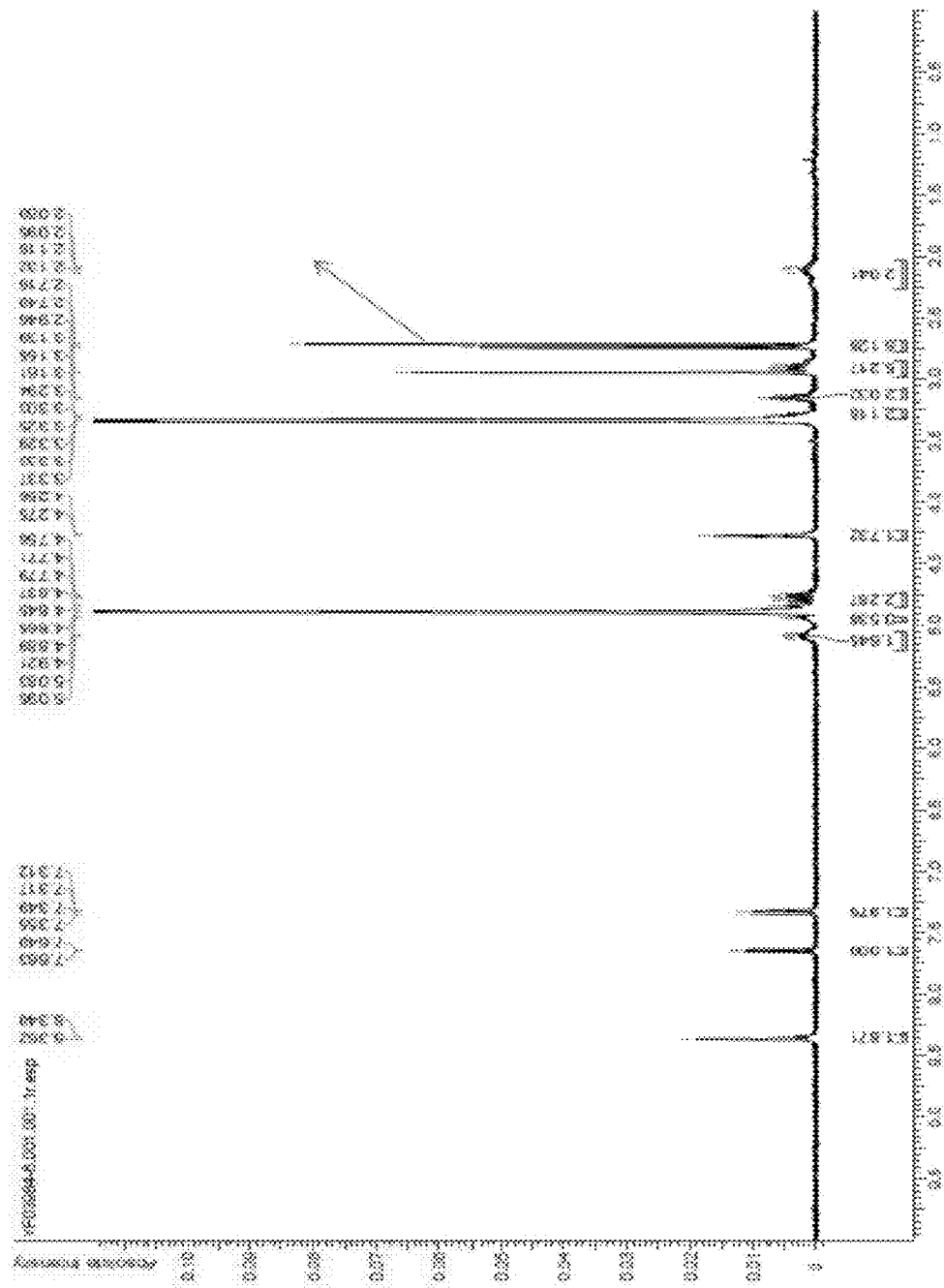
FIG. 25 depicts the $^1$H NMR in MeOD of the scale-up of purified mesylate salt of Example 1.
Figure 26:
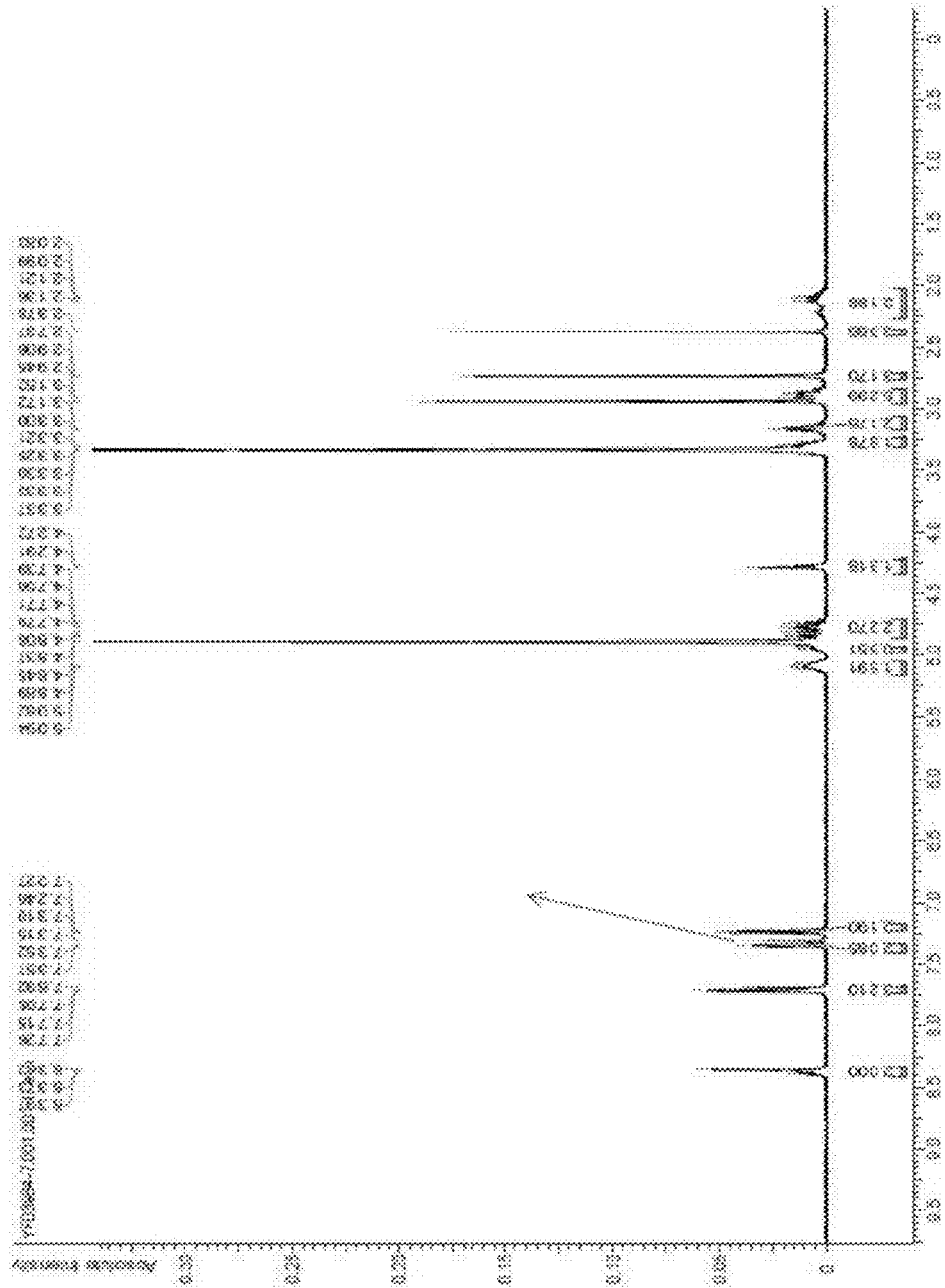
FIG. 26 depicts the $^1$H NMR in MeOD of the scale-up of purified tosylate salt of Example 1.
Figure 27:
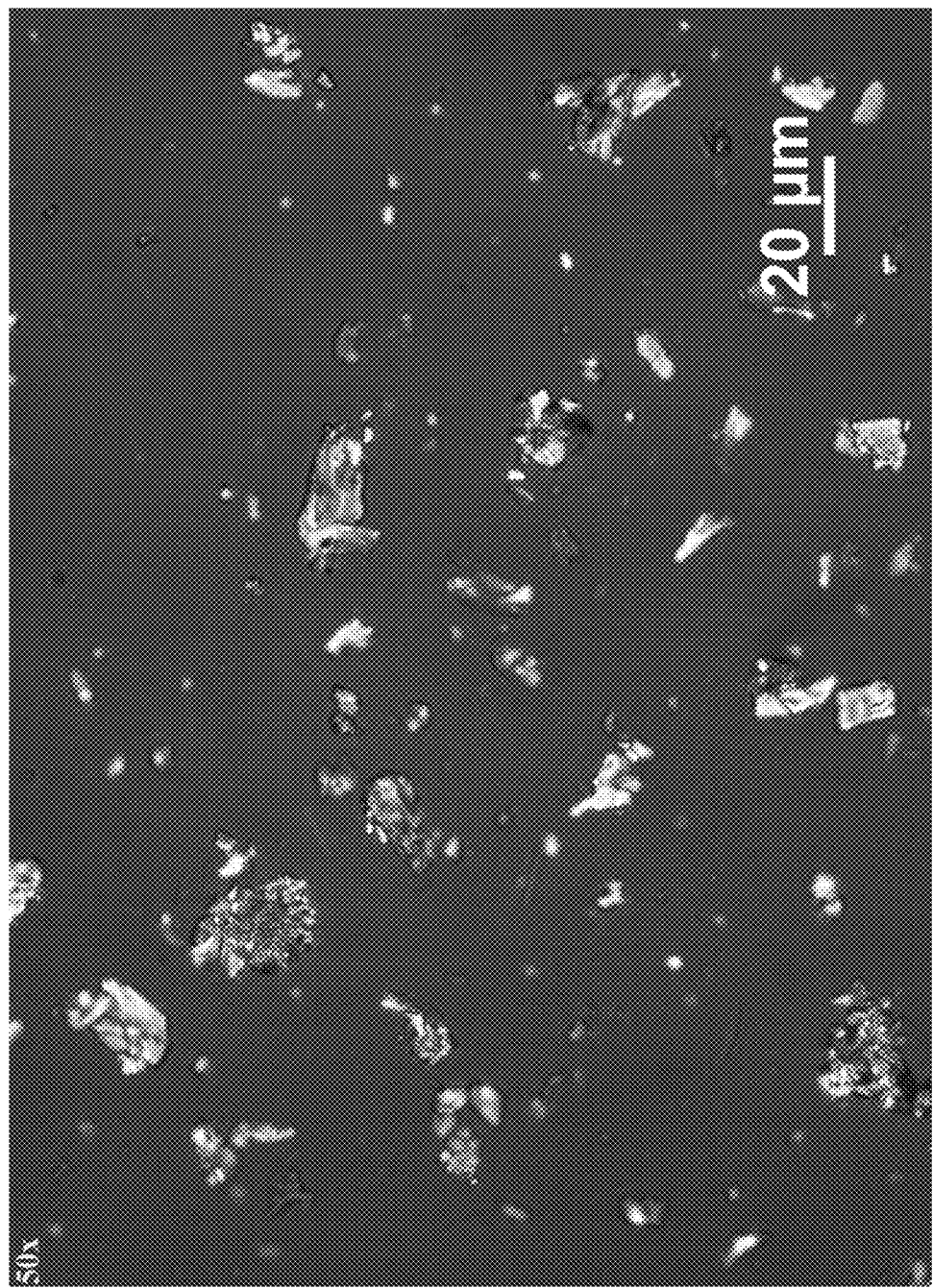
FIG. 27 depicts the PLM of the scale-up of purified chloride salt of Example 1.
Figure 28:
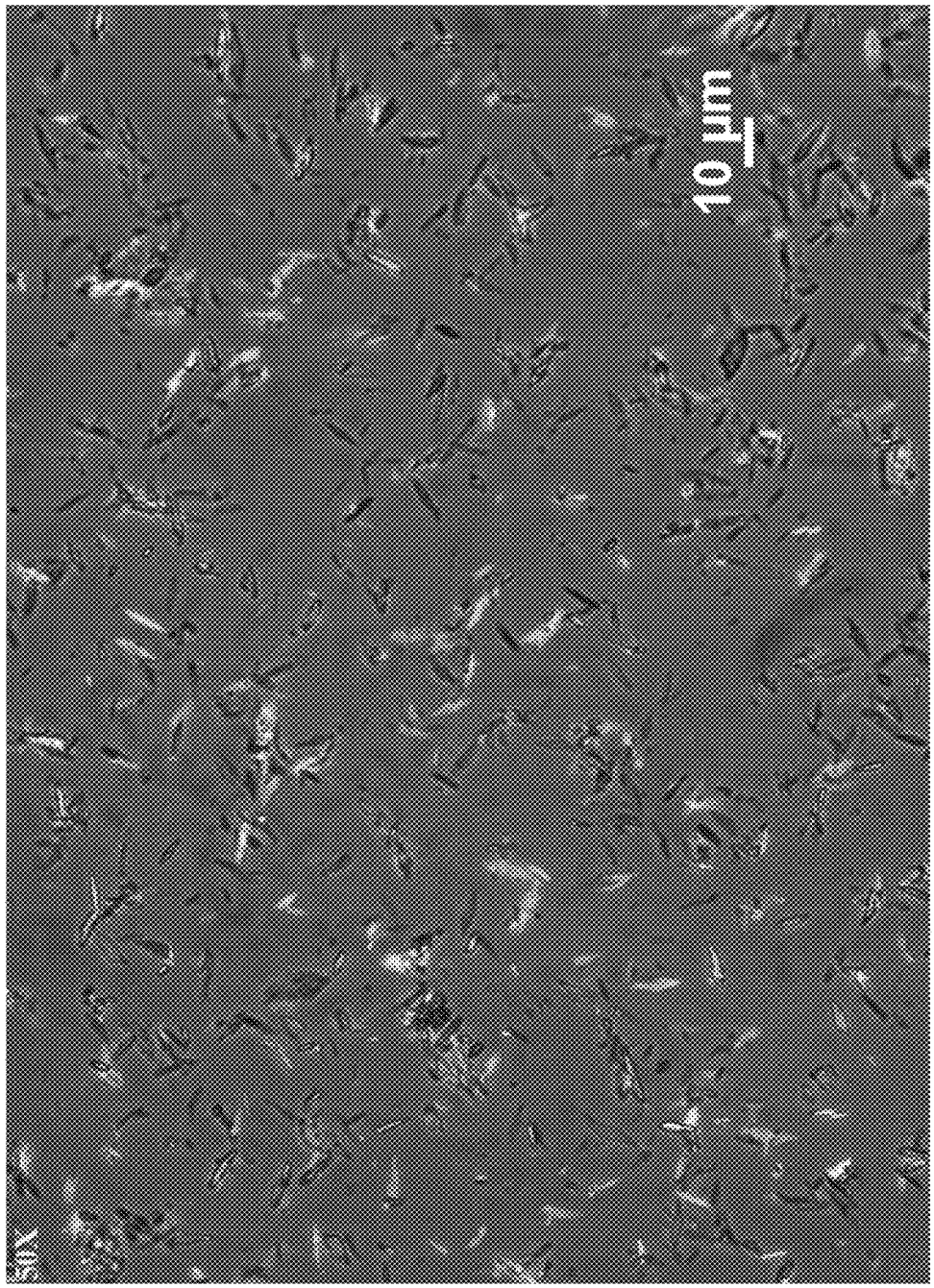
FIG. 28 depicts the PLM of the scale-up of purified mesylate salt of Example 1.
Figure 29:
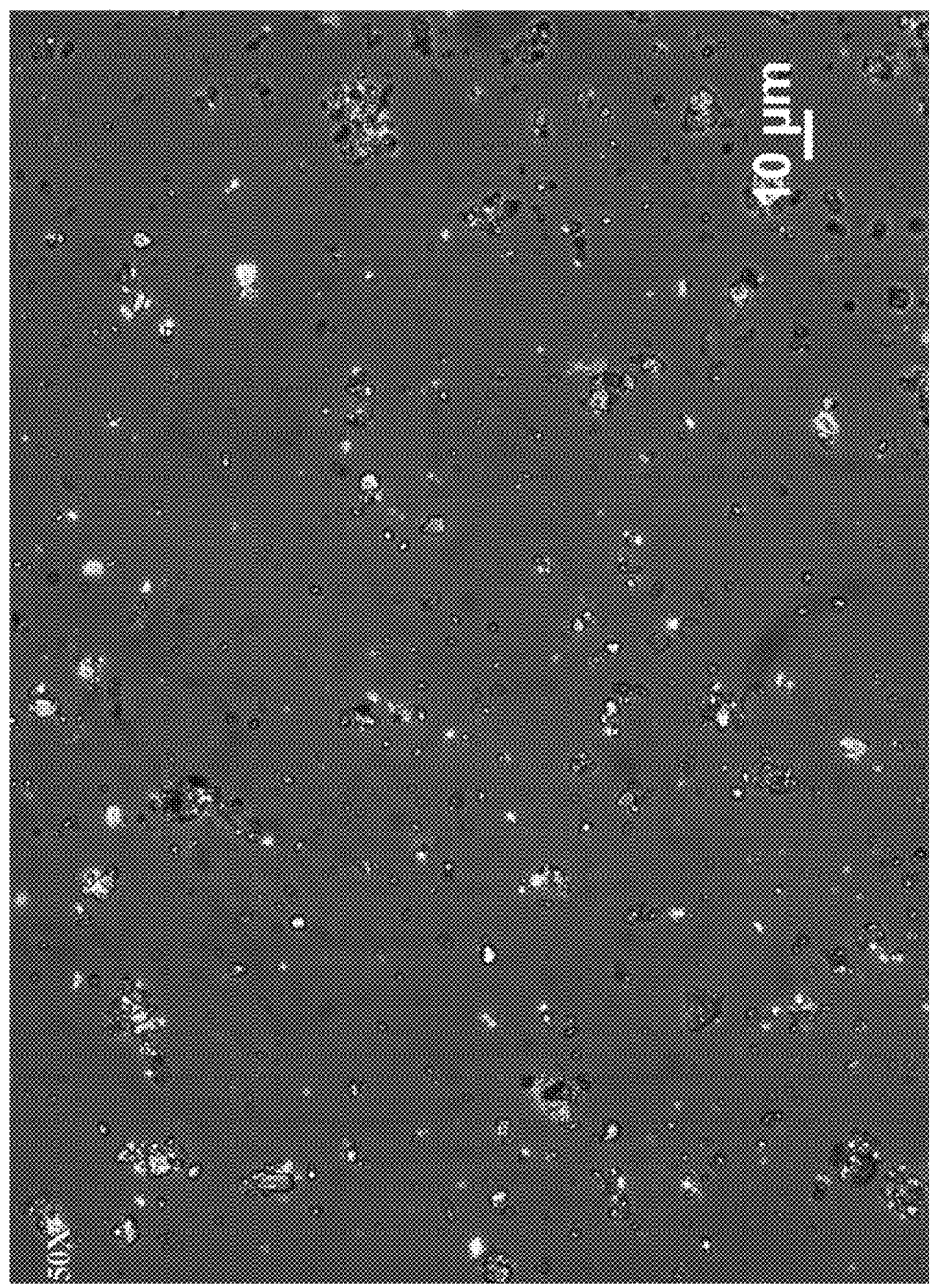
FIG. 29 depicts the PLM of the scale-up of purified tosylate salt of Example 1.
Figure 30:
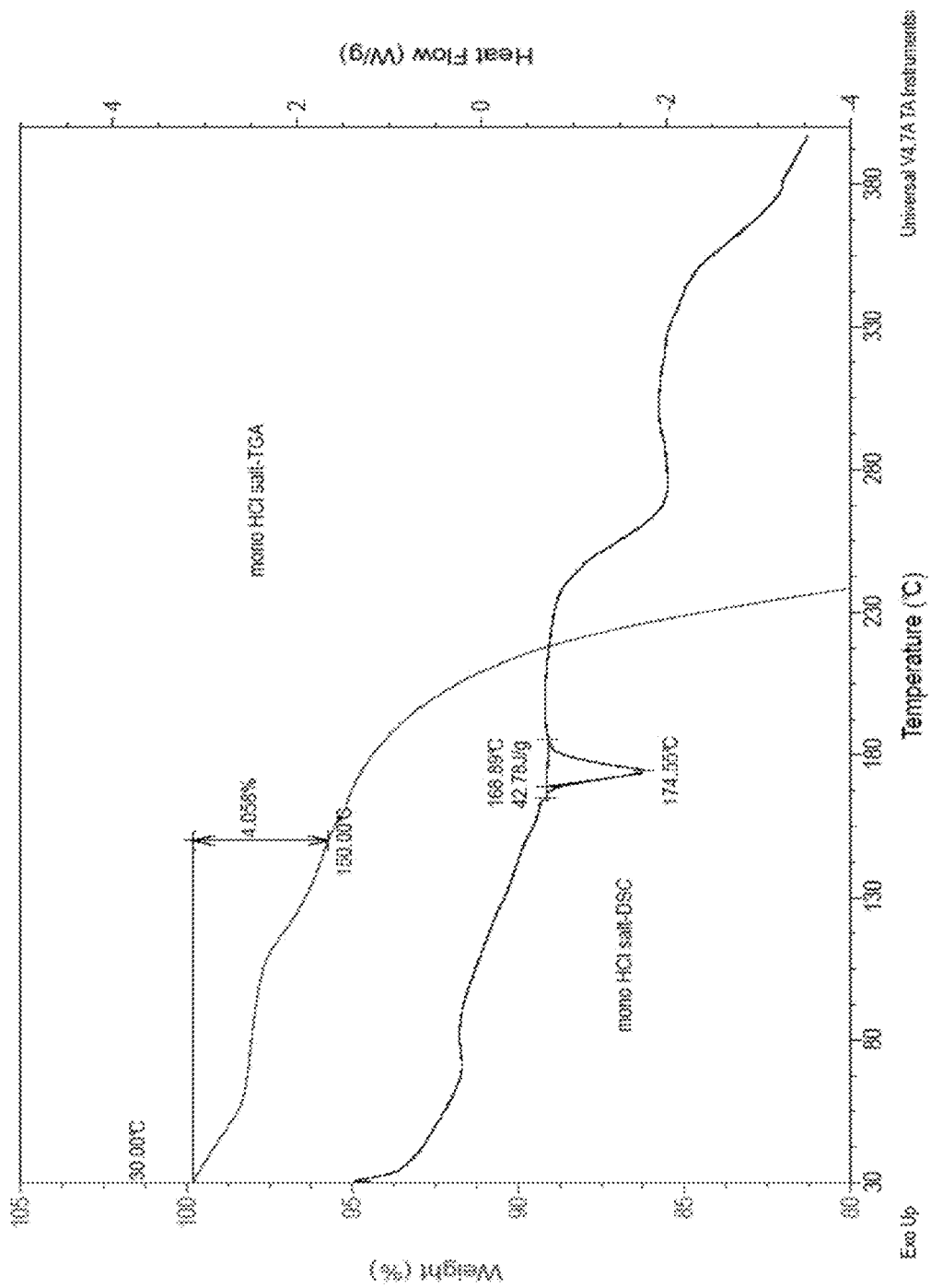
FIG. 30 depicts an overlay of the DSC and TGA of the scale-up of the purified chloride salt of Example 1.
Figure 31:
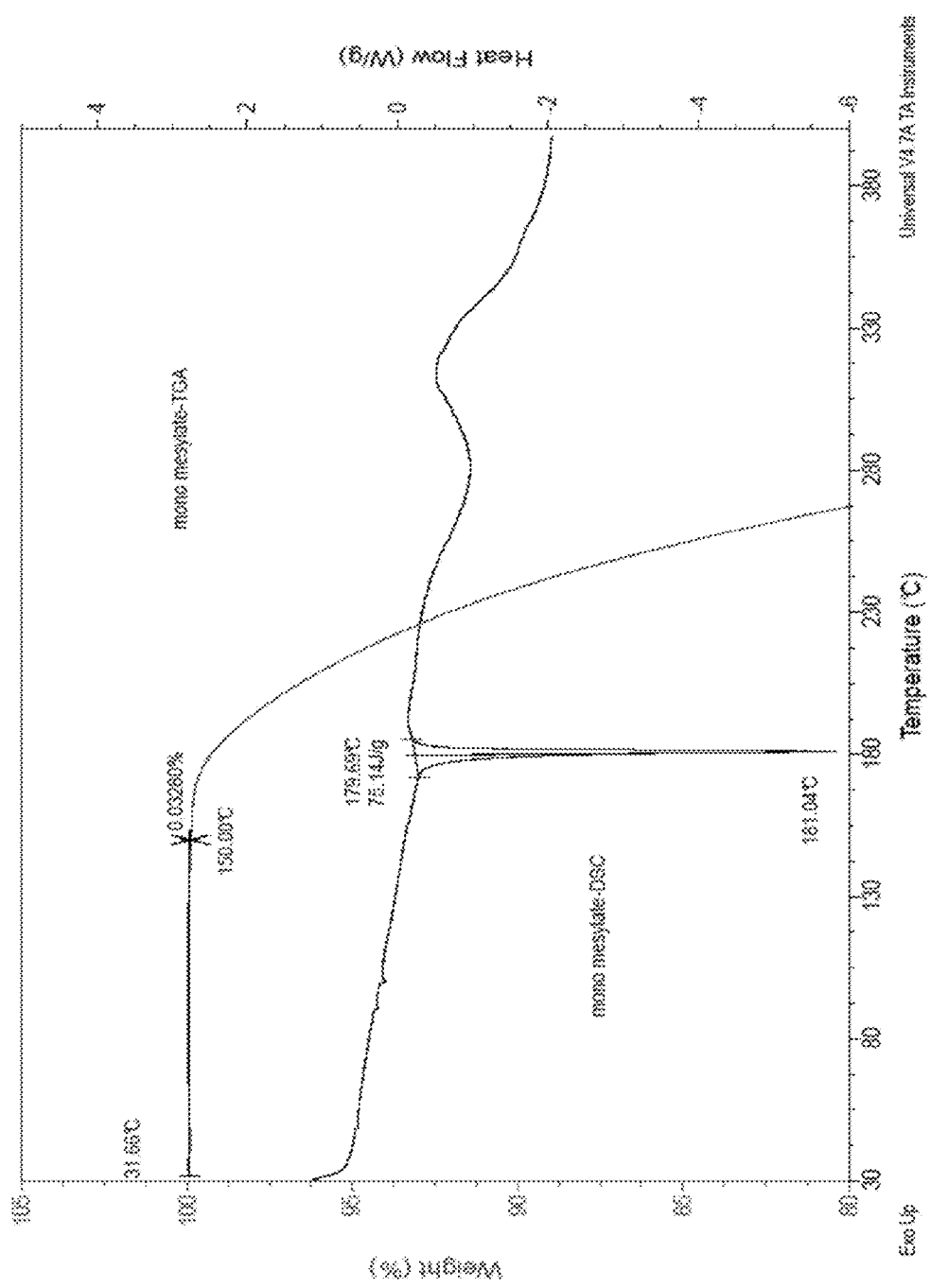
FIG. 31 depicts an overlay of the DSC and TGA of the scale-up of the purified mesylate salt of Example 1.
Figure 32:
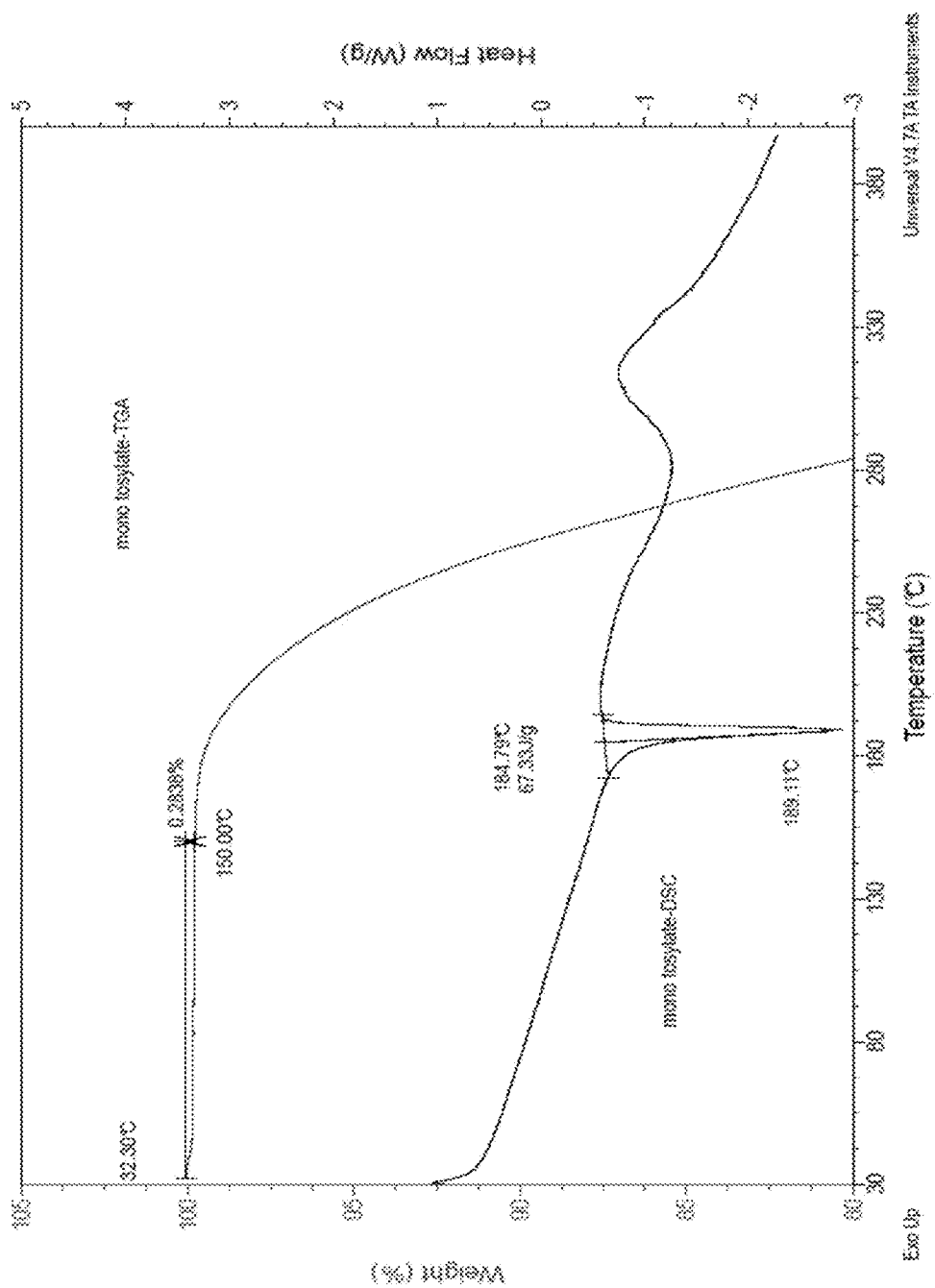
FIG. 32 depicts an overlay of the DSC and TGA of the scale-up of the purified tosylate salt of Example 1.

$^1$HNMR results (FIG. 24, FIG. 25, FIG. 26) of the chloride, mesylate, and tosylate salts showed that the mono mesylate and mono tosylate salts were formed, with the calculated molar ratio (API:acid) confirmed as 1:1. PLM of the chloride, mesylate, and tosylate salts are depicted in FIG. 27, FIG. 28, and FIG. 29, respectively. Overlays of the DSC and TGA for the chloride, mesylate, and tosylate salts are depicted in FIG. 30, FIG. 31, and FIG. 32, respectively.

$^1$H NMR of chloride salt (400 MHz, methanol-$d_4$) δ ppm 2.03-2.27 (m, 2 H), 2.74 (s, 3 H), 2.84-2.96 (m, 5 H), 3.08-3.21 (m, 2 H), 3.25-3.31 (m, 2 H), 4.25-4.30 (m, 2 H), 4.70-5.13 (m, 4 H), 7.32 (d, J=2.51 Hz, 1 H), 7.35 (d, J=2.51 Hz, 1 H), 7.65 (d, J=9.29 Hz, 1 H), 8.33-8.39 (m, 2 H).

$^1$H NMR of mesylate salt (400 MHz, methanol-$d_4$) δ ppm 2.06-2.24 (m, 2 H), 2.72 (s, 3 H), 2.74 (s, 3 H), 2.87-2.96 (m, 5 H), 3.09-3.23 (m, 2 H), 3.26-3.31 (m, 2 H), 4.28 (s, 2 H), 4.73-5.13 (m, 4 H), 7.33 (dd, J=14.93, 2.38 Hz, 2 H), 7.65 (d, J=9.29 Hz, 1 H), 8.33-8.38 (m, 2 H).

$^1$H NMR of tosylate salt (400 MHz, methanol-$d_4$) δ ppm 2.04-2.27 (m, 2 H), 2.38 (s, 3 H), 2.74 (s, 3 H), 2.83-2.96 (m, 5 H), 3.10-3.22 (m, 2 H), 3.25-3.31 (m, 2 H), 4.26-4.31 (m, 2 H, integrates low due to slow exchange with solvent), 4.70-5.10 (m, 4 H), 7.24 (d, J=7.78 Hz, 2 H), 7.31 (d, J=2.01 Hz, 1 H), 7.35 (d, J=2.26 Hz, 1 H), 7.68-7.74 (m, 3 H), 8.35-8.41 (m, 2 H).

Provided herein are salts characterized by having nuclear magnetic resonance NMR peaks as disclosed above. In certain embodiments, salts are characterized by having at least one, at least three, or at least five of the peaks as disclosed above. In certain embodiments, salts are characterized by having between five and ten of the peaks as disclosed above. Such peaks may be referred to by their shift in parts per million.

Provided herein is a chloride salt of Example 1 characterized by having one or more $^1$H nuclear magnetic resonance (NMR) chemical shifts at about 2.0-about 2.3, about 2.7, about 2.8-about 3.0, about 3.1-about 3.2, about 3.3, about 4.3, about 4.7-about 5.1, about 7.3, about 7.4, about 7.7, or about 8.3-about 8.4 parts per million. In certain embodiments, the chloride salt of Example 1 is characterized by having three or more of the shifts. In certain embodiments, the chloride salt of Example 1 is characterized by having five or more of the shifts.

Provided herein is a mesylate salt of Example 1 characterized by having one or more $^1$H nuclear magnetic resonance (NMR) chemical shifts at about 2.1-about 2.2, about 2.7, about 2.9-about 3.0, about 3.1-about 3.2, about 3.3, about 4.3, about 4.7-about 5.1, about 7.3, about 7.7, or about 8.3-about 8.4 parts per million. In certain embodiments, the mesylate salt of Example 1 is characterized by having three or more of the shifts. In certain embodiments, the mesylate salt of Example 1 is characterized by having five or more of the shifts.

Provided herein is a tosylate salt of Example 1 characterized by having one or more $^1$H nuclear magnetic resonance (NMR) chemical shifts at about 2.0-about 2.3, about 2.4, about 2.7, about 2.8-about 3.0, about 3.1-about 3.2, about 3.3, about 4.3, about 4.7-about 5.1, about 7.2, about 7.3, about 7.4, about 7.7, or about 8.4 parts per million. In certain embodiments, the tosylate salt of Example 1 is characterized by having three or more of the shifts. In certain embodiments, the tosylate salt of Example 1 is characterized by having five or more of the shifts.

Also provided are salt of Example 1 characterized by having at least one of the XRPD peaks/shifts and at least one of the NMR peaks/shifts disclosed above, wherein peaks/shifts are both pertinent to the particular salt. In certain embodiments, a salt is characterized by having at least two, three, four, or five of the XRPD peaks/shifts and at least three of the NMR peaks/shifts disclosed above. In certain embodiments, a salt is characterized by having at least three of the XRPD peaks/shifts and at least three of the NMR peaks/shifts disclosed above. In certain embodiments, a salt is characterized by having at least five of the XRPD peaks/shifts and at least five of the NMR peaks/shifts disclosed above.

As per the PLM results (FIG. 31-33), 3 salt candidates displayed birefringence phenomenon, which agreed well with previous XRPD results. The mesylate showed rod like shape, while both the chloride and tosylate salts were irregular block like.

Thermal properties using DSC and TGA (FIG. 34-36) showed that for the HCl salt, a broad endothermic peak with onset temperature at 169° C. shown in FIG. 33 might be the melting of salt, and ~4% weight loss from 30° C. to 150° C. should be the evaporation of residual solvent. For the mesylate, an endothermic peak with onset temperature at 180° C. shown in FIG. 34 might be the melting of the salt, and negligible weight loss indicates an anhydrous form. For the tosylate, an endothermic peak with onset temperature at 185° C. shown in FIG. 35 might be the melting of the salt, and negligible weight loss indicates an anhydrous form.

Provided herein are tosylate and mesylate salts of Example 1 characterized by having XRPD peaks as disclosed above. In certain embodiments, a tosylate or mesylate salt of Example 1 is characterized by having at least five of the XRPD peaks as disclosed in the relevant table(s) above. In certain embodiments, a tosylate or mesylate salt of Example 1 is characterized by having between five and ten of the XRPD peaks as disclosed above. Such peaks may be referred to by their 2 theta shift.

In general, provided herein are salts and polymorphs of Example 1 characterized by having spectral peaks (XRPD, NMR, IR, etc.) as disclosed above and in the Figure(s) below. In certain embodiments, a salt or polymorph of Example 1 is characterized by having at least five of the spectral peaks as disclosed in the relevant table(s) above or Figure(s) below. In certain embodiments, a salt or polymorph of Example 1 is characterized by having between five and ten of the spectral peaks as disclosed above or below. Such peaks may be referred to by their 2 theta shifts (in the case of XRPD); by their chemical shift in ppm, and/or intensity, and/or grouping (in the case of NMR), and absorbance and/or frequency (in the case of IR).

Biological Activity Assays

The following are assays that may be used to evaluate the biological efficacy of compounds and salts thereof disclosed herein.

GLS1 Enzymatic Activity Assay The inhibition of purified recombinant human GAC by varying concentrations of inhibitors is assessed via a dual-coupled enzymatic assay. The glutamate produced by the glutaminase reaction is used by glutamate oxidase to produce α-ketoglutarate, ammonia, and hydrogen peroxide, with this hydrogen peroxide subsequently being used by horseradish peroxidase to produce resorufin in the presence of Amplex UltraRed. The assay buffer consisted of 50 mM Hepes (pH 7.4), 0.25 mM EDTA and 0.1 mM Triton X-100. GAC was incubated with potassium phosphate (10 minutes at room temperature) prior to incubation with inhibitor (10 minutes at room temperature). The final reaction conditions were as follows: 2 nM GAC, 50 mM potassium phosphate, 100 mU/mL glutamate oxidase (Sigma), 1 mM glutamine (Sigma), 100 mU/mL horseradish peroxidase (Sigma), 75 µM Amplex UltraRed (Life Technologies), and 1% (v/v) DMSO. The production of resorufin was monitored on a Perkin Elmer Envision plate reader (excitation 530 nm, emission 590 nm) either in a kinetics or endpoint mode (at 20 minutes). IC50 values were calculated using a four-parameter logistic curve fit.

Proliferation Assay. A549 cells were routinely maintained in RPMI 1640 media (Gibco catalog number 11875-093) supplemented with 10% dialyzed fetal bovine serum using a humidified incubator (37° C., 5% CO2 and ambient O2). In preparation for the viability assay, cells were inoculated into 384-well black CulturPlates (Perkin Elmer) at a density of 1000 cells/well in a volume of 40 uL. Following a 24-hour incubation at 37° C., 5% CO2 and ambient O2, cells were treated with compound (10 uL) in a final DMSO concentration of 0.5% (v/v). The microplates were then incubated for 72 hours (37° C., 5% CO2 and ambient O2). Cell Titer Fluor (Promega) was subsequently added (10 uL of 6× reagent) and mixed for 15 minutes at room temperature. The plates were then incubated for 30 minutes (37° C., 5% CO2 and ambient O2) and fluorescence was subsequently read on the Perkin Elmer Envision plate reader. IC50 values were calculated using a four-parameter logistic curve fit.

Example 1 had an $IC_{50}$ against GLS1 and an $EC_{50}$ against A549 cell proliferation of <100 nM. Salts, solvates, and polymorphs of Example 1 (e.g., Examples 2-11) are expected to have similar activity.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:
1. The compound

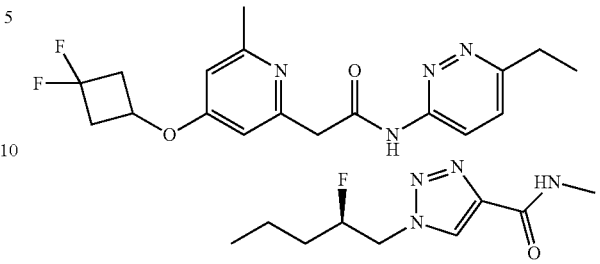

or a salt, solvate, or polymorph thereof.

2. A salt as recited in claim 1, of structural Formula I:

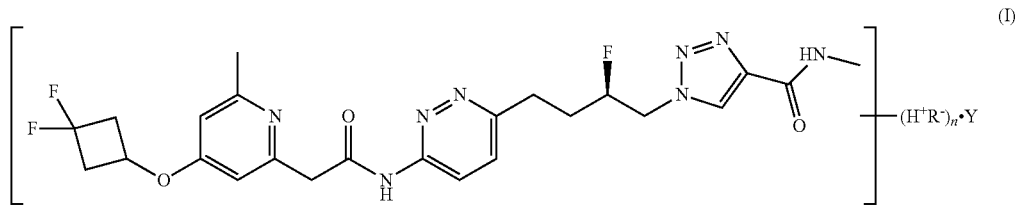

(I)

or a polymorph thereof, wherein:
R⁻ is chosen from Cl⁻, Br⁻, I⁻, $HSO_4^-$, $SO_4^{2-}$, $NO_3^-$, $CH_3SO_3^-$, $PhSO_3^-$, 4-$MePhSO_3^-$, $NaphthaleneSO_3^-$;
n is an integer from 0 to 2; and
Y is an optional solvate.

3. The solid compound

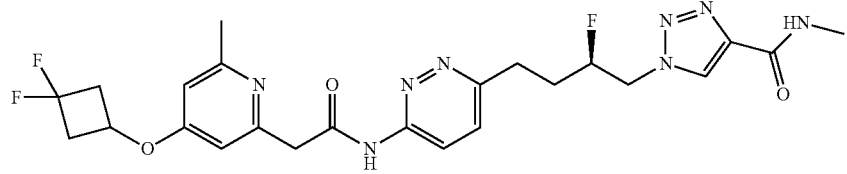

or a polymorph thereof.

4. The solid compound as recited in claim 3, which is crystalline.

5. Polymorph A of the solid compound as recited in claim 3.

6. Polymorph B of the solid compound as recited in claim 3.

7. Polymorph C of the solid compound as recited in claim 3.

8. Polymorph D of the solid compound as recited in claim 3.

9. The polymorph D as recited in claim 8, having one or more x-ray powder diffraction peaks chosen from about 4.0, about 8.0, about 11.6, about 11.9, about 14.9, about 15.9, about 17.6, about 19.9, about 20.2, about 22.4, about 23.7, and about 23.9 degress 2-theta.

10. The Polymorph D as recited in claim 9, which comprises three or more of the peaks.

11. The Polymorph D as recited in claim 9, which comprises five or more of the peaks.

12. The Polymorph D as recited in claim 8, wherein said polymorph displays an endothermic peak in DSC with onset of 197° C.±1° C.

13. The Polymorph D as recited in claim 8, wherein said polymorph is anhydrous.

14. The Polymorph D as recited in claim 8, wherein said polymorph displays weight loss in DSC of less than 1% from 30° C. to 200° C.

15. A composition comprising a compound or polymorph of claim 3, and a pharmaceutically acceptable carrier, adjuvant, or vehicle.

* * * * *